(12) United States Patent
Lipkens et al.

(10) Patent No.: US 11,021,699 B2
(45) Date of Patent: Jun. 1, 2021

(54) SEPARATION USING ANGLED ACOUSTIC WAVES

(71) Applicant: FloDesign Sonics, Inc., Wilbraham, MA (US)

(72) Inventors: Bart Lipkens, Bloomfield, CT (US); Jason Dionne, Simsbury, CT (US); Walter M. Presz, Jr., Wilbraham, MA (US); Kedar C. Chitale, Newton, MA (US); Benjamin Ross-Johnsrud, Northampton, MA (US)

(73) Assignee: FioDesign Sonics, Inc., Wilbraham, MA (US)

( * ) Notice: Subject to any disclaimer, the term of this patent is extended or adjusted under 35 U.S.C. 154(b) by 225 days.

(21) Appl. No.: 15/942,316

(22) Filed: Mar. 30, 2018

(65) Prior Publication Data

US 2018/0298371 A1    Oct. 18, 2018

Related U.S. Application Data

(60) Continuation-in-part of application No. 15/613,790, filed on Jun. 5, 2017, now Pat. No. 10,550,382, which
(Continued)

(51) Int. Cl.
*B01D 21/28* (2006.01)
*C12N 13/00* (2006.01)
(Continued)

(52) U.S. Cl.
CPC ........... *C12N 13/00* (2013.01); *B01D 21/283* (2013.01); *B01L 3/502761* (2013.01); *C12M 47/02* (2013.01); *C12M 47/04* (2013.01);

*C12N 1/02* (2013.01); *G01N 15/1484* (2013.01); *A61M 1/3678* (2014.02); *B01L 2300/0864* (2013.01); *B01L 2300/0867* (2013.01);
(Continued)

(58) Field of Classification Search
None
See application file for complete search history.

(56) References Cited

U.S. PATENT DOCUMENTS 2,473,971 A    6/1949 Ross
2,667,944 A    2/1954 Crites
(Continued)

FOREIGN PATENT DOCUMENTS

AU    2002236405    9/2002
CN    105 087 788 A    11/2015
(Continued)

OTHER PUBLICATIONS

Ding et al., Cell separation using tilted-angle standing surface acoustic waves, Sep. 9, 2014, PNAS, vol. 111, No. 36, pp. 12992-12997 (Year: 2014).*
(Continued)

*Primary Examiner* — Holly Kipouros
(74) *Attorney, Agent, or Firm* — FloDesign Sonics, Inc.

(57) ABSTRACT

Methods and systems for separating material from a host fluid use an acoustophoresis device. These methods and systems can deflect material (e.g., a second fluid, cells, beads or other particles, exosomes, viruses, oil droplets) in host fluid streams at high flow rates.

6 Claims, 26 Drawing Sheets

Related U.S. Application Data is a division of application No. 15/143,481, filed on Apr. 29, 2016, now Pat. No. 9,670,477.

(60) Provisional application No. 62/316,933, filed on Apr. 1, 2016, provisional application No. 62/154,690, filed on Apr. 29, 2015, provisional application No. 62/479,309, filed on Mar. 30, 2017, provisional application No. 62/485,229, filed on Apr. 13, 2017.

(51) Int. Cl.
   *C12M 1/00*     (2006.01)
   *B01L 3/00*     (2006.01)
   *G01N 15/14*    (2006.01)
   *C12N 1/02*     (2006.01)
   *G01N 15/10*    (2006.01)
   *G01N 15/00*    (2006.01)
   *A61M 1/36*     (2006.01)
   *G01N 15/02*    (2006.01)

(52) U.S. Cl.
   CPC .......... *B01L 2400/0436* (2013.01); *B01L 2400/0439* (2013.01); *G01N 15/0255* (2013.01); *G01N 2015/0053* (2013.01); *G01N 2015/0288* (2013.01); *G01N 2015/0294* (2013.01); *G01N 2015/1006* (2013.01); *G01N 2015/149* (2013.01)

(56) References Cited

U.S. PATENT DOCUMENTS

| | | |
|---|---|---|
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Schwartzman et al. |
| 4,125,789 A | 11/1978 | Van Schoiack |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,254,661 A | 3/1981 | Kossoff et al. |
| 4,320,659 A | 3/1982 | Lynnworth et al. |
| 4,344,448 A | 8/1982 | Potts |
| 4,398,325 A | 8/1983 | Piaget et al. |
| 4,484,907 A | 11/1984 | Sheeran, Jr. |
| 4,552,669 A | 11/1985 | Sekellick |
| 4,666,595 A | 5/1987 | Graham |
| 4,673,512 A | 6/1987 | Schram |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,860,993 A | 8/1989 | Goode |
| 4,878,210 A | 10/1989 | Mitome |
| 4,983,189 A | 1/1991 | Peterson et al. |
| 5,059,811 A | 10/1991 | King et al. |
| 5,062,965 A | 11/1991 | Bernou et al. |
| 5,085,783 A | 2/1992 | Feke et al. |
| 5,164,094 A | 11/1992 | Stuckart |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,475,486 A | 12/1995 | Paoli |
| 5,484,537 A | 1/1996 | Whitworth |
| 5,527,460 A | 6/1996 | Trampler et al. |
| 5,560,362 A | 10/1996 | Sliwa, Jr. et al. |
| 5,562,823 A | 10/1996 | Reeves |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,947,299 A | 9/1999 | Vazquez et al. |
| 5,951,456 A | 9/1999 | Scott |
| 6,090,295 A | 6/2000 | Raghavarao et al. |
| 6,166,231 A | 12/2000 | Hoeksema |
| 6,216,538 B1 | 4/2001 | Yasuda et al. |
| 6,205,848 B1 | 6/2001 | Faber et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,475,151 B2 | 11/2002 | Koger et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,641,708 B1 | 11/2003 | Becker et al. |
| 6,649,069 B2 | 11/2003 | DeAngelis |
| 6,699,711 B1 | 3/2004 | Hahn et al. |
| 6,727,451 B1 | 4/2004 | Fuhr et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,674,630 B2 | 3/2010 | Siversson |
| 7,837,040 B2 | 11/2010 | Ward et al. |
| 7,846,382 B2 | 12/2010 | Strand et al. |
| 7,968,049 B2 | 6/2011 | Takahashi et al. |
| 8,075,786 B2 | 12/2011 | Bagajewicz |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |

(56) References Cited

U.S. PATENT DOCUMENTS

| | | |
|---|---|---|
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 9,532,769 B2 | 1/2017 | Dayton et al. |
| 9,533,241 B2 | 1/2017 | Presz, Jr. et al. |
| 9,550,134 B2 | 1/2017 | Lipkens et al. |
| 9,550,998 B2 | 1/2017 | Williams |
| 9,556,271 B2 | 1/2017 | Blumberg et al. |
| 9,556,411 B2 | 1/2017 | Lipkens et al. |
| 9,566,352 B2 | 2/2017 | Holmes et al. |
| 9,567,559 B2 | 2/2017 | Lipkens et al. |
| 9,567,609 B2 | 2/2017 | Paschon et al. |
| 9,572,897 B2 | 2/2017 | Bancel et al. |
| 9,573,995 B2 | 2/2017 | Schurpf et al. |
| 9,574,014 B2 | 2/2017 | Williams et al. |
| 9,580,500 B2 | 2/2017 | Schurpf et al. |
| 9,587,003 B2 | 3/2017 | Bancel et al. |
| 9,597,357 B2 | 3/2017 | Gregory et al. |
| 9,597,380 B2 | 3/2017 | Chakraborty et al. |
| 9,605,074 B2 | 3/2017 | Shah |
| 9,605,266 B2 | 3/2017 | Rossi et al. |
| 9,606,086 B2 | 3/2017 | Ding et al. |
| 9,608,547 B2 | 3/2017 | Ding et al. |
| 9,611,465 B2 | 4/2017 | Handa et al. |
| 9,616,090 B2 | 4/2017 | Conway et al. |
| 9,623,348 B2 | 4/2017 | McCarthy et al. |
| 9,629,877 B2 | 4/2017 | Cooper et al. |
| D787,630 S | 5/2017 | Lipkens et al. |
| 9,644,180 B2 | 5/2017 | Kahvejian et al. |
| 9,645,060 B2 | 5/2017 | Fiering |
| 9,656,263 B2 | 5/2017 | Laurell et al. |
| 9,657,290 B2 | 5/2017 | Dimov et al. |
| 9,662,375 B2 | 5/2017 | Jensen et al. |
| 9,663,756 B1 | 5/2017 | Lipkens et al. |
| 9,670,477 B2 | 6/2017 | Lipkens et al. |
| 9,670,938 B2 | 6/2017 | Beliavsky |
| 9,675,668 B2 | 6/2017 | Bancel et al. |
| 9,675,902 B2 | 6/2017 | Lipkens et al. |
| 9,675,906 B2 | 6/2017 | Lipkens et al. |
| 9,677,055 B2 | 6/2017 | Jones et al. |
| 9,685,155 B2 | 6/2017 | Hershey et al. |
| 9,686,096 B2 | 6/2017 | Lipkens et al. |
| 9,688,958 B2 | 6/2017 | Kennedy, III et al. |
| 9,689,234 B2 | 6/2017 | Gregory et al. |
| 9,689,802 B2 | 6/2017 | Caseres et al. |
| 9,695,063 B2 | 7/2017 | Rietman et al. |
| 9,695,442 B2 | 7/2017 | Guschin et al. |
| 9,810,665 B2 | 11/2017 | Fernald et al. |
| 9,833,763 B2 | 12/2017 | Fernald et al. |
| 9,869,659 B2 | 1/2018 | Buckland et al. |
| 9,872,900 B2 | 1/2018 | Ciaramella et al. |
| 9,873,126 B2 | 1/2018 | Mao et al. |
| 9,873,894 B2 | 1/2018 | Conway et al. |
| 9,878,056 B2 | 1/2018 | Bancel et al. |
| 9,878,536 B2 | 1/2018 | Foresti et al. |
| 9,879,087 B2 | 1/2018 | DeSander et al. |
| 9,990,297 B2 | 1/2018 | Conway et al. |
| 9,907,846 B2 | 3/2018 | Morein et al. |
| 9,908,288 B2 | 3/2018 | Harkness |
| 9,909,117 B2 | 3/2018 | Kaduchak |
| 9,909,313 B1 | 3/2018 | Grubbs |
| 9,913,656 B2 | 3/2018 | Stulen |
| 9,913,866 B2 | 3/2018 | O'Shea et al. |
| 9,925,277 B2 | 3/2018 | Almarsson et al. |
| 9,926,382 B2 | 3/2018 | Fischer et al. |
| 9,937,207 B2 | 4/2018 | Gregory et al. |
| 9,938,390 B2 | 4/2018 | Storti et al. |
| 9,943,599 B2 | 4/2018 | Gehl et al. |
| 9,944,702 B2 | 4/2018 | Galetto |
| 9,944,709 B2 | 4/2018 | Galetto |
| 9,994,743 B2 | 4/2018 | El-Zahab |
| 9,974,898 B2 | 5/2018 | Spain et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0057866 A1 | 3/2004 | Zumeris et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2005/0239198 A1 | 10/2005 | Kunas |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0138108 A1 | 6/2007 | Hadfield et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0042253 A1 | 2/2009 | Hiller et al. |
| 2009/0048805 A1 | 2/2009 | Kaduchak et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |

(56) References Cited

U.S. PATENT DOCUMENTS

| | | |
|---|---|---|
| 2011/0207225 A1 | 8/2011 | Mehta et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0161903 A1 | 6/2012 | Thomas et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0206688 A1 | 8/2013 | El-Naas |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2013/0316412 A1 | 11/2013 | Schultz et al. |
| 2014/0011240 A1 | 1/2014 | Lipkens et al. |
| 2014/0017758 A1 | 1/2014 | Kniep et al. |
| 2014/0102947 A1 | 4/2014 | Baym et al. |
| 2014/0141413 A1 | 5/2014 | Laugham, Jr. et al. |
| 2014/0154795 A1 | 6/2014 | Lipkens et al. |
| 2014/0319077 A1 | 10/2014 | Lipkens et al. |
| 2014/0329997 A1 | 11/2014 | Kennedy, III et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0252317 A1 | 9/2015 | Lipkens et al. |
| 2015/0274550 A1 | 10/2015 | Lipkens et al. |
| 2015/0321129 A1 | 11/2015 | Lipkens et al. |
| 2016/0060615 A1 | 3/2016 | Walther et al. |
| 2016/0089620 A1 | 3/2016 | Lipkens et al. |
| 2016/0102284 A1 | 4/2016 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0287778 A1* | 10/2016 | Leach |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325039 A1 | 11/2016 | Leach et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |
| 2016/0368000 A1 | 12/2016 | Dionne et al. |
| 2016/0369236 A1 | 12/2016 | Kennedy, III et al. |
| 2016/0370326 A9 | 12/2016 | Kaduchak et al. |
| 2017/0000413 A1 | 1/2017 | Clymer et al. |
| 2017/0002060 A1 | 1/2017 | Bolen et al. |
| 2017/0002839 A1 | 1/2017 | Burkland et al. |
| 2017/0007679 A1 | 1/2017 | Maeder et al. |
| 2017/0008029 A1 | 1/2017 | Lipkens et al. |
| 2017/0016025 A1 | 1/2017 | Poirot et al. |
| 2017/0016027 A1 | 1/2017 | Lee et al. |
| 2017/0020926 A1 | 1/2017 | Mata-Fink et al. |
| 2017/0029802 A1 | 2/2017 | Lipkens et al. |
| 2017/0035866 A1 | 2/2017 | Poirot et al. |
| 2017/0037386 A1 | 2/2017 | Jones et al. |
| 2017/0038288 A1 | 2/2017 | Ward et al. |
| 2017/0042770 A1 | 2/2017 | Warner et al. |
| 2017/0044517 A1 | 2/2017 | Lipkens et al. |
| 2017/0049949 A1 | 2/2017 | Gilmanshin et al. |
| 2017/0056448 A1 | 3/2017 | Glick et al. |
| 2017/0058036 A1 | 3/2017 | Ruiz-Opazo et al. |
| 2017/0065636 A1 | 3/2017 | Moriarty et al. |
| 2017/0066015 A1 | 3/2017 | Lipkens et al. |
| 2017/0067021 A1 | 3/2017 | Moriarty et al. |
| 2017/0067022 A1 | 3/2017 | Poirot et al. |
| 2017/0072405 A1 | 3/2017 | Mao et al. |
| 2017/0073406 A1 | 3/2017 | Schurpf et al. |
| 2017/0073423 A1 | 3/2017 | Juillerat et al. |
| 2017/0073638 A1 | 3/2017 | Campana et al. |
| 2017/0073684 A1 | 3/2017 | Rossi et al. |
| 2017/0073685 A1 | 3/2017 | Maeder et al. |
| 2017/0080070 A1 | 3/2017 | Weinschenk et al. |
| 2017/0080423 A1 | 3/2017 | Dauson et al. |
| 2017/0081629 A1 | 3/2017 | Lipkens et al. |
| 2017/0088809 A1 | 3/2017 | Lipkens et al. |
| 2017/0088844 A1 | 3/2017 | Williams |
| 2017/0089826 A1 | 3/2017 | Lin |
| 2017/0096455 A1 | 4/2017 | Baric et al. |
| 2017/0107536 A1 | 4/2017 | Zhang et al. |
| 2017/0107539 A1 | 4/2017 | Yu et al. |
| 2017/0119820 A1 | 5/2017 | Moriarty et al. |
| 2017/0128523 A1 | 5/2017 | Ghatnekar et al. |
| 2017/0128857 A1 | 5/2017 | Lipkens et al. |
| 2017/0130200 A1 | 5/2017 | Moriarty et al. |
| 2017/0136168 A1 | 5/2017 | Spain et al. |
| 2017/0137491 A1 | 5/2017 | Matheson et al. |
| 2017/0137774 A1 | 5/2017 | Lipkens et al. |
| 2017/0137775 A1 | 5/2017 | Lipkens et al. |
| 2017/0137802 A1 | 5/2017 | Lipkens et al. |
| 2017/0145094 A1 | 5/2017 | Galetto |
| 2017/0151345 A1 | 6/2017 | Shah |
| 2017/0152502 A1 | 6/2017 | Scharenberg et al. |
| 2017/0152503 A1 | 6/2017 | Scharenberg et al. |
| 2017/0152504 A1 | 6/2017 | Scharenberg et al. |
| 2017/0152505 A1 | 6/2017 | Scharenberg et al. |
| 2017/0152527 A1 | 6/2017 | Paschon et al. |
| 2017/0152528 A1 | 6/2017 | Zhang et al. |
| 2017/0158749 A1 | 6/2017 | Cooper et al. |
| 2017/0159005 A1 | 6/2017 | Lipkens et al. |
| 2017/0159007 A1 | 6/2017 | Lipkens et al. |
| 2017/0166860 A1 | 6/2017 | Presz, Jr. et al. |
| 2017/0166877 A1 | 6/2017 | Bayle et al. |
| 2017/0166878 A9 | 6/2017 | Thanos et al. |
| 2017/0166903 A1 | 6/2017 | Zhang et al. |
| 2017/0173080 A1 | 6/2017 | Lee et al. |
| 2017/0173128 A1 | 6/2017 | Hoge et al. |
| 2017/0173498 A9 | 6/2017 | Lipkens et al. |
| 2017/0175073 A1 | 6/2017 | Lipkens et al. |
| 2017/0175125 A1 | 6/2017 | Welstead et al. |
| 2017/0175139 A1 | 6/2017 | Wu et al. |
| 2017/0175144 A1 | 6/2017 | Zhang et al. |
| 2017/0175509 A1 | 6/2017 | Abdel-Fattah et al. |
| 2017/0175720 A1 | 6/2017 | Tang et al. |
| 2017/0183390 A1 | 6/2017 | Springer et al. |
| 2017/0183413 A1 | 6/2017 | Galetto |
| 2017/0183418 A1 | 6/2017 | Galetto |
| 2017/0183420 A1 | 6/2017 | Gregory et al. |
| 2017/0184486 A1 | 6/2017 | Mach et al. |
| 2017/0189450 A1 | 7/2017 | Conway et al. |
| 2017/0190767 A1 | 7/2017 | Schurpf et al. |
| 2017/0191022 A1 | 7/2017 | Lipkens et al. |
| 2017/0232439 A1 | 8/2017 | Suresh et al. |
| 2017/0374730 A1 | 12/2017 | Flores |
| 2018/0000311 A1 | 1/2018 | Lipkens et al. |
| 2018/0000870 A1 | 1/2018 | Britt |
| 2018/0000910 A1 | 1/2018 | Chakraborty et al. |

(56) References Cited

U.S. PATENT DOCUMENTS

| | | | |
|---|---|---|---|
| 2018/0008707 A1 | 1/2018 | Bussmer et al. |
| 2018/0009158 A1 | 1/2018 | Harkness et al. |
| 2018/0009888 A9 | 1/2018 | Baumeister et al. |
| 2018/0009895 A1 | 1/2018 | Smith et al. |
| 2018/0010085 A1 | 1/2018 | Lipkens et al. |
| 2018/0010117 A1 | 1/2018 | Paschon et al. |
| 2018/0014846 A1 | 1/2018 | Rhee |
| 2018/0015128 A1 | 1/2018 | Britt |
| 2018/0015392 A1 | 1/2018 | Lipkens et al. |
| 2018/0016570 A1 | 1/2018 | Lipkens et al. |
| 2018/0016572 A1 | 1/2018 | Tang |
| 2018/0020295 A1 | 1/2018 | Pander et al. |
| 2018/0021379 A1 | 1/2018 | Galetto et al. |
| 2018/0022798 A1 | 1/2018 | Shurpf et al. |
| 2018/0028683 A1 | 2/2018 | Wong et al. |
| 2018/0043473 A1 | 2/2018 | Helvajian et al. |
| 2018/0049767 A1 | 2/2018 | Gee et al. |
| 2018/0051089 A1 | 2/2018 | Galettto et al. |
| 2018/0051265 A1 | 2/2018 | Cooper |
| 2018/0052095 A1 | 2/2018 | Cumbo et al. |
| 2018/0052147 A1 | 2/2018 | Zeng |
| 2018/0055529 A1 | 3/2018 | Messerly et al. |
| 2018/0055530 A1 | 3/2018 | Messerly et al. |
| 2018/0055531 A1 | 3/2018 | Messerly et al. |
| 2018/0055532 A1 | 3/2018 | Messerly et al. |
| 2018/0055997 A1 | 3/2018 | Cabrera et al. |
| 2018/0056095 A1 | 3/2018 | Messerly et al. |
| 2018/0057810 A1 | 3/2018 | Zhang et al. |
| 2018/0058439 A1 | 3/2018 | Locke et al. |
| 2018/0066223 A1 | 3/2018 | Lim |
| 2018/0066224 A1 | 3/2018 | Lipkens et al. |
| 2018/0066242 A1 | 3/2018 | Zhang |
| 2018/0067044 A1 | 3/2018 | Kaduchak et al. |
| 2018/0071363 A1 | 3/2018 | Ghatnekar et al. |
| 2018/0071981 A1 | 3/2018 | Collino et al. |
| 2018/0078268 A1 | 3/2018 | Messerly |
| 2018/0080026 A1 | 3/2018 | Rossi et al. |
| 2018/0085743 A1 | 3/2018 | Yavorsky et al. |
| 2018/0087044 A1 | 3/2018 | Lipkens et al. |
| 2018/0088083 A1 | 3/2018 | Sinha |
| 2018/0092338 A1 | 4/2018 | Hering et al. |
| 2018/0092660 A1 | 4/2018 | Houser et al. |
| 2018/0094022 A1 | 4/2018 | Bracewell et al. |
| 2018/0095067 A1 | 4/2018 | Huff et al. |
| 2018/0098785 A1 | 4/2018 | Price et al. |
| 2018/0100134 A1 | 4/2018 | Lim |
| 2018/0100204 A1 | 4/2018 | O'Shea |
| 2018/0130491 A1 | 5/2018 | Mathur |

FOREIGN PATENT DOCUMENTS

| | | |
|---|---|---|
| CN | 104722106 B | 4/2016 |
| DE | 30 27 433 A1 | 2/1982 |
| DE | 32 18 488 A1 | 11/1983 |
| DE | 196 48 519 A1 | 6/1998 |
| DE | 103 19 467 B3 | 7/2004 |
| DE | 10 2008 006 501 A1 | 9/2008 |
| DE | 10 2014 206 823 A1 | 10/2015 |
| EP | 0 292 470 B1 | 11/1988 |
| EP | 0 167 406 B1 | 7/1991 |
| EP | 0 641 606 | 3/1995 |
| EP | 1 175 931 A1 | 1/2002 |
| EP | 1 254 669 B1 | 11/2002 |
| EP | 1 308 724 A2 | 5/2003 |
| EP | 2 209 545 | 7/2010 |
| EP | 270152 A1 | 1/2018 |
| EP | 2419511 | 1/2018 |
| EP | 3068888 | 1/2018 |
| EP | 3257600 | 1/2018 |
| EP | 3274453 | 1/2018 |
| EP | 3274454 | 1/2018 |
| EP | 3275894 | 1/2018 |
| EP | 278108 | 2/2018 |
| EP | 3279315 | 2/2018 |
| EP | 3286214 | 2/2018 |
| EP | 2289535 | 3/2018 |
| EP | 2545068 | 3/2018 |
| EP | 2675540 | 3/2018 |
| EP | 2750683 | 3/2018 |
| EP | 2796102 | 3/2018 |
| EP | 3066201 | 3/2018 |
| EP | 3066998 | 3/2018 |
| EP | 3107552 | 3/2018 |
| EP | 3288660 | 3/2018 |
| EP | 3288683 | 3/2018 |
| EP | 3289362 | 3/2018 |
| EP | 3291842 | 3/2018 |
| EP | 3291852 | 3/2018 |
| EP | 3292142 | 3/2018 |
| EP | 3292195 | 3/2018 |
| EP | 3292515 | 3/2018 |
| EP | 3294343 | 3/2018 |
| EP | 3294764 | 3/2018 |
| EP | 3294857 | 3/2018 |
| EP | 3294871 | 3/2018 |
| EP | 3294888 | 3/2018 |
| EP | 3294896 | 3/2018 |
| EP | 3296302 | 3/2018 |
| EP | 3297740 | 3/2018 |
| EP | 3298046 | 3/2018 |
| EP | 3164488 | 4/2018 |
| EP | 3301115 | 4/2018 |
| EP | 3302783 | 4/2018 |
| EP | 3302789 | 4/2018 |
| EP | 3303558 | 4/2018 |
| EP | 3306310 | 4/2018 |
| GB | 2 420 510 A | 5/2006 |
| JP | 9-136090 | 5/1997 |
| KR | 1442486 | 9/2014 |
| RU | 2037327 C1 | 6/1995 |
| RU | 2085933 | 7/1997 |
| SU | 629496 | 10/1978 |
| WO | WO 1987/07178 A1 | 12/1987 |
| WO | WO 89/11899 A1 | 12/1989 |
| WO | WO 90/05008 | 3/1990 |
| WO | WO 95/01214 A1 | 1/1995 |
| WO | WO 97/34643 | 9/1997 |
| WO | WO 1998/017373 | 4/1998 |
| WO | WO 98/50133 A1 | 11/1998 |
| WO | WO 00/41794 | 7/2000 |
| WO | WO 02/072234 A1 | 9/2002 |
| WO | WO 02/072236 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/131947 A2 | 10/2011 |
| WO | WO 2011/161463 A2 | 12/2011 |
| WO | WO 2013/043044 A1 | 3/2013 |
| WO | WO 2013/043297 A1 | 3/2013 |
| WO | WO 2013/049623 A1 | 4/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | WO 2014/046605 A1 | 3/2014 |
| WO | WO 2014/055219 A2 | 4/2014 |
| WO | WO 2014/124306 A1 | 8/2014 |
| WO | WO 2014/153651 | 10/2014 |
| WO | WO 2015/006730 | 1/2015 |
| WO | WO 2015/102528 | 7/2015 |
| WO | WO 2016/004398 A2 | 1/2016 |
| WO | WO 2016/124542 | 8/2016 |
| WO | WO 2016/176663 | 11/2016 |
| WO | WO 2016/209082 | 12/2016 |
| WO | WO 2017/041102 | 3/2017 |

(56) References Cited

FOREIGN PATENT DOCUMENTS

| WO | WO 20174201349 | 11/2017 |
|---|---|---|
| WO | WO 2017218714 | 12/2017 |
| WO | WO 2018/009894 A1 | 1/2018 |
| WO | WO 2018002036 | 1/2018 |
| WO | WO 2018005873 | 1/2018 |
| WO | WO 2018013558 | 1/2018 |
| WO | WO 2018013629 A1 | 1/2018 |
| WO | WO 2018013840 | 1/2018 |
| WO | WO2018014174 | 1/2018 |
| WO | WO2018015561 | 1/2018 |
| WO | WO 20180011600 | 1/2018 |
| WO | WO2018018958 | 2/2018 |
| WO | WO2018021920 | 2/2018 |
| WO | WO2018022158 | 2/2018 |
| WO | WO2018022513 | 2/2018 |
| WO | WO2018022619 | 2/2018 |
| WO | WO2018022651 | 2/2018 |
| WO | WO2018022930 | 2/2018 |
| WO | WO2018023114 | 2/2018 |
| WO | WO2018024639 | 2/2018 |
| WO | WO2018026644 | 2/2018 |
| WO | WO2018026941 | 2/2018 |
| WO | WO2018028647 | 2/2018 |
| WO | WO 2018034343 | 2/2018 |
| WO | WO2018034885 | 2/2018 |
| WO | WO 2018035141 | 2/2018 |
| WO | WO 2018035423 | 2/2018 |
| WO | WO20180202691 | 2/2018 |
| WO | WO2018034655 | 3/2018 |
| WO | WO 2018038711 | 3/2018 |
| WO | WO 2018039119 | 3/2018 |
| WO | WO 2018039407 | 3/2018 |
| WO | WO 2018039408 | 3/2018 |
| WO | WO 2018039410 | 3/2018 |
| WO | WO 2018039412 | 3/2018 |
| WO | WO 2018039515 | 3/2018 |
| WO | WO 2018045284 | 3/2018 |
| WO | WO 2018049226 | 3/2018 |
| WO | WO 2018050738 | 3/2018 |
| WO | WO 2018057825 | 3/2018 |
| WO | WO 2018063291 | 4/2018 |
| WO | WO 2018081476 | 5/2018 |
| WO | WO 20180814701 | 5/2018 |

OTHER PUBLICATIONS

Rogers et al., Exploitation of surface acoustic waves to drive size-dependent microparticle concentration within a drop, 2010, Lab Chip, 10, 2979-2985, (Year: 2010).*
Barnkob et al., Acoustic radiation- and streaming-inducted microparticle velocities determined by microparticle image velocimetry in an ultrasound symmetry plane), 2012, Physical Review E, 86, pp. 056307-1 to 056307-11 (Year: 2012).*
Alvarez et al.; Shock Waves, vol. 17, No. 6, pp. 441-447, 2008.
Augustsson et al., Acoustophoretic microfluidic chip for sequential elution of surface bound molecules from beads or cells, Biomicrofluidics, Sep. 2012, 6(3):34115.
Benes et al.; Ultrasonic Separation of Suspended Particles, 2001 IEEE Ultrasonics Symposium; Oct. 7-10, 2001; pp. 649-659; Atlanta, Georgia.
Castilho et al.; Animal Cell Technology: From Biopharmaceuticals to Gene Therapy; 11—Animal Cell Separation; 2008.
Castro; Tunable gap and quantum quench dynamics in bilayer graphene; Jul. 13, 2010; Mathematica Summer School.
Chitale et al.; Understanding the Fluid Dynamics Associated with Macro Scale Ultrasonic Separators; Proceedings of Meetings on Acoustics, May 2015.
Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Grenvall et al.; Concurrent Isolation of Lymphocytes and Granulocytes Using Prefocused Free Flow Acoustophoresis; Analytical Chemistry; vol. 87; pp. 5596-5604; 2015.
Higginson et al.; Tunable optics derived from nonlinear acoustic effects; Journal of Applied Physics; vol. 95; No. 10; pp. 5896-5904; 2004.
Hill et al.; Ultrasonic Particle Manipulation; Microfluidic Technologies for Miniaturized Analysis Systems, Jan. 2007, pp. 359-378.
Ilinskii et al.; Acoustic Radiation Force on a Sphere in Tissue; AIP Conference Proceedings; 2012.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Li et al.; Electromechanical behavior of PZT-brass unimorphs; J. Am. Ceram. Soc. vol. 82; No. 7; pp. 1733-1740, 1999.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; Separation of bacterial spores from flowering water in macro-scale cavities by ultrasonic standing waves; submitted/uploaded to http://arxiv.org/abs/1006.5467 on Jun. 28, 2010.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et al.; An Industrial-Prototype Acoustic Array for Real-Time Emulsion Layer Detection in Oil Storage Tanks; IEEE Sensors Journal, vol. 9, No. 12, Dec. 2009.
Musiak et al.; Design of a Control System for Acoustophoretic Separation, 2013 IEEE 56th International Midwest Symposium on Circuits and Systems (MWSCAS), Aug. 2013, pp. 1120-1123.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Phys. Org. "Engineers develop revolutionary nanotech water desalination membrane." Nov. 6, 2006. http://phys.org/news82047372.html.
Ponomarenko et al.; Density of states and zero Landau level probed through capacitance of graphene; Nature Nanotechnology Letters, Jul. 5, 2009; DOI: 10.1038/NNANO.2009.177.
"Proceedings of the Acoustics 2012 Nantes Conference," Apr. 23-27, 2012, Nantes, France, pp. 278-282.
Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.
Seymour et al, J. Chem. Edu., 1990, 67(9), p. 763, published Sep. 1990.
Volpin et al.; Mesh simplification with smooth surface reconstruction; Computer Aided Design; vol. 30; No. 11; 1998.
Wang et al.; Retention and Viability Characteristics of Mammalian Cells in an Acoustically Driven Polymer Mesh; Biotechnol. Prog. 2004, pp. 384-387 (2004).

(56) References Cited

OTHER PUBLICATIONS

Wicklund et al.; Ultrasonic Manipulation of Single Cells; Methods in Molecular Biology; vol. 853; pp. 1777-196; 2012.
Annex to Form PCT/ISA/206—Communication Relating to the Results of the Partial International Search Report dated Jul. 18, 2013.
European Search Report of European Application No. 11769474.5 dated Sep. 5, 2013.
European Search Report of European Application No. 11796470.0 dated Jan. 5, 2016.
European Search Report of European Application No. 13760840.2, dated Feb. 4, 2016.
European Search Report of European Application No. 13721179.3 dated Mar. 23, 2016.
European Search Report for European Application No. 14749278.9 dated Jan. 13, 2017.
Extended European Search Report for European Application No. EP 12833859.7 dated Mar. 20, 2015.
Extended European Search Report for European Application No. EP 14787587.6 dated Jan. 2, 2017.
International Search Report and Written Opinion for International Application No. PCT/US2011/032181 dated Dec. 20, 2011.
International Search Report and Written Opinion for International Application No. PCT/US2011/040787 dated Feb. 27, 2012.
International Search Report and Written Opinion for International Application No. PCT/US2012/051804 dated Nov. 16, 2012.
International Search Report and Written Opinion for International Application No. PCT/US2013/037404 dated Jun. 21, 2013.
International Search Report and Written Opinion for International Application No. PCT/US2013/032705 dated Jul. 26, 2013.
International Search Report and Written Opinion for International Application No. PCT/US2013/050729 dated Sep. 25, 2013.
International Search Report and Written Opinion for International Application No. PCT/US2013/059640 dated Feb. 18, 2014.
International Search Report and Written Opinion for International Application No. PCT/US2014/015382 dated May 6, 2014.
International Search Report and Written Opinion for International Application No. PCT/US2014/035557 dated Aug. 27, 2014.
International Search Report and Written Opinion for International Application No. PCT/US2014/043930 dated Oct. 22, 2014.
International Search Report and Written Opinion for International Application No. PCT/US2014/046412 dated Oct. 27, 2014.
International Search Report and Written Opinion for International Application No. PCT/US2014/064088 dated Jan. 30, 2015.
International Search Report and Written Opinion for International Application No. PCT/US2015/010595 dated Apr. 15, 2015.
International Search Report and Written Opinion for International Application No. PCT/US2015/019755 dated May 4, 2015.
International Search Report and Written Opinion for International Application No. PCT/US2015/030009 dated Jul. 30, 2015.
International Search Report and Written Opinion for International Application No. PCT/US2015/039125 dated Sep. 30, 2015.
International Search Report and Written Opinion for International Application No. PCT/US2015/053200 dated Dec. 28, 2015.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/031357 dated Jul. 26, 2016.
International Search Report and Written Opinion for International Application No. PCT/US2016/038233 dated Sep. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/044586 dated Oct. 21, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
International Search Report and Written Opinion for International Application No. PCT/US2017/015197 dated Apr. 3, 2017.
International Search Report and Written Opinion for International Application No. PCT/US2017/015450 dated Apr. 10, 2017.
International Search Report and Written Opinion for International Application No. PCT/US2016/047217 dated Apr. 11, 2017.
International Search Report and Written Opinion for International Application No. PCT/US2016/048243 dated Apr. 20, 2017.
International Search Report and Written Opinion for International Application No. PCT/US2017/017788 dated May 8, 2017.
International Search Report and Written Opinion for International Application No. PCT/US2017/030903 dated Jul. 19, 2017.
International Search Report and Written Opinion for International Application No. PCT/US2017/025108 dated Jul. 20, 2017.
International Search Report and Written Opinion for International Application No. PCT/US2017/031425 dated Aug. 30, 2017.
Sony New Release: <http://www.sony.net/SonyInfo/News/Press/201010/10-137E/index.html>.
International Search Report and Written Opinion for International Application No. PCT/US2017/031425 dated Oct. 23, 2017.

* cited by examiner

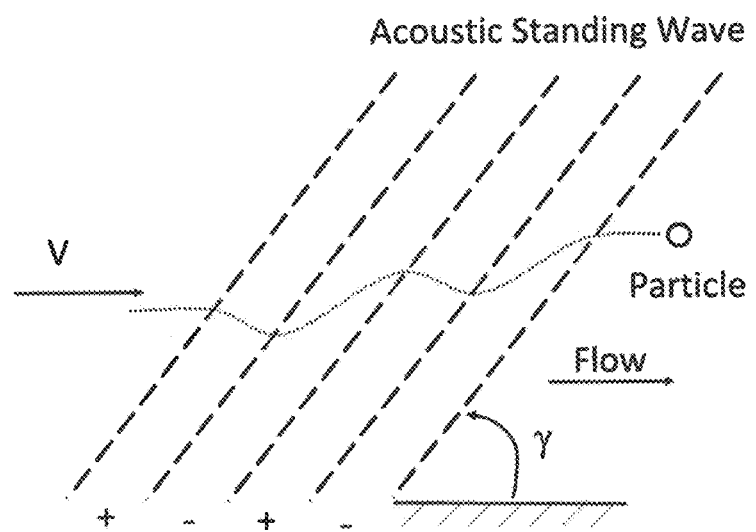
Fig. 1
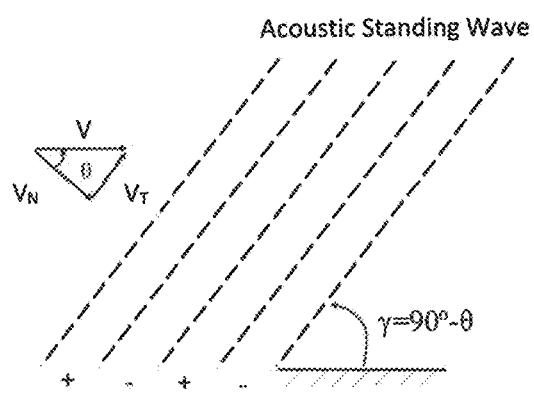 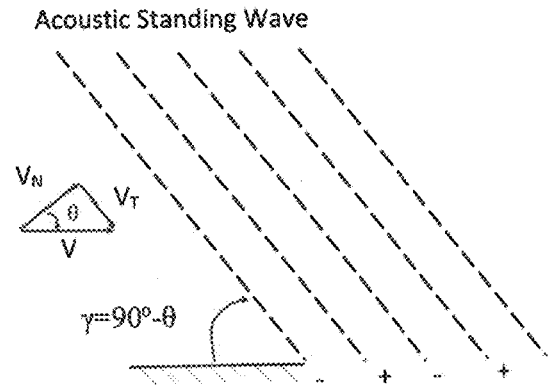
Fig. 2A                                  Fig. 2B

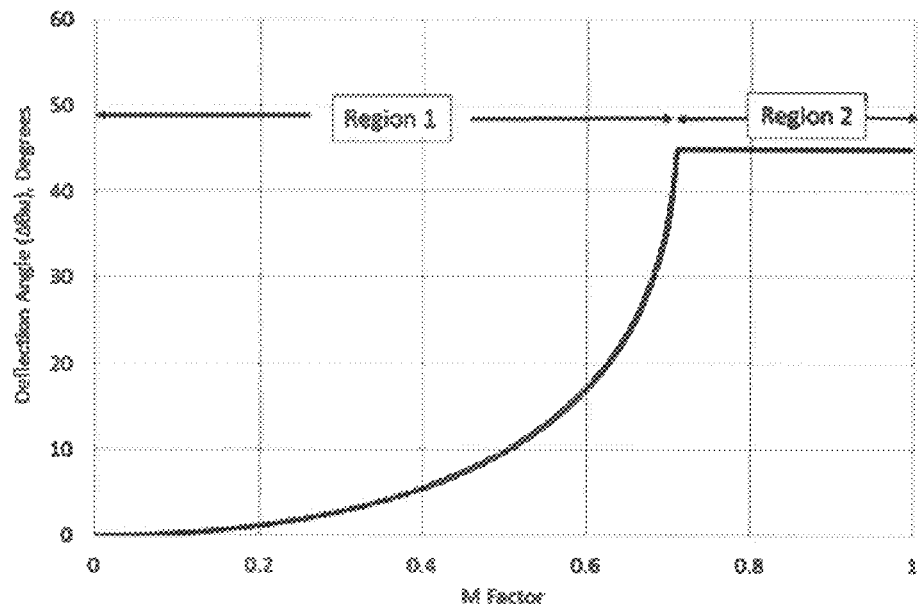
Fig. 7A
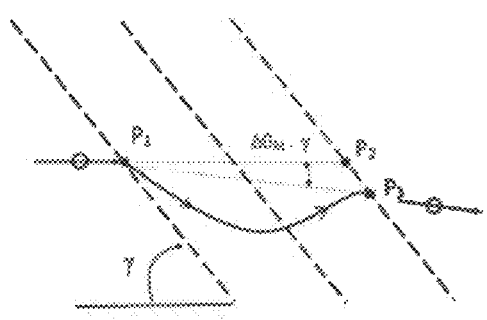     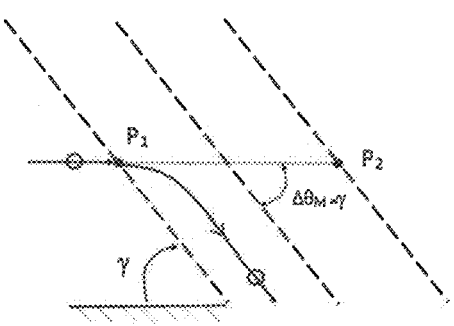
Fig. 7B          Fig. 7C

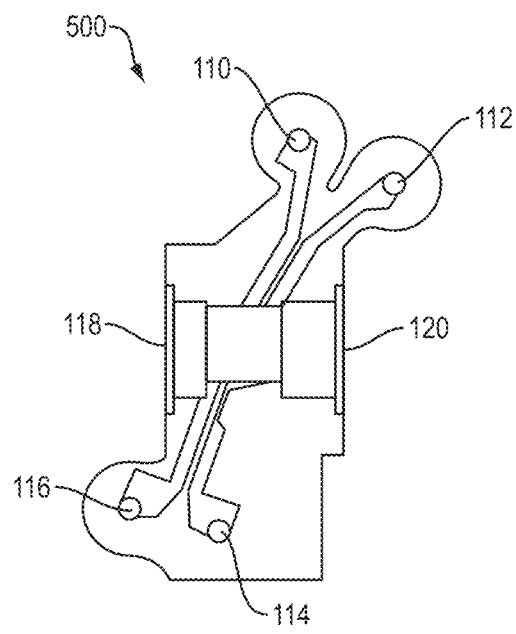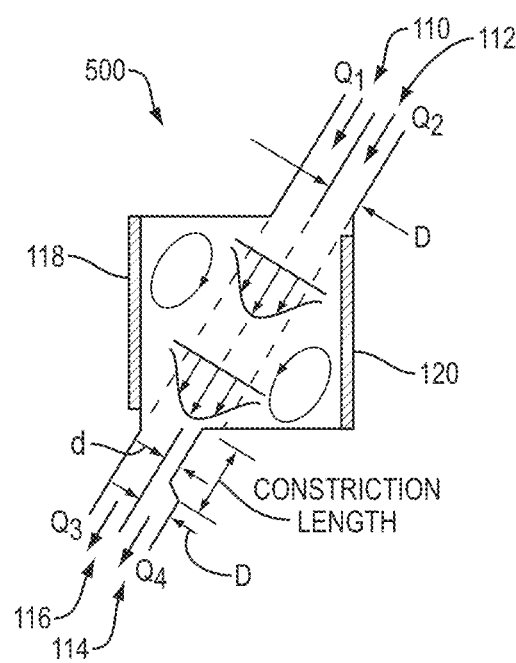
Fig. 20A    Fig. 20B
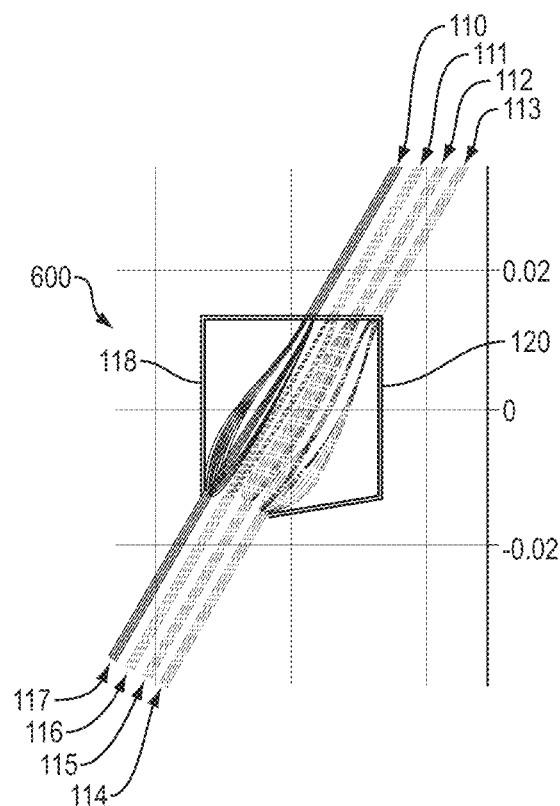
Fig. 21

SEPARATION USING ANGLED ACOUSTIC WAVES

CROSS-REFERENCE TO RELATED APPLICATIONS

This application is a continuation-in-part application of Ser. No. 15/613,790 which is a divisional application of Ser. No. 15/143,481 which claims priority to U.S. Provisional Patent Application Ser. No. 62/316,933, filed on Apr. 1, 2016; and to U.S. Provisional Patent Application Ser. No. 62/154,690, filed on Apr. 29, 2015. This application also claims priority to U.S. Provisional Patent Application Ser. No. 62/479,309, filed on Mar. 30, 2017; and to U.S. Provisional Patent Application Ser. No. 62/485,229, filed on Apr. 13, 2017. All of these applications are incorporated by reference.

BACKGROUND

In the medical field, it often is desirable to separate low concentration cells from a fluid mixture with no harm to the cells, wash cells, concentrate cells in a fluid mixture, differentiate cells based on key parameters, or even fractionate many different types of cells. Such processes are key in the development of possible cures to many common diseases. It may also be desirable to separate particles or cells different in size, density and or acoustic contrast factor using an acoustic field where the particles may be separated from each other as well. Examples include the separation of live from dead cells and the separation of differentiated from undifferentiated cells. The methods described herein provide for such a separation or fractionation method that is label-free.

In the food and beverage industry, filter cartridges and filter membranes have conventionally been used to filter particles from liquids. Such filters are expensive and become clogged and non-functional as material is processed. In contrast, acoustophoresis provides, among other possible advantages, a solid-state, low-cost alternative to filter cartridges and filter membranes that is capable of processing large quantities of a host medium, for example water or beer, that is laden with yeast or other suspended particles.

In the food and beverage industry, host fluid is flowed through filters at flow rates up to ten times greater than those through conventional acoustophoresis devices. At these higher flow rates, trapping of the particles in the host fluid is decreased, thereby leading to decreased separation efficiency. It would therefore be desirable to provide systems and methods capable of separating a second fluid or a particulate from a host fluid at much higher flowrates, or at much lower concentrations, than conventional macro-scale acoustic separators.

In the oil and water industry, efficiently and economically separating oil and other contaminants from water has become an important process. The rise of fracking techniques has led to many settling ponds and large costs for transportation of contaminated water. These settling ponds are a challenge to the environment and better means are needed to clarify fracking water more effectively. Acoustophoresis provides, among other possible advantages, a solid-state, effective means of clarifying fracking, but the flow rates associated with such macro-scale acoustophoresis devices is still too low to be feasible. It would therefore be desirable to provide systems and methods capable of separating a second fluid, cell, or particulate from a host fluid at much higher flowrates.

SUMMARY

This disclosure describes various embodiments of mini to macro-scale systems, devices, and methods for acoustophoresis to separate, fractionate, isolate, concentrate, wash, detect, or even differentiate cells or particles in fluid suspension. The devices and methods include a flow chamber and an ultrasonic transducer and reflector that set up an angled acoustic standing wave oriented at an acute angle relative to the direction of mean flow through the flow chamber, which includes the particle path through the angled acoustic standing wave. At higher flow rates, acoustic standing waves may be used to deflect the particles in a desired direction, without causing the particles to become trapped in the standing wave. By applying the acoustic standing wave to the host fluid at an angle thereto, desired deflection of the particles can be achieved.

These systems and methods can separate, sort, and differentiate various particles using bulk ultrasonic standing waves oriented at an angle $\gamma$ relative to the fluid velocity. This approach offers a sensitive separation capability with respect to size and acoustic contrast of particles.

In one aspect, systems for separating material from a host fluid include: a flow chamber defining a direction of mean flow; an ultrasonic transducer including a piezoelectric material configured to be excited to generate an angled bulk acoustic standing wave with a wavelength and an acoustic radiation force in the flow chamber oriented at an acute angle relative to the direction of mean flow through the flow chamber, wherein the flow chamber has a minimum internal dimension that is at least 10 times the wavelength of the angled acoustic standing wave; a reflector opposite the at least one ultrasonic transducer; a first inlet fluidly connected to the flow chamber; a second inlet fluidly connected to the flow chamber; a first outlet fluidly connected to the flow chamber; and a second outlet fluidly connected to the flow chamber. Embodiments of these systems can include one or more of the following features.

In some embodiments, the first inlet is at least 0.1 inches (e.g., 0.2, 0.3, 0.4, 0.5, or 1 inch) from the angled bulk acoustic standing wave.

In some embodiments, systems also include a first channel ending at the first inlet, wherein the first channel has a substantially straight section extending at least 0.1 inches (e.g., 0.25, 0.5, 0.75, or 1 inch) from the first inlet.

In some embodiments, a space between the ultrasonic transducer and the reflector comprises a first portion within the flow chamber and a second portion outside the flow chamber. In some cases, systems also include an acoustically transparent material separating the first portion from the second portion. In some cases, systems also include a cooling water system in fluid connection with the second portion. In some cases, the second portion is filled with solid material having an acoustic impedance equal to an acoustic impedance of the host fluid.

In some embodiments, the system comprises a plurality of ultrasonic transducers.

In some embodiments, the first inlet and the second inlet are coaxial. In some cases, the first outlet and the second outlet are coaxial. In some cases, the first inlet has a rectangular cross-section. In some cases, an area of the rectangular cross-section of the first inlet is at least 0.05 square inches (e.g., 0.1, 0.25, 0.5, 0.75, or 1 inch).

In some embodiments, the first inlet has an aspect ratio of at least 5 (e.g., 10, 15, 20, 25, or 50).

In some embodiments, systems also include a third outlet, wherein second outlet is disposed between the first outlet and the third outlet and a cross-sectional area of the third outlet is smaller than a cross-sectional area of the second outlet. In some cases, the second outlet has a rectangular cross-section and third outlet has a rectangular cross-section. In some cases, a width of the second outlet is the same as a width of the third outlet. In some cases, a height of the second outlet is at least 2 times a height of the third outlet.

In some embodiments, systems also include a plurality of third outlets, each of the plurality of third outlets offset from an axis of the second outlet in a direction of deflection of the angled acoustic wave.

In some embodiments, systems also include a first channel ending at the first inlet, wherein the first channel has a substantially straight section extending at least 0.1 inches (e.g., 0.25, 0.5, 0.75, or 1 inch) from the first inlet at a first acute angle relative to a plane perpendicular to the angled acoustic standing wave. In some cases, a second channel ending at the second inlet, wherein the second channel has a substantially straight section extending at least 0.1 inches (e.g., 0.25, 0.5, 0.75, or 1 inch) from the second inlet at a second acute angle relative to the plane perpendicular to the angled acoustic standing wave. In some cases, the first acute and the second acute angle are equal. In some cases, system also include a third channel ending at the first outlet, wherein the third channel has a substantially straight section extending from the first outlet at a third acute angle relative to the plane perpendicular to the angled acoustic standing wave. In some cases, the first acute and the third acute angle are equal. In some cases, systems also include a fourth channel ending at the second outlet, wherein the first outlet located in a direction of deflection of the angled acoustic wave relative to the second outlet, wherein the fourth channel has a first cross-sectional area, the third channel has a first section with the first cross-sectional area and a second section with a second cross-sectional area that is smaller than the first cross-sectional area, and the second section of the third channel is located between the first outlet and the first section of the third channel. In some cases, the third channel has a substantially straight section extending from the first outlet at a third acute angle. In some cases, the first acute angle is between 80 degrees and 90 degrees.

In some embodiments, a wall of the flow chamber adjacent to the first outlet in a direction of deflection of the angled acoustic wave extends at an acute angle relative to a plane perpendicular to the angled acoustic standing wave. In some cases, the acute angle is between 1 and 20 degrees (e.g., more than 2 degrees, more than 3 degrees, more than 5 degrees, more than 10 degrees, less than 15 degrees, less than 10 degrees, less than 7.5 degrees, less than 5 degrees).

In one aspect, systems for separating material from a host fluid include: a flow chamber extending between a first end and a second end; an inlet located at the first end of the flow chamber; a first outlet located at between the first end of the flow chamber and the second end of the flow chamber, the inlet and the first outlet defining a direction of mean flow through the flow chamber; an ultrasonic transducer including a piezoelectric material configured to be excited to generate an angled acoustic standing wave between the inlet and the first outlet, the angled acoustic standing wave with a wavelength and an acoustic radiation force in the flow chamber oriented at an acute angle relative to the direction of mean flow through the flow chamber; and a reflector opposite the at least one ultrasonic transducer; wherein the first outlet is spaced apart from the second end of the flow chamber.

In some embodiments, the flow chamber has a minimum internal dimension that is at least 10 times the wavelength of the angled acoustic standing wave.

In some embodiments, the first outlet is located at least 0.5 inches from the second end of the flow chamber.

In some embodiments, the flow chamber has a distance between the first end and the second end and the first outlet is located at away from the second end by at least 30% of the distance. In some cases, the first outlet is located at away from the second end by at most 70% of the distance.

In some embodiments, systems also include a second outlet located at the second end of the chamber.

In one aspect, methods of separating material from a host fluid include: flowing an initial mixture of the host fluid and the material via an inlet into an acoustophoretic device at a flow rate, the acoustophoretic device including: an acoustic chamber communicating with the inlet; an ultrasonic transducer coupled to the chamber and arranged to be excited to produce an acoustic wave at an angle with a mean direction of flow of the initial mixture; controlling a ratio of acoustic radiation force produced by the ultrasonic transducer and a viscous drag force of the initial mixture to cause a first subgroup of the material passing through the acoustic wave to deflect at an angle that is different than that of a second subgroup of the material, to thereby permit the first and second subgroups to be separated. Embodiments of these methods can include one or more of the following features.

In some embodiments, methods also include controlling the ratio by controlling one or more of the angle, the flow rate, a frequency of excitation of the ultrasonic transducer or power supplied to the ultrasonic transducer.

In some embodiments, methods also include controlling the ratio based on characteristics of one or more subgroups. In some cases, methods also include controlling the ratio based on one or more of material size, density, compressibility or acoustic contrast factor.

In some embodiments, methods also include controlling the ratio to deflect at least some of the material at the angle of the acoustic wave.

In some embodiments, the material further includes a third subgroup that is different from the first subgroup and the second subgroup, and controlling the ratio further comprises causing the third subgroup to deflect at an angle that is different than that of the first subgroup or the second subgroup.

In some embodiments, methods also include controlling the ratio in a range that is determined by characteristics of subgroups of materials in the mixture to be separated. In some cases, the range is determined by the relative sizes of the material in the subgroups to be separated. In some cases, the range spans at least an order of magnitude.

In some embodiments, methods also include collecting the first subgroup or the second subgroup in a collection duct communicating with the acoustic chamber.

In some embodiments, the material comprises particulates, cells, or fluids, that include at least two subgroups possessing different characteristics.

These systems and methods can separate, sort, and differentiate various particles using bulk ultrasonic standing waves oriented at an angle $\gamma$ relative to the fluid velocity. This approach offers a sensitive separation capability with respect to size and acoustic contrast of particles.

"Bulk acoustic standing waves" indicate acoustic waves that propagate through volume of a medium such as water with little attenuation. In contrast, "surface acoustic standing waves" are acoustic waves that travel along the surface of a material exhibiting elasticity, with an amplitude that typically decays exponentially with depth into the substrate. Surface acoustic waves do not penetrate very far into a volume of a medium such as water, e.g. several millimeters from a substrate into the water volume at most.

The singular forms "a," "an," and "the" include plural referents unless the context clearly dictates otherwise.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that some of the terms used herein may be relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth. It is to be understood that gravity, or the effects of gravity, are negligible in the angled wave deflection process described herein, because the process works on individual particles, not much larger particle clusters as used in other systems.

The term "parallel" should be construed in its lay sense of two surfaces that maintain a generally constant distance between them, and not in the strict mathematical sense that such surfaces will never intersect when extended to infinity.

Two numbers are of the same order of magnitude if the quotient of the larger number divided by the smaller number is a value of at least 1 and less than 10.

The details of one or more embodiments of these systems, devices, and methods are set forth in the accompanying drawings and the description below. Other features, objects, and advantages will be apparent from the description and drawings, and from the claims.

DESCRIPTION OF DRAWINGS

FIG. 1 is a schematic of particle deflection by the acoustic radiation force of an angled acoustic standing wave oriented at an angle γ relative to the flow velocity V.

FIGS. 2A and 2B are schematics of the normal and tangential velocity components for a left running acoustic standing wave (FIG. 2A), and a right running acoustic standing wave (FIG. 2B).

FIG. 7A is a plot of particle deflection angle $\Delta\theta_M$ versus M parameter curve highlighting two possible regions of particle deflection. FIG. 7B is a schematic of a particle deflection angle $\Delta\theta_M$ at an angle less than the wave angle γ and FIG. 7C is a schematic of a particle deflection angle $\Delta\theta_M$ that equals the wave angle γ.

FIG. 12A is a photograph of the AWD system with multiple flow inlets on the right and multiple flow outlets on the left. FIG. 12B is a schematic of the setup showing locations of the transducer, reflector and flow channels. FIG. 12C is a schematic illustrating one possible mode of operation of the AWD with the dash lines representing the nodal plane locations of the standing wave. FIG. 12D is a schematic of the flow profiles within the AWD. FIG. 12E is a cross-section of the AWD and FIGS. 12F and 12G are cross-sections of alternate duct arrangements for the AWD.

FIG. 17A shows system geometry and flow characteristics.

FIG. 17B shows particle transfer between fluids. FIG. 17C schematically depicts the fluid flow direction of the system.

FIGS. 20A and 20B are, respectively, a cross-section and a schematic of a system in which a flow construction is used to increase the concentration of the particle mixture separated using the system.

FIG. 21 is a schematic of an AFD system designed for particle fractionation.

FIGS. 24A and 24 B are schematics illustrating the anticipated separation of T-cells from beads.

FIG. 25A is a schematic illustrating the anticipated separation of larger beads from smaller beads. FIGS. 25B and 25C are charts of the results.

FIGS. 26A, 26B, and 26C show the distribution of beads between the center outlet and the buffer outlet without acoustics, with 1 W of power applied and with 1.2 W of power applied.

Like reference symbols in the various drawings indicate like elements.

DETAILED DESCRIPTION

Figure 3:
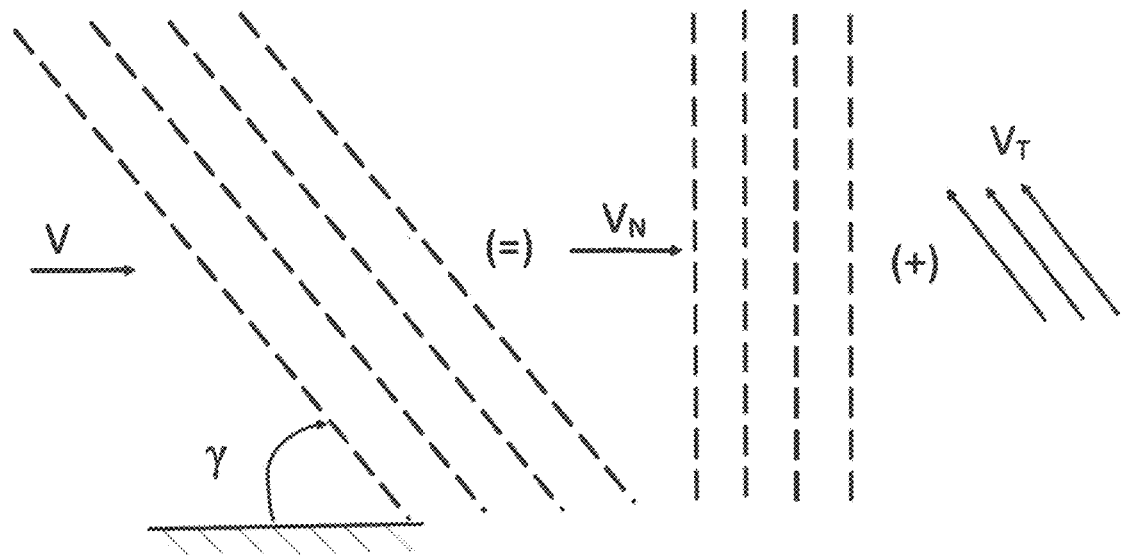
FIG. 3 is a schematic of the Galilean transformation decomposing the angled acoustic standing wave system into a system of two equations, i.e., normal to the wavefront and tangential to the wavefront.

The present disclosure relates to acoustophoretic devices that employ multi-dimensional ultrasonic acoustic standing waves, planar acoustic standing waves or combinations of planar and multidimensional acoustic standing waves (collectively referred to herein as angled acoustic standing waves) oriented at an angle relative to the direction of mean flow through the device. The direction of mean flow through the chamber is to be understood to include the path traveled by a second fluid, cell, or particulate that is flowed through an angled acoustic standing wave generated in the device. These angled acoustic standing waves deflect particles in a host fluid stream, rather than trapping the particles for agglomeration. This is an important distinction from many current acoustophoresis devices. These devices described can operate at high flowrates and can be used to replace costly and clog-prone filter cartridges and filter membranes in various industries. The devices and methods of the present disclosure rely primarily on the axial force component to deflect the particles out of the acoustic field, rather than relying on trapping, agglomeration, and gravitational and buoyancy forces. The devices and methods presented herein are capable of being operated independent of gravity (i.e., in any orientation), and do not rely on gravitational settling. In this way, the axial force of an angled acoustic standing wave oriented at an angle relative to the flow direction is capable of advantageously deflecting material (e.g., a second fluid, cells, beads or other particles, exosomes, viruses, oil droplets) in host fluid streams at high flow rates of up to about 400 mL/min, and more preferably up to about 600 mL/min or about 700 mL/min in devices with a cross section of 1 inch by 1 inch. Devices have also been produced with a 0.5 inch×0.5 inch total flow channel, with the center inlet being 0.1 inch×0.1 inch. For these devices, volumetric flow rates on the order of 0 to 100 ml/min with typical buffer flow rate of 20 to 100 ml/min and center flow rate of 1 to 10 ml/min. This corresponds to linear velocities on the order of 1 to 100 mm/sec regardless of the size of the device.

Thus, bulk acoustic standing waves angled relative to a direction of flow through a device can be used to deflect, collect, differentiate, or fractionate particles or cells from a fluid flowing through the device. The angled acoustic standing waves can be used to separate or fractionate particles in the fluid by size, density, speed of sound, or shape. The angled acoustic standing wave can be a three-dimensional acoustic standing wave. The acoustic standing wave may also be a planar wave where the piezoelectric material is excited in a piston fashion or the acoustic standing waves may be a combination of the planar acoustic standing waves and the multidimensional acoustic standing waves. For the purposes of this disclosure, a standing wave where the lateral force is at least an order of magnitude less than the magnitude of the axial force is considered a "planar acoustic standing wave." However, standing waves that are not planar acoustic standing waves may be used with the approaches described in this disclosure as well. This can be used to separate live cells from dead cells, damaged cells from healthy cells, or differentiated from undifferentiated cells. The deflection of the particles by the standing wave can also be controlled or amplified by the strength of the acoustic field, the angle of the acoustic field, the properties of the fluid, the three dimensionality of the standing wave, the frequency of the standing wave, the acoustic chamber shape, and the mixture flow velocity.

When acoustic standing waves propagate in liquids, the fast oscillations may generate a non-oscillating force on particles suspended in the liquid or on an interface between liquids. This force is known as the acoustic radiation force. The force originates from the non-linearity of the propagating wave. As a result of the non-linearity, the wave is distorted as it propagates and the time-averages are nonzero. By serial expansion (according to perturbation theory), the first non-zero term will be the second-order term, which accounts for the acoustic radiation force. The acoustic radiation force on a particle, or a cell, in a fluid suspension is a function of the difference in radiation pressure on either side of the particle or cell. The physical description of the radiation force is a superposition of the incident wave and a scattered wave, in addition to the effect of the non-rigid particle oscillating with a different speed compared to the surrounding medium thereby radiating a wave. The following equation presents an analytical expression for the acoustic radiation force $F_R$ on a particle, or cell, in a fluid suspension in a standing wave.

$$F_R = \frac{3\pi P_0^2 V_P \beta_f}{2\lambda} X \sin(2kx) \qquad (1)$$

where $\beta_m$ is the speed of sound in the fluid medium, $\rho$ is density, X is acoustic contrast factor, $V_P$ is particle volume, $\lambda$ is wavelength, k is $2\pi/\lambda$, $P_0$ is acoustic pressure amplitude, x is the axial distance along the standing wave (i.e., perpendicular to the wave front), and $$X = \frac{1}{3}\left[\frac{5\rho_p - 2\rho_f}{2\rho_p + \rho_f} - \frac{\beta_\rho}{\beta_f}\right] \qquad (2)$$

where $\rho_p$ is the particle density, $\rho_f$ is the fluid medium density, $\beta_p$ is the compressibility of the particle, and $\beta_f$ is the compressibility of the fluid medium.

The acoustic radiation force on a particle is seen to be a symmetric function having a period that is one half the acoustic wavelength. This means the radiation force distribution repeats every half wavelength. This also means a particle will be accelerated and decelerated by the radiation force presented by Eq. (1).

FIG. 1 schematically shows the particle deflection that such a force variation will generate when a mixture flows through a standing wave at an angle, γ. V is the velocity of the mixture of fluid and particles. The pluses and minuses in the figure represent the direction of the radiation force. Plus sign means the radiation force is in the flow direction and increases particle velocity, and minus sign means the radiation force slows down the particle. The particles will always be deflected toward the wave front, or away from the wave axial direction as shown. FIG. 1 is a left running wave, or the wave slants to the left when looking in the direction of the fluid mixture flow.

FIGS. 2A and 2B are schematics of the normal and tangential velocity components for a left running acoustic standing wave (FIG. 2A), and a right running acoustic standing wave (FIG. 2B). As shown in FIGS. 2A and 2B, the fluid velocity (V) in FIG. 1 can be decomposed into a velocity component perpendicular to the running wave ($V_N$), and one parallel to the wave ($V_T$). The particles will always be deflected in the direction of the tangential velocity component. It is the fluid motion in the tangential direction that carries, or drags the particle at a constant velocity, as the normal velocity component is slowed down or sped up by the axial radiation force. In this case, any particle in suspension will again be deflected in the $V_T$ direction.

An angled flow problem, as presented in FIG. 2 can often be analyzed more simply by using a Galilean transformation, as shown in FIG. 3. This transformation amounts to looking at the same problem while running along the wave at a velocity $V_T$. Theoretically, the physics of the problem do not change with such a transformation. As seen in FIG. 3, this amounts to solving the flow through a standing wave with the flow direction perpendicular to the wave front, or in the axial direction of the wave. In this direction, the acoustic radiation force variation, as presented in Eq. (1), will result in a symmetrical series of velocity increases and decreases in the normal flow direction. Using v as the particle perturbation velocity resulting from the acoustic radiation forces on a particle as the mixture flows through a normal acoustic standing wave, the following governing equation can be generated to describe the particle trajectory (i.e. from Newton's second law, Eq. (1) and Stokes' drag), where $r_p$ is particle radius:

$$\rho_p V_P \left(\frac{dv}{dt}\right) + 6\pi \mu r_p v = \frac{3\pi P_0^2 V_P \beta_f}{2\lambda} X(\beta, \rho) \sin(2kx) \qquad (3)$$

As such, v is actually $\Delta V_N$, or the change in particle velocity normal to the standing wave resulting from the effects of the acoustic radiation forces on the particles as generated by the standing wave relative to the normal fluid flow velocity. The viscosity effects always oppose the perturbation velocity, and act in a direction toward the mean velocity. As a result, the viscosity always drives the particle perturbation velocity to fluctuate about the mean flow velocity with an amplitude of $\Delta V_N$. The particles in suspension are assumed small enough to instantly react to the viscous and radiation forces. With this assumption, the first term on the left side drops out, and Equation 3 can be reduced to:

$$v = C \sin(2kx) \qquad (4)$$

where $$C = \frac{\pi}{3} \frac{r_p^2 \beta_m \varphi}{\mu \lambda} P_0^2,$$

C is the maximum perturbation velocity in the normal direction and is seen to be a function of the acoustic pressure amplitude, particle radius, acoustic contrast factor, fluid viscosity and the acoustic wavelength. With this assumption, the particle velocity instantly adjusts to the Stokes velocity generated by the radiation force.

Figure 4:
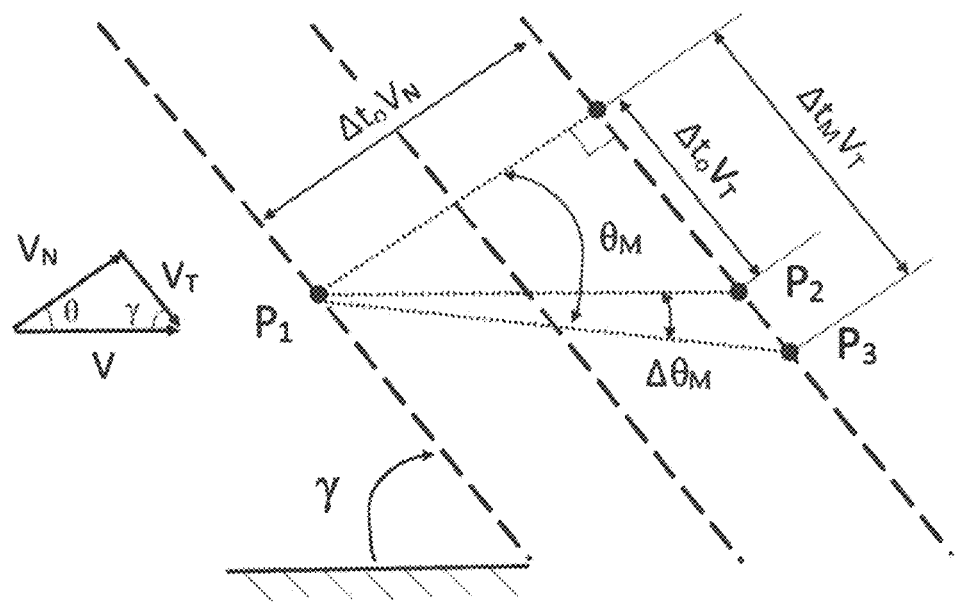
FIG. 4 is a schematic illustration of net particle deflection by the tangential velocity component after a one-half wavelength propagation in the normal direction to the wavefront.

FIG. 4 schematically presents the particle deflection effect caused by the decrease and increase of the velocity component normal to the acoustic standing wave, when the standing wave is at an angle γ to the flow. As inferred by the Galilean transformation, the tangential velocity component has to remain constant as the velocity component normal to the acoustic standing wave varies symmetrically about the mean normal velocity.

The trajectory of the fluid compared to the average trajectory of a particle are also shown in FIG. 4. $P_1P_2$ is the fluid trajectory during a time period $\Delta t_0$. $P_1P_3$ is the average particle trajectory. $V_N$ is the component of velocity perpendicular to the wave, $V_T$ is the tangential component of the velocity along the wave front, V is the incoming mixture velocity, t is time, and $\Delta\theta_M$ is particle deflection from the fluid direction. $P_1$ is where the mixture enters the half wavelength of a standing wave. A planar standing wave is assumed. The fluid is not deflected by the radiation forces and leaves the half wavelength at $P_2$ which is horizontally aligned with $P_1$, in the direction of fluid velocity. On the other hand, the particle is carried down the wave front by the tangential component of the fluid velocity, and is deflected to $P_3$ as seen in the figure. The phrase "a direction of deflection of the angled acoustic wave" is used to indicate the direction of this deflection.

The problem of interest is to determine the particle deflection with acoustic wave angle under different flow and acoustic conditions. $\Delta V_N$ is the maximum normal velocity perturbation, C, associated with a sinusoidal acoustic radiation force acting on a particle as shown in Eq. (4).

Particle or cell deflection can be characterized $\Delta V\_N/V$ which is a non-dimensional parameter that will be defined as M in the following analytical equation development:

$$M = \frac{\Delta V_N}{V} \quad (5)$$

which can be expanded to $$M = \frac{C}{V} = \frac{\pi}{3} \frac{r_p^2 \beta_f P_0^2 X}{\mu \lambda V} \quad (6)$$

where C is the maximum normal velocity perturbation ($\Delta V_N$) from Eq. (4), and V is the fluid free stream velocity. This non-dimensional parameter, M, is important since it represents the ratio of acoustic radiation force on a particle, to the viscous drag force on the particle. M is the key parameter for particle deflection by an angled standing wave. Both acoustic pressure and particle size are squared in the expression. This means they are the most dominant factors for determining particle deflection. An accurate expression for particle deflection in an angled wave, in terms of M, can be obtained by solving particle movement with the normal wave, and then transforming the results to the angled wave flow field (i.e., using the Galilean transformation presented in FIG. 3). The Galilean transformation has no effect on time. Therefore, the time of transit between half wavelengths (which repeat) will be the same in the normal wave plane, and the transformed angled wave plane.

Equation 7 presents an expression for $\Delta t_M$ which is the time it takes a particle in suspension to travel through one half wavelength of the normal standing wave (i.e. process repeats every half wavelength) as it is being accelerated and decelerated by the acoustic axial radiation force. Equation 8 is the expression for $\Delta t_o$ which is the time it takes the fluid to pass through one half wavelength of the normal wave. These two time values are independent of the Galilean transformation, and combined with FIG. 4, can be used to obtain particle deflection from the fluid flow direction $$\Delta t_M = \int_0^{\lambda/2} \frac{dx}{V_N + \Delta V_N \sin 2kx} = \frac{1}{V_N} \int_0^{\lambda/2} \frac{dx}{1 + \frac{M}{\sin \lambda} \sin 2kx} \quad (7)$$

$$\Delta t_o = \frac{\lambda/2}{V_N} \quad (8)$$

The ratio of these times is defined as $$\varepsilon = \frac{\Delta t_M}{\Delta t_o} \quad (9)$$

Equations 10 and 11 use $\varepsilon$ combined with the wave angle $\gamma$ to generate an expression for particle deflection in the angled wave field.

$$\tan \theta_M = \frac{\Delta t_M V_T}{\Delta t_o V_N} = \frac{\varepsilon}{\tan \gamma} \quad (10)$$

$$\Delta \theta_M = \tan^{-1}\left(\frac{\varepsilon}{\tan \gamma}\right) - \frac{\pi}{2} + \gamma \quad (11)$$

FIG. 4 helps interpret Eq. (10) and (11). The angled waves in FIG. 4 represent the results of transforming the normal wave by adding $V_T$ to all the velocities. $P_1$ is the point that the flow mixture enters the standing wave. The standing wave is at an angle $\gamma$ with respect to the flow direction. The dash wave lines represent regions in the standing wave where the radiation forces on the particles are zero. The direction of the radiation forces reverse when crossing the dash lines shown in FIG. 4. $P_2$ and $P_3$ are points on the zero force line that is $\lambda/2$ distance away from $P_1$. The particle in suspension when flowing through $P_1$ will be deflected by the acoustic wave and will pass through $P_3$ as shown in FIG. 4. $P_2$ is the point it would have passed through with no acoustic radiation forces, and it represents the fluid flow direction. The dashed line connecting $P_1$ and $P_3$ represents the average trajectory of the particle through one cycle of the acoustic radiation force. $\theta_M$ is the total angle that the same line makes with the normal direction of the wave. Therefore, $\Delta \theta_M$ is the particle deflection angle generated by the acoustic wave as measured from the flow direction (i.e. dash line connecting $P_1$ and $P_2$). The particle transit times calculated from the normal wave analysis are used with the tangential velocity transformation to get particle displacements in the wave front direction. The particle wave front distance generated by the transformation with no radiation forces is $\Delta t_o V_T$ and the particle wave front distance generated by both the Galilean transformation and the integrated effects of acoustic radiation forces on the movement is $\Delta t_M V_T$. The difference ($\Delta t_o V_T - \Delta t_M V_T$) is the particle deflection along the wave front direction generated by the sinusoidal acoustic radiation forces acting on the particle. For $\Delta \theta_M$, or particle deflection angles, to be calculated at different wave angles and different deflection parameters, M, the integral expression for epsilon has to be solved in Eq. (11).

An analytical solution for particle deflection as a function of wave angle and the non-dimensional parameter, M, defined by the ratio of acoustic radiation forces and viscous forces on a mixture flowing through an acoustic standing wave, was developed using substitution of variables. This analytical solution which allows particle deflection angle to be predicted for all values of M and $\gamma$, is shown in Eq. (12).

$$\Delta \theta_M = \begin{cases} \tan^{-1}\left(\cfrac{1}{\tan\gamma \sqrt{1 - \left(\frac{M}{\sin\gamma}\right)^2}}\right) - \frac{\pi}{2} + \gamma & \text{if } \frac{M}{\sin\gamma} < 1 \\ \gamma & \text{if } \frac{M}{\sin\gamma} \geq 1 \end{cases} \quad (12)$$

Figure 5:
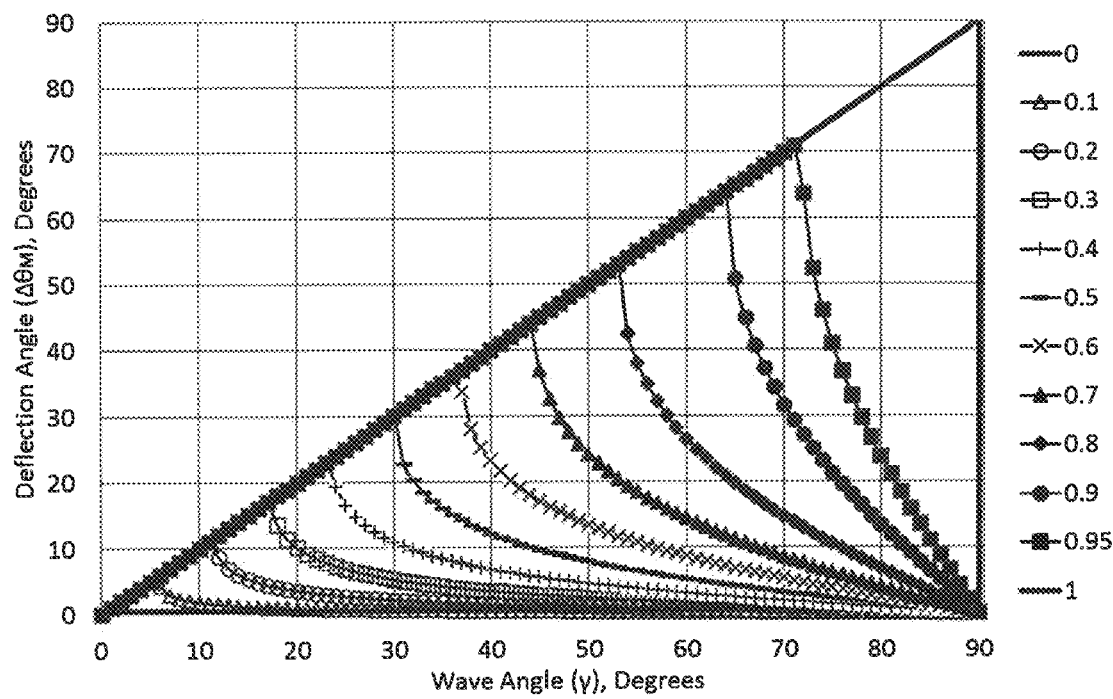
FIG. 5 is a plot of particle deflection angle $\Delta\theta_M$ versus wave angle γ for M parameter values of 0 to 1.

FIG. 5 presents calculated particle deflection angles from Eq. (12) as a function of the wave angle γ, and the non-dimensional deflection parameter M. The different M curves in FIG. 5 can represent the effects of power on particle deflection versus wave angle while particle size, fluid compressibility factor, acoustic wavelength, fluid viscosity and fluid velocity are all held constant at a baseline condition. The wave angle variation is from zero to ninety degrees. The particle deflection, at any constant M value, starts at zero where the wave angle is zero and moves up along the forty-five° line until a maximum is reached. Increasing wave angle, with M fixed, increases the component of the radiation force slowing down the particles. At some wave angle condition, the particles are stopped from moving through the waves by the normal radiation force, and are forced by the fluid to move along the wave front direction. At this point, the particle deflection reaches a maximum for that M value (i.e. M=0.667, at a wave angle of 42 degrees is an example).

The triangular solution region under the 45° line shown in FIG. 5 represents all particle deflections possible with a mixture flowing at an angle relative to the bulk acoustic standing waves. It can be applied to any fluid, standing wave, particle or acoustic pressure. It presents particle deflection at all wave angles as a function of a non-dimensional parameter, M, which is the ratio of acoustic radiation force to viscous drag force on the particle. Deflection angles are seen to either fall on, or lie below the 45° line as shown in FIG. 5. The forty-five degree line represents the case where the deflection angle $\Delta\theta_M$ and acoustic wave angle γ are equal. This is the maximum particle deflection for any angled acoustic wave and occurs when M/sin γ≥1, i.e., the acoustic radiation force equals or exceeds the viscous drag force. This analytical solution enables angled wave systems to designed and controlled to provide the M values necessary to obtain desired results as discussed in more detail later in this disclosure.

Each M curve in FIG. 5 is seen to have a steep gradient near the maximum deflection value where the particle deflection shifts from the difference between the up and down deflection regions shown in FIG. 1 for a left running wave, to the up deflection only. This steep gradient represents a change in the physical mode of the deflection process and is reflected in the experimental results presented later in this disclosure. This occurs when the radiation force in the upward deflection region reaches a value large enough to stop the particle motion through the wave. The results show that particles flowing in a fluid suspension can be deflected along an acoustic standing wave of any strength, if the wave angle is small enough. The different M curves in FIG. 5 can represent the effects of acoustic pressure on particle deflection versus wave angle while particle size, fluid compressibility factor, acoustic wavelength, fluid viscosity and fluid velocity are all held constant at the baseline condition.

For example, the M=0.8 curve in the figure can represent many different applications. One exemplary application with M=0.8 has a fluid mixture velocity, V=7.75×10$^{-4}$ m/sec, an acoustic standing wave wavelength, λ=7.4×10$^{-4}$ m, a mixture viscosity, μ=1.0×10$^{-3}$ Pa·s, a contrast factor, X=0.12, a mixture compressibility, $\beta_f$=4.06×10−10 m2/N, particle radius, $r_p$=3×10$^{-6}$ m, and acoustic pressure amplitude, $P_0$=1.0 MPa as a discussion point. The particle deflection curve presented in FIG. 5 for various M parameters is for all wave angles. Looking at this curve as wave angles are varied from zero to ninety degrees helps interpret the physics. The particle deflection initially moves up the 45° line. Along this line, the particle is stopped between waves, and moves tangentially along the wave front. This effect continues with increasing wave angles until the axial radiation force can no longer stop the normal velocity component of the particle. At this point, the particle moves through multiple waves and is deflected by each wave it passes through. The particle deflection is a maximum of 53°, for M=0.8, at a wave angle of 53°. At a wave angle of 55° with M=0.8, the particle deflection angle drops to 38° and at a wave angle of 60° with M=0.8, the particle deflection is 26.5°.

Figure 6:
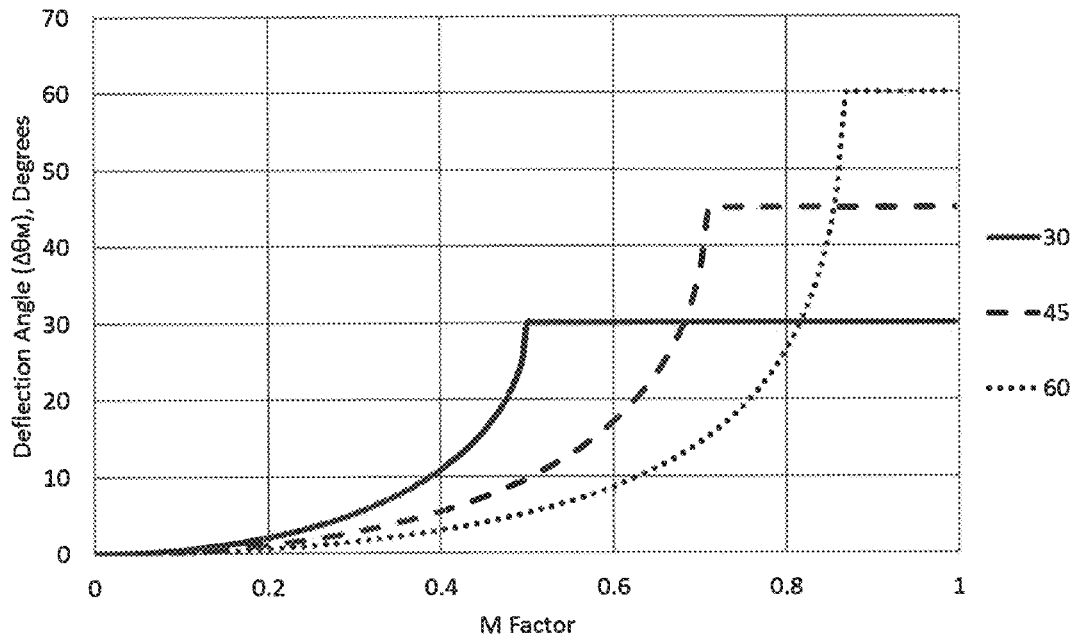
FIG. 6 is a plot of particle deflection angle $\Delta\theta_M$ versus M parameter for acoustic standing wave angles of 30°, 45°, and 60°.

FIG. 6 presents the particle deflection variation with M that occurs through waves angled at 30°, 45°, and 60°. M is varied from 0 to 1 in FIG. 6. The particle deflection angle $\Delta\theta_M$ increases with increasing values of M. The rate of increase of particle deflection angle also grows with increasing values of M. A steep gradient in the deflection curve is observed near the maximum deflection angle for all curves. The magnitude of the gradient is seen to increase with increasing wave angle γ. This steep gradient provides a mechanism for the separation of particles with only slight differences in acoustic properties.

FIGS. 7A, 7B, and 7C present the particle deflection curve versus M for an acoustic wave angle of 45° only. In region 1, the particles pass through all the waves, and get deflected down (for the right running wave shown) at a constant angle, $\Delta\theta_M$ smaller than γ as shown in FIG. 7B. The particle net deflection in region 1 is the difference between downward deflection (particle slowed down by the radiation force) and upward deflection (particle accelerated by the radiation force). The curve in FIG. 7A shows the large gradient that occurs when region 1 transitions into region 2. In the vicinity of this transition, a small change in M generates a large change in particle deflection angle $\Delta\theta_M$. The separation of particles with minute size, stiffness or density differences may be accomplished in this transition region. Region 2 presents the operating parameter space where the acoustic radiation force is large enough to stop the particles from moving through the waves. The particles move parallel to the wave front and $\Delta\theta_M$=γ in region 2. Theoretically, in region 2, all the particles will be deflected down the wave front in the first wave as shown in FIG. 7C.

The analytical model results, as presented in FIG. 5, predict that particles in suspension can be deflected down an acoustic standing wave of any strength, if the wave angle is small enough. As the wave angle γ is decreased, the fluid and particle velocity normal to the wave decreases. At some point, the acoustic radiation force will overcome the oncoming particle normal velocity component, and as a result, the particle will stop moving through the wave and will travel along the wave front. This process occurs when the wave angle is low enough to cause the resultant particle velocity component normal to the wave to reach zero. The forty-five degree line in FIG. 5 represents a locus of such points. The analysis predicts the maximum deflection for any value of M always falls on this forty-five degree locus line. Since the acoustic power parameter M is equal to C/V where C represents the maximum particle normal velocity perturbation generated by the acoustic radiation forces, it also can be interpreted as the ΔVN/V where V is the oncoming fluid and particle velocity. When ΔVN=V sin(γ), the acoustic perturbation velocity is equal to the fluid normal velocity component to the wave. Therefore, at any power, or acoustic pressure of the acoustic standing wave, there will be an angle of the standing wave where the radiation force can stop the particle velocity normal to the wave. The following equation defines this point which represents the maximum particle deflection as well as where the deflection curve for a given M value intersects the forty five degree line in FIG. 5:

$$\Delta\theta_{max}=\sin^{-1}(M)=\gamma \qquad (13)$$

Equation 13 defines the maximum deflection angle possible, and the wave angle γ needed for maximum particle deflection using angled acoustic standing waves as a function of the non-dimensional parameter M.

The M parameter can also be used to determine the desired operation characteristics, for example, to be used in deflecting extremely small particles in suspension. The smaller the particle size, the lower the M factor. Assuming flow velocity is reduced as low as possible for system feasibility, and power is increased as large as possible, then the M operating curves specify that the system should be operated at as low a wave angle as possible as particle deflection peaks at lower wave angles for low M values. This indicates that systems used with small particles, or nanoparticles, should be operated at extremely small angles (e.g., <5°, <4°, <3°, <2°, <1°).

The predictions presented above are based on analytical procedures for ideal standing waves and fluid velocity fields, and were used as guidance for more accurate numerical particle trajectory studies and experimental verification tests showing the benefits of using acoustic standing waves to deflect, collect, differentiate, separate, purify, or fractionate one population of particles or cells from a mixture that may contain multiple different types of particles, i.e., different in size and/or material properties such as density or compressibility.

The particle trajectory can be solved by numerically integrating the equation of motion of the particle, i.e., Eq. (3) given some initial conditions of the particle. The equation is solved by a fourth order Runge Kutta method with automatic time stepping. In the following results, a uniform velocity profile of fluid for a flow channel of one inch width is used. Typical conditions used in the computations are an acoustic standing wave with a frequency of 2 MHz and an acoustic pressure amplitude of 1 MPa. The acoustic standing wave has a width of one inch and has an angle of 45°.

Figure 8A:
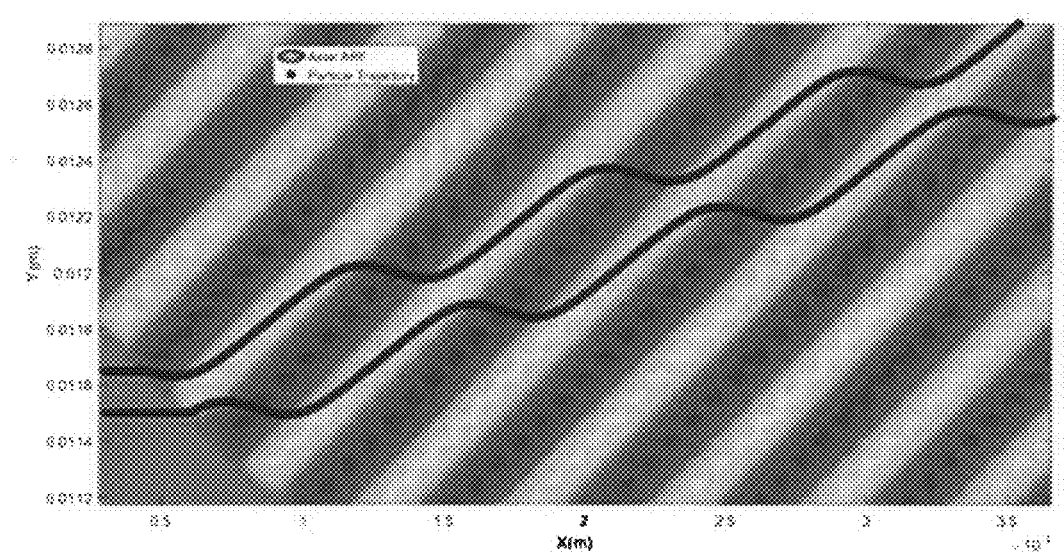
FIGS. 8A and 8B show the numerical particle deflection trajectory for a CHO cell for (a) M/sin λ value less than one and (b) M/sin λ value greater than one for a frequency of 2 MHz, an acoustic pressure amplitude of 1 MPa, a particle diameter of 18 μm, and an acoustic contrast factor of 0.03.
Figure 8B:
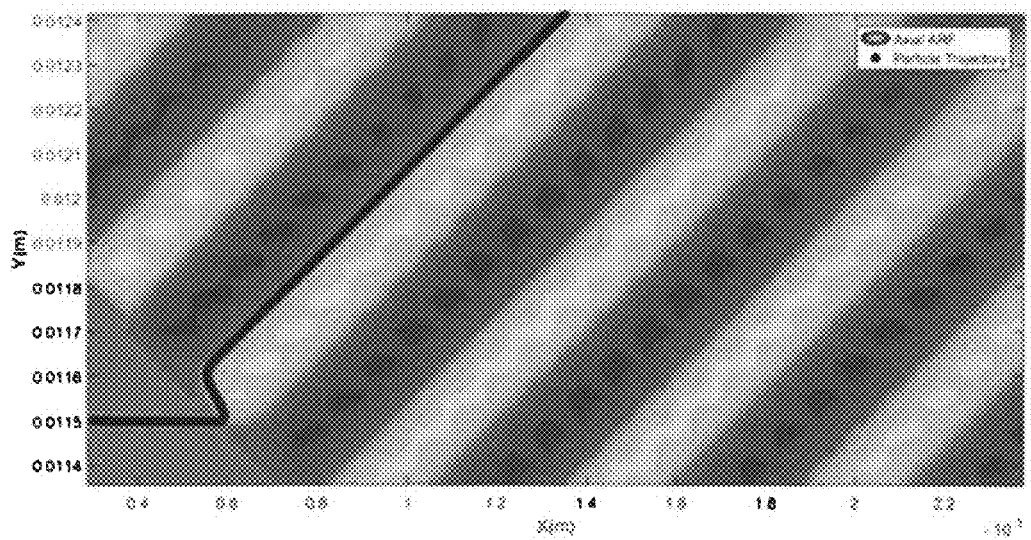

FIGS. 8A and 8B presents deflection results for a particle with properties that are similar to a Chinese Hamster Ovary (CHO) cell. CHO cells are of interest since they are widely used in the production of recombinant proteins and monoclonal antibodies. A typical CHO cell has a diameter of 18 µm and an acoustic contrast factor of 0.03.

FIGS. 8A and 8B show the numerical particle deflection trajectory for a CHO cell for M/sin γ value less than one and for M/sin γ value greater than one, respectively. The simulation used: a frequency of 2 MHz, an acoustic pressure amplitude of 1 MPa, a CHO cell diameter of 18 µm, and a CHO cell acoustic contrast factor of 0.03. The numerical particle trajectory results further verify the physics of angled standing waves and the analytical predictions presented for two cases, M/sin γ<1 and M/sin γ≥1. These results include inertial effects. Viscosity modifies inertial effects to generate a symmetrical perturbation velocity about the mean normal velocity component which generates the net constant deflection as shown in FIGS. 8A and 8B. Therefore, the particle deflection in the first half wavelengths can vary depending on the exact location of the particle relative to the standing wave, as is shown in FIG. 8 where the initial particle location of the two particles differs by a quarter wavelength in the y direction. The viscosity damps this initial length effect out quickly. The results verify the constant angle of deflection as the particle passes through each half wavelength of the standing wave. When M/sin γ≥1 (i.e., the condition in FIG. 8B), the particle deflection angle equals the standing wave angle. After the initial transient of the particle motion, the particle deflection is along the wave angle.

Figure 9A:
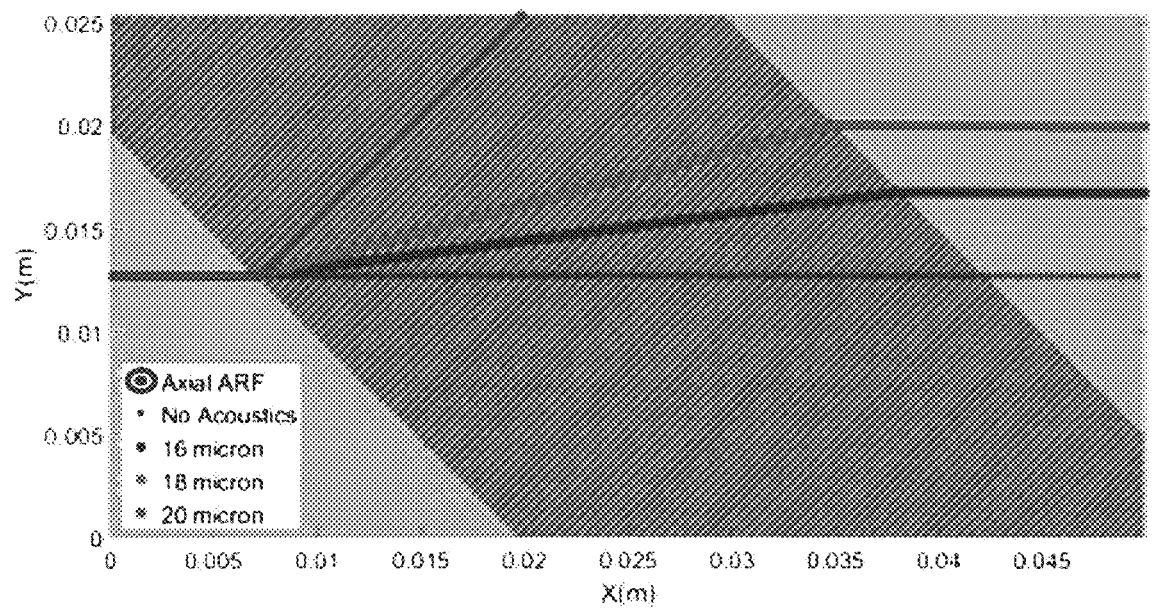
FIG. 9A shows the numerical particle deflection trajectory for CHO cells of diameter 16, 18, and 20 μm and acoustic contrast factor of 0.03.
Figure 9B:
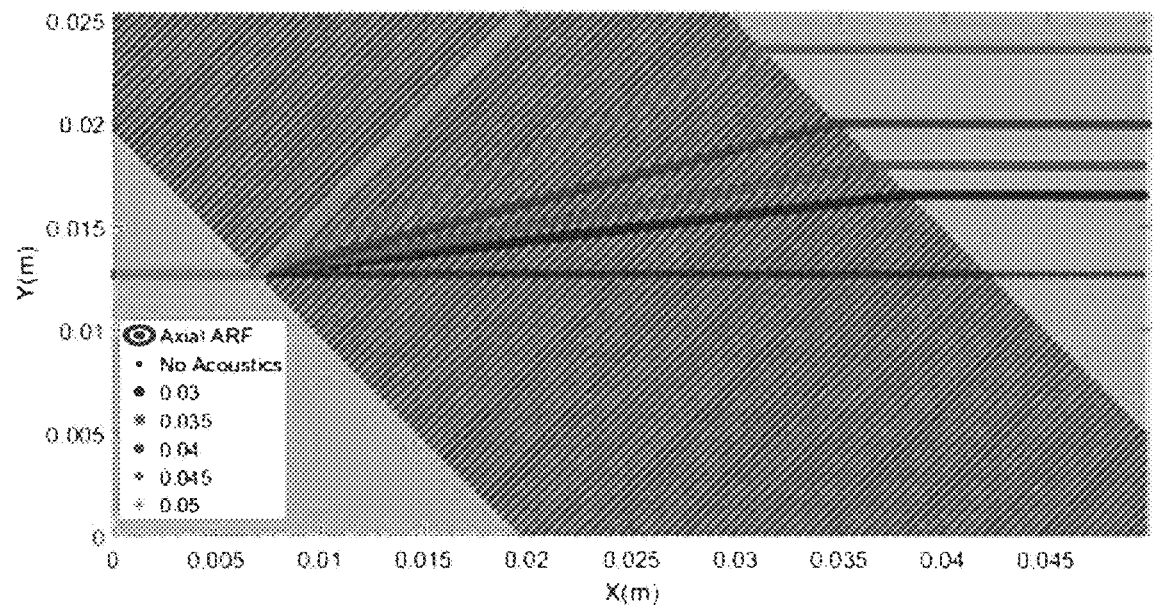
FIG. 9B shows the numerical particle deflection trajectory for CHO cells of diameter 20 μm and acoustic contrast factors of 0.03, 0.035, 0.04, 0.045, and 0.05. Frequency is 2 MHz, acoustic pressure amplitude is 1 MPa and velocity amplitude is 6 cm/min.

FIG. 9A shows numerical particle trajectory for CHO cells of diameter 16, 18, and 20 µm and acoustic contrast factor of 0.03. FIG. 9B shows the numerical particle trajectory for CHO cells of diameter 20 µm and acoustic contrast factors of 0.03, 0.035, 0.04, 0.045, and 0.05. The simulation used a frequency of 2 MHz, an acoustic pressure amplitude of 1 MPa, and a velocity amplitude is 6 cm/min.

FIG. 9A shows CHO particle deflections for three slightly different sizes, 16, 18, and 20 µm, representing a size variation of about ±10%. The smallest particle deflection is that of a particle with an M/sin γ value less than one. The 18 µm particle deflects according to an M/sin γ value of less than one but greater than that of the 16 µm particle, resulting in a larger deflection. The 20 µm particles deflection is that of an M/sin γ>1 type trajectory. These small size differences lead to large differences in particle trajectories. FIG. 9B shows similar results but as a function of small changes in acoustic contrast factor, i.e., values of 0.03, 0.035, 0.04, 0.045, and 0.05. These results indicate that angled standing waves can be used to separate, or fractionate particles in suspension by size, acoustic contrast factor, i.e., density and compressibility, and shape. This technique may allow live cells to be separated from dead cells, or even damaged cells from healthy cells. For example, Table 1 presents the acoustic contrast factors for several types of cells.

TABLE 1

| Cell Type | Density (g/cc) | Speed of Sound (m/s) | Acoustic Contrast Factor |
|---|---|---|---|
| Jurkat T-cell | 1.06 | 1615 | 0.079 |
| Primary T-cell | 1.04 | 1560 | 0.049 |
| Yeast | 1.1 | 1700 | 0.12 |
| CHO | 1.03 | 1550 | 0.03 |

Figure 10:
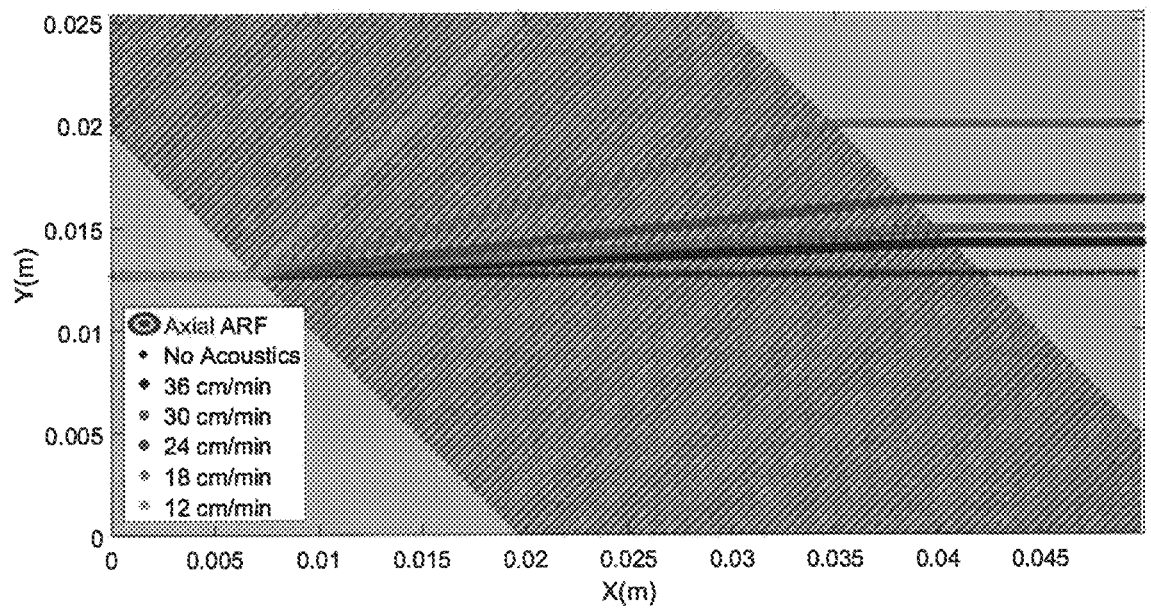
FIG. 10 shows numerical particle trajectories for a CHO cell as a function of velocity magnitude of the fluid through the channel.

FIG. 10 shows numerical particle trajectories for a CHO cell as a function of velocity magnitude of the fluid through the channel. These particle trajectories verify the effects of normal velocity variation on the particle deflection resulting from a mixture flowing into an acoustic standing wave at an angle of 45°. As the flow velocity increases, A $V_N/V$ decreases and particle deflection angles. This effect provides a means to increase the ability to detect minor differences in particle properties by manipulating the fluid velocity. The deflection of the particle by the standing wave can also be controlled and/or amplified by the strength of the acoustic field, the angle of the acoustic field, the properties of the fluid, the three dimensionality of the standing wave, the frequency of the standing wave, the acoustic chamber shape and the mixture flow velocity.

Figure 11A:
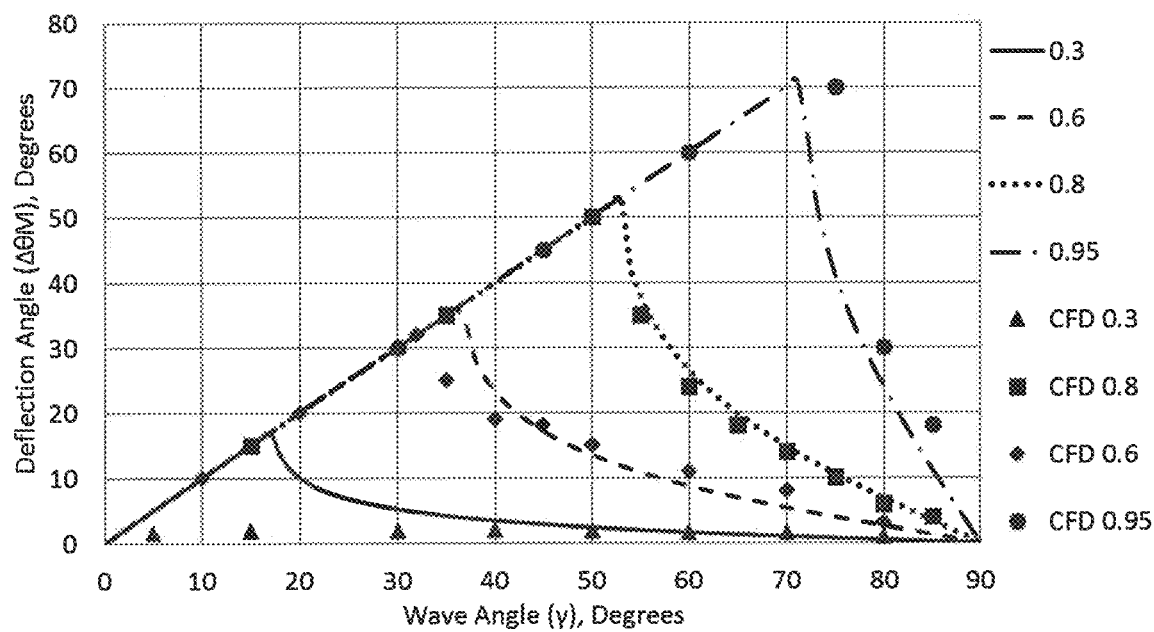
FIG. 11A is a chart comparing the universal analytical predictions for particle deflection with numerical particle trajectories over a wide range of M values.

FIG. 11A compares the universal analytical predictions for particle deflection, with numerical particle trajectories over a wide range of M values. The different lines in the figure represent analytical predictions from FIG. 5. The symbols represent numerical data from CFD. Each line or symbol type represents a different M value in FIG. 11. The agreement between analytical predictions and numerical results are good. The errors seen in narrow regions near wave angles of 0°, and 90° are believed to be a result of singularities that occur at these two extremes. The results verify the importance of the deflection parameter M, the location of the maximum deflection, and the existence of a steep gradient region near the maximum deflection point.

Figure 11B:
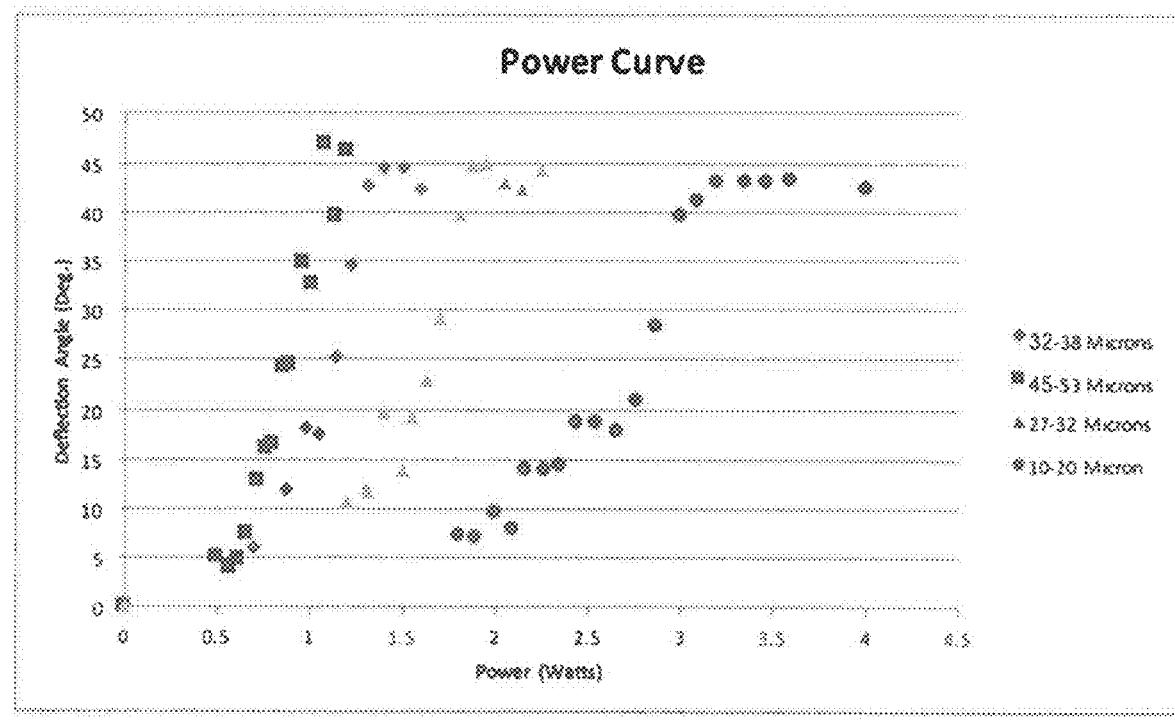
FIGS. 11B and 11C are charts comparing the universal analytical predictions for particle deflection, with numerical particle trajectories over a wide range of M values
Figure 11C:
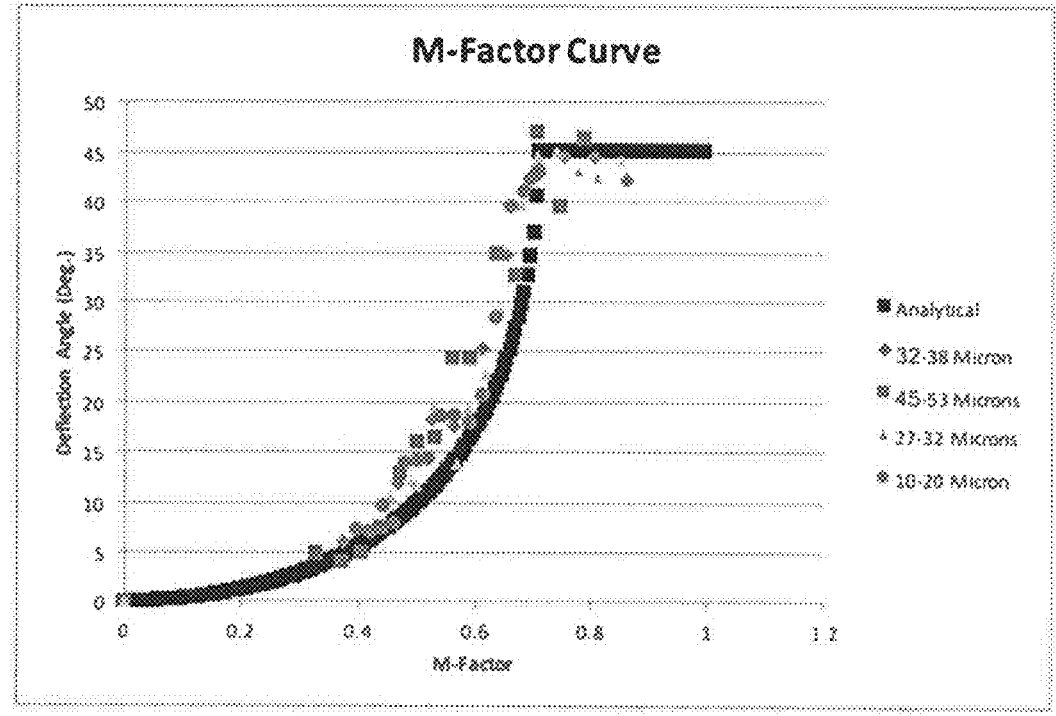

FIGS. 11B and 11C present the results of an experiment with an angled wave device that has two outer channels adjacent to a central channel and a wave angle of 45 degrees. The device was operated at a frequency of 2.1 MHz and a flow rate of 2 ml/min in the central channel and 40 ml/min in the outer channels. The outer channels contained clear or buffer fluid, and the central channel was provided with a fluid containing beads of a given size. The power was varied and the deflection angle of the beads versus power was measured and plotted for each of four different groups of beads in FIG. 11B. In addition, as the power was varied, the deflection angle of the beads versus the M factor was measured and plotted for each of four different groups of beads in FIG. 11C. Each of the four different groups of beads had bead sizes falling in a range of sizes that was different for each group of beads. The group denoted with circle shapes in the graph is sized in the range of 10-20 micrometers. The group denoted with triangle shapes in the graph is sized in the range of 27-32 micrometers. The group denoted with diamond shapes in the graph is sized in the range of 32-38 micrometers. The group denoted with square shapes in the graph is sized in the range of 45-53 micrometers. As shown in FIG. 11B, the deflection angle for the beads changed with the change in power. As shown in FIG. 11C, the M factor for all the beads agrees fairly well with the analytical result shown in solid black squares.

The numerical particle trajectory model can easily be modified to take into account more realistic acoustic and flow fields. Computational Fluid Dynamics simulations can be done to determine the fluid velocities in a realistic fluid channel geometry. Similarly, numerical solvers for acoustic fields generated by piezoelectric transducers can be used to predict more accurate solutions for the acoustic field. The particle trajectory model can then make use of the numerically predicted acoustic and fluid velocity fields to obtain more realistic predictions. Another extension is the inclusion of gravitational and buoyancy forces acting on the particles.

Two macroscale, ultrasonic, angled wave separator configurations were fabricated and tested. Two different approaches were used to generate the desired fluid/acoustic interactions. The first concept is that of an Angled Wave Device (AWD) where an angled acoustic standing wave propagates through one or more parallel fluid streams flowing in a straight duct. The second is an Angled Fluid Device (AFD) where narrow fluid streams are injected and controlled to flow through an acoustic standing wave chamber at an angle to the standing wave. These macro scale, ultrasonic separators were shown to have the potential to operate effectively at much higher flow rates and/or at much lower particle concentrations, than conventional acoustic separators. For example, while earlier acoustic separators typically operate a linear velocity of less than 1 mm/s, the systems described in this disclosure can operate at linear velocities of up to 100 mm/s. The test results verified the analytical predictions, and demonstrated the potential to separate, or fractionate particles in suspension by size, density, and speed of sound using angled acoustic standing waves.

Figure 12A:
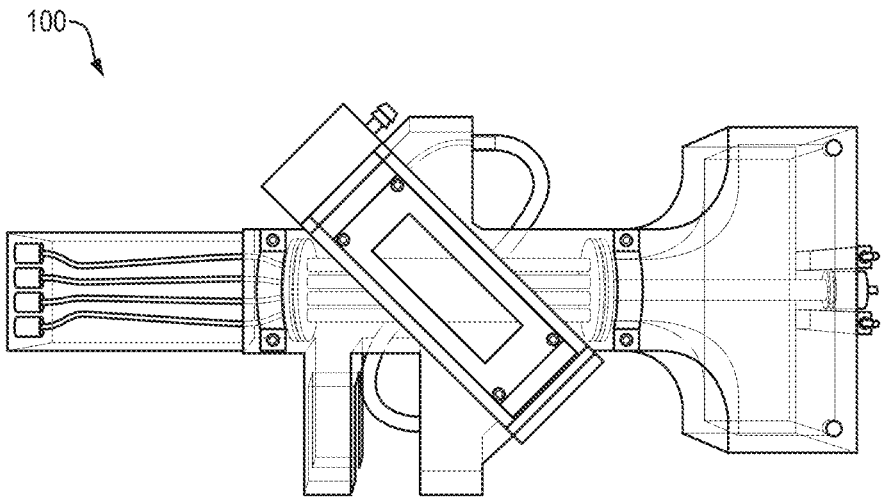
FIG. 12A-12G show an angled wave device (AWD) system with a 45° angled standing wave.
Figure 12B:
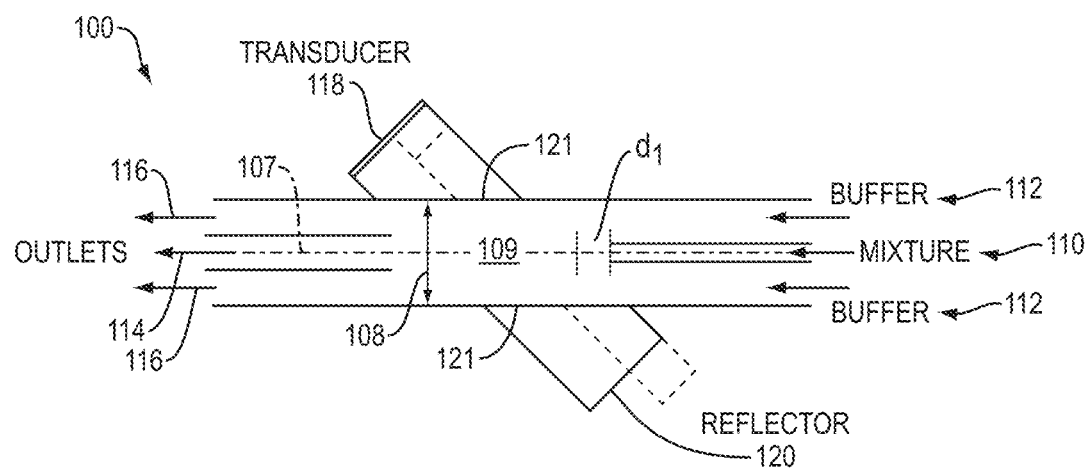
Figure 12C:
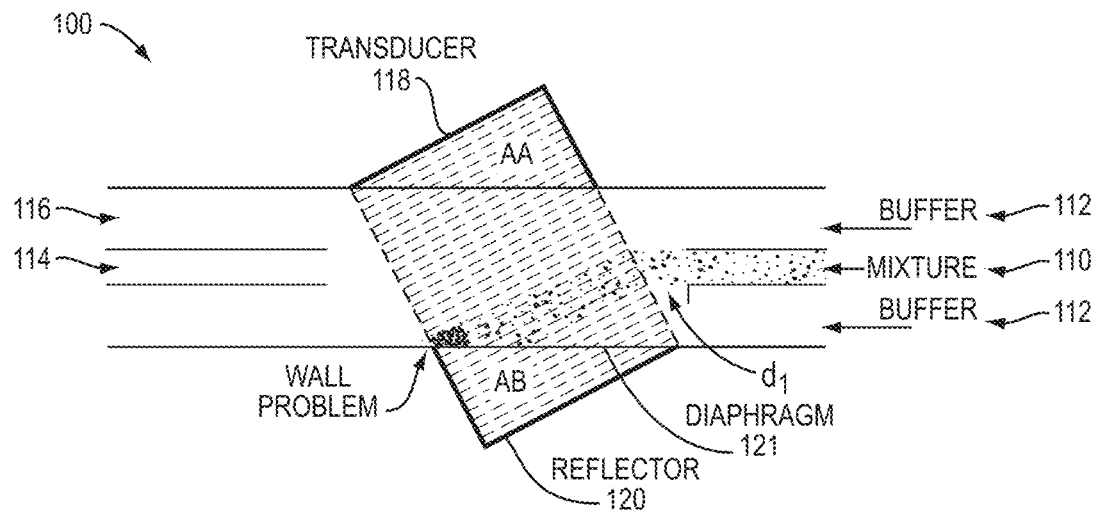
Figure 12D:
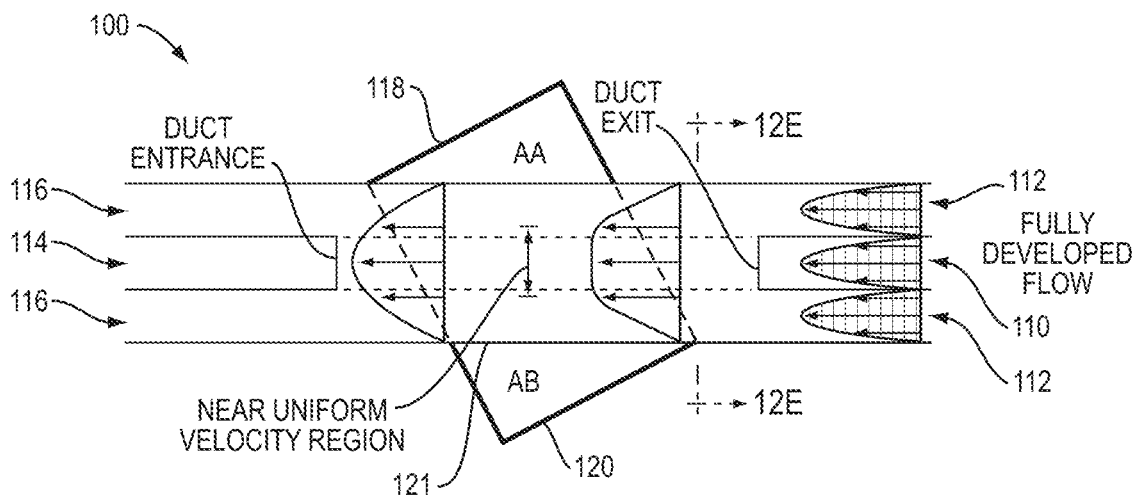
Figures 12E, 12F, 12G:
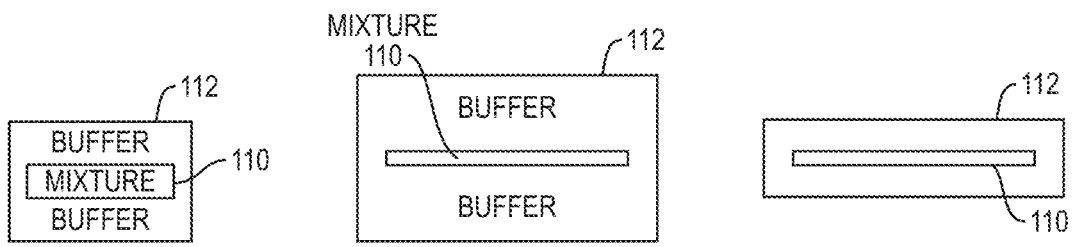

FIGS. 12A, 12B, and 12C show an AWD system 100 with a 45° angled standing wave. FIG. 12A is a photograph of the AWD system 100 with multiple flow inlets 110, 112 on the right and multiple flow outlets 114, 116 on the left. FIG. 12B is a schematic of the system 100 showing locations of the transducer 118, reflector 120, and flow channels. FIG. 12C is a schematic illustrating one possible mode of operation of the AWD system 100 with the dash lines representing the nodal plane locations of the standing wave. FIG. 12D is a schematic of the flow profiles within the AWD system 100. FIG. 12E is a cross-section of the AWD system 100 and FIGS. 12F and 12G are cross-sections of alternate duct arrangements for the AWD system.

The AWD system 100 can be operated in horizontal and vertical orientations. Multiple inlets 110, 112 are shown on the right and multiple outlets 114, 116 on the left. The inlet 110 and the inlet 112 are coaxial rectangular ducts with an axis 107. In the orientation shown, the flow travels horizontally from right to left through a flow chamber 109, in this case a rectangular duct. In general, AWD systems include a piezoelectric material configured to be excited to generate an angled acoustic standing wave with a wavelength and an acoustic radiation force in the flow chamber oriented at an acute angle relative to the direction of mean flow through the flow chamber and the flow chamber has a minimum internal dimension that is at least 10 times (e.g., at least 50 times, at least 100 times, or at least 1000 times) the wavelength of the angled acoustic standing wave. In the AWD system 100, an angled standing wave is generated at 45° to the flow direction by a PZT-8, 1 MHz, 1 inch by 1 inch transducer and a stainless steel reflector. Optionally, some systems include multiple transducer/reflector pairs. The minimum internal dimension of the flow chamber 109 of this system is the height 108 of the flow chamber which is about 0.75 inches. In a test described in more detail below, the AWD system 100 was operated vertically with flow downwards to eliminate gravity effects on particle deflections. A mixture of polystyrene beads and water was pumped downward through the 0.2-inch middle inlet channel at a velocity of 155 cm/min. In the AWD system 100, the middle inlet channel (inlet 110) has a cross-sectional area of about 0.15 square inches. In general, AWD systems have mixture inlets with cross-sectional areas of between 0.01 and 2 square inches (e.g., 0.05, 0.1, 0.25, 0.5, 0.75, or 1 square inches).

The space between the ultrasonic transducer and the reflector has a first portion within the flow chamber and a second portion outside the flow chamber. In the acoustic chamber of the AWD system 100, thin acoustically transparent membranes 121 are used to separate the mixture flow from the prismatic void regions (i.e., the second portion outside the flow chamber) set up by the angular transducer and reflector set up. Optionally, the system can include cooling water system in fluid connection with the prismatic void regions. For example, pumps can circulate water through these regions to maintain a constant fluid temperature. In some systems, these prismatic void regions are filled with solid material having an acoustic impedance equivalent to the host fluid. This approach has been found to eliminate flow problems associated with the triangular regions while allowing the angled wave to pass with minimal reflections.

As shown in FIG. 12E, the straight, rectangular duct includes an inner duct (inlet 110) which flows a mixture of particles and a host fluid, and an outer duct (inlet 112) which flows a buffer flow. The buffer flow duct (inlet 110) completely surrounds the mixture flow duct (inlet 112). The mixture flow duct stops before the acoustic region where the acoustic standing wave passes through the system at an angle to the flow direction. The mixture flow duct (outlet 114) is then continued in the rectangular duct system after the acoustic standing wave. As a result, the angled acoustic standing wave passes through both the mixture flow stream and the buffer stream as shown in FIG. 12C. The system amounts to two inlet flows entering the acoustic standing wave and two exit flows leaving the standing wave. The inlet and exit ducts are aligned. The acoustic standing wave is at an angle to the flow direction in the duct.

The flow rates are set to generate laminar flow in the chamber and operate below a Reynolds number of 200 based on equivalent duct diameter. The low Reynolds number results in shear dominated flow, with no turbulence. The flow rate is set in three of the four streams. The two inlet flow rates are set to push the flow, and either outlet flow duct can be set to pull the flow. This push and pull operation assures the flow streams stay laminar and straight, and also provide a means to modify flow profiles for desired particle separation. The average buffer flow velocity can be set above or below the average flow velocity of the mixture flow. As the mixture flow passes through the angled, acoustic standing wave, the particles in suspension will be deflected downward along the wave front as shown. The particle deflection from the horizontal direction can vary from zero up to the wave direction. The deflection is a factor of the M factor. If the M factor is large enough to stop the flow through the waves, the particles will travel along the wave angle. The particles will be carried by the fluid velocity component parallel to the wave. The host fluid direction will be unaffected by the acoustics, and will travel horizontally to the mixture exit duct shown.

Typical velocity profiles through the acoustic section of the AWD system 100 are shown in FIG. 12D. The flow is at an extremely low Reynolds number, which provides shear flow with rapid development in a duct. The flow wants to flow in layers, or laminar flow. This is why at low Reynolds numbers, cylinders have lower drag coefficients than spheres. Three-dimensional regions in the duct shape should be avoided. The inner mixed flow duct should have a high aspect ratio (e.g., of at least 5:1, 10:1, 15:1, 20:1, 25:1, 50:1, 100:1)) such that the mixture duct provides approximately two-dimensional flow for stability. In the AWD system 100, the aspect ratio is about 7:1.

Buffer flow around the duct at the side edges as shown in FIG. 12E is anticipated to limit wall boundary flow effects. No eddies will exist due to viscous dissipation at low Reynolds number. As a result, fully developed, two dimensional laminar flow profiles will develop quickly in the ducts and will enter near the acoustic region in both the mixture duct and the buffer duct as shown. The buffer flow rate is set to allow rapid energizing of the shear layer between the streams thereby providing near constant velocity in the mixture stream flowing through the angled standing wave. The mixture flow duct is terminated well before the acoustic region to allow elimination of the shear layers between the streams as shown in FIG. 12D. In general, the distance di between the inlets and the space between the ultrasonic transducer and the reflector 120 where the angled wave is formed is between 0.025 and 2 (0.5 e.g., 0.05, 0.25, 0.5, 0.75, or 1 inches). In the AWD system 100, the distance di between the inlets and the space between the ultrasonic transducer 118 and the reflector 120 where the angled wave is formed is approximately 0.5 inches.

Figure 13:
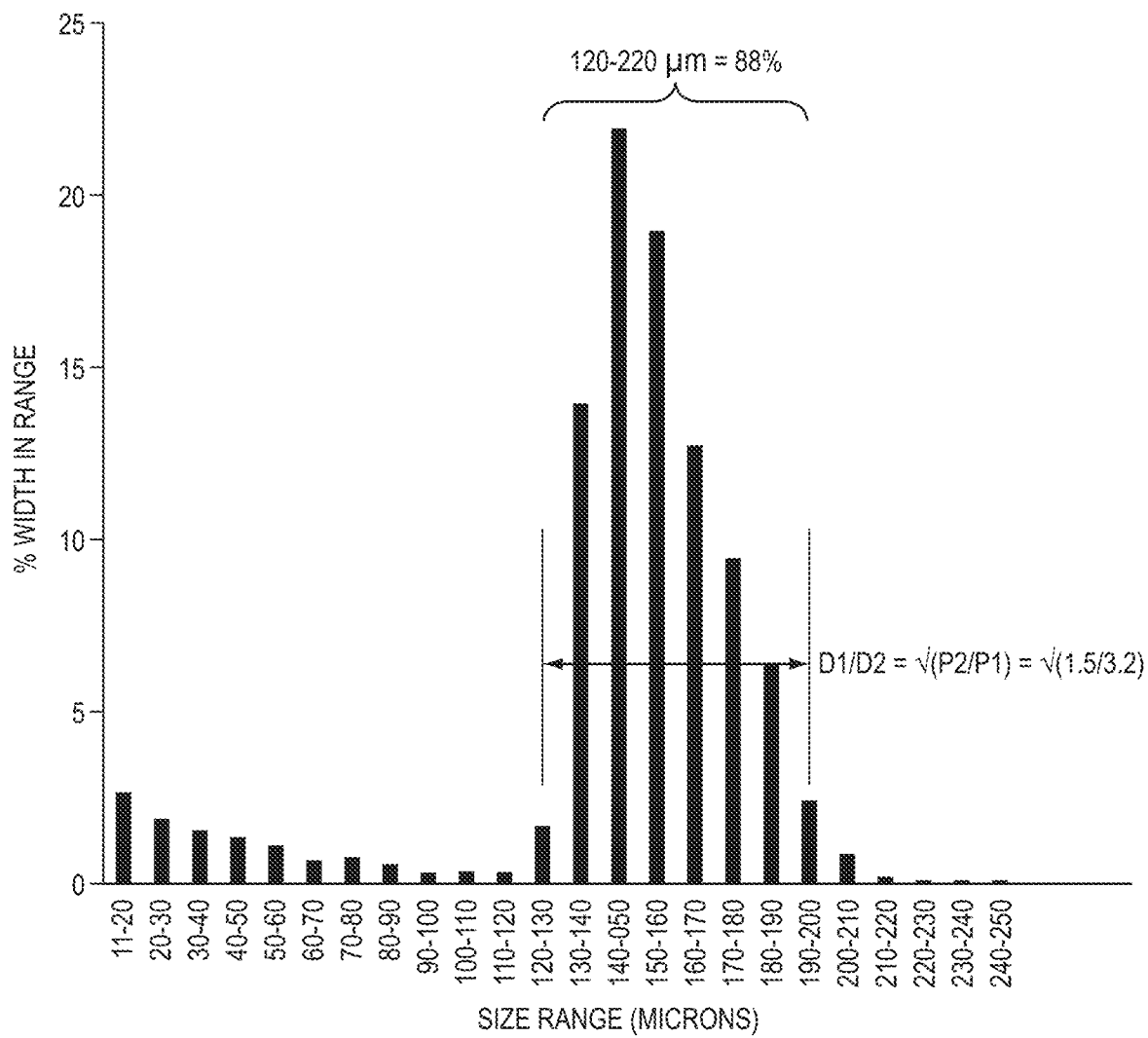
FIG. 13 is a particle size distribution of the polystyrene beads used in experiments.

FIG. 13 is a particle size distribution of polystyrene beads used to test the AWD system 100. The beads used have a mean diameter of about 150 μm and sizes as small as 20 μm and as large as 220 μm. The mixture contained two grams of beads per liter of water. This allowed for visual observation of the mixture flow. A water buffer flow was pumped around and parallel to the mixture at a velocity of 23 cm/min. Electrical power to the transducer was varied from zero to 3.2 Watt (W) and particle deflection was recorded. The wide range of particle size resulted in an even bigger variation of the M parameter. The expectation was that for certain power and fluid velocity, the larger particles will deflect at the 45° wave angle, while the smaller particles would not deflect at all, or at a small angle.

Figure 14A:
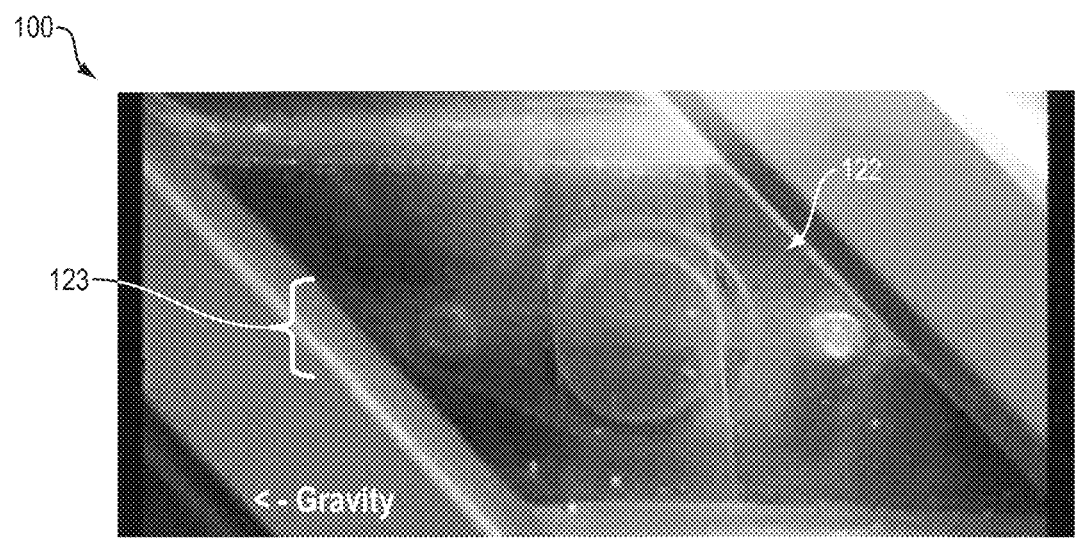
FIGS. 14A-14F are photos of polystyrene bead deflection as a function of electrical power to the 1 MHz transducer setting up an acoustic standing wave at a 45°.
Figure 14B:
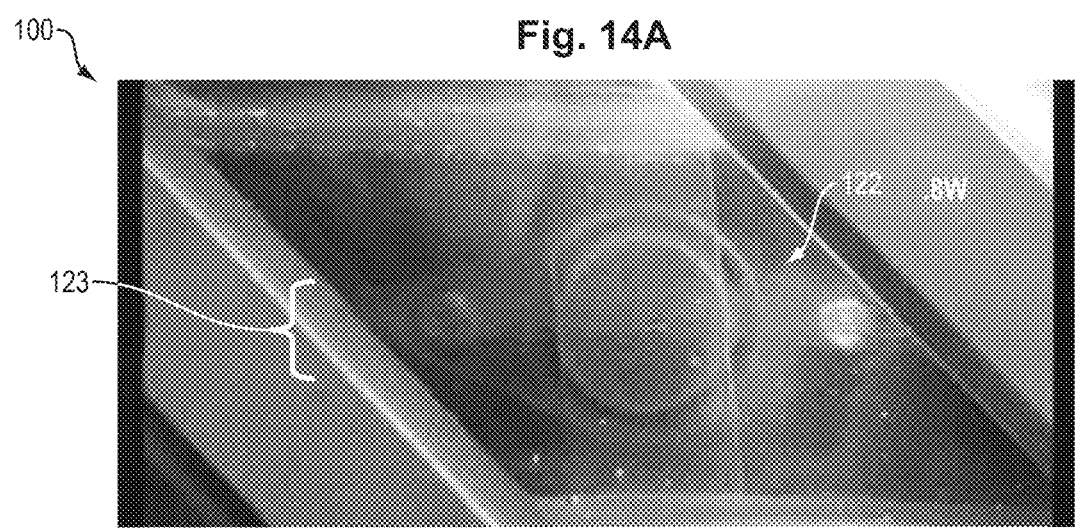

FIGS. 14A-14F are photos of polystyrene beads 122 flowing through the AWD system 100 during the test to show bead deflection as a function of electrical power to the 1 MHz transducer setting up an acoustic standing wave at a 45°. These figures show that bead deflection increased as the power (0 W in FIG. 14A, 0.8 W in FIG. 14B, 1.5 W in FIG. 14C, 1.8 W in FIG. 14D, 2.4 W in FIG. 14E, and 3.2 W in FIG. 14F) was increased. In these photos, the mixture flow is from right to left, gravity forces are right to left, and the acoustic standing wave axial direction is from upper left to lower right in the model window orientation shown. FIG. 14A shows the mixture flow with no acoustics. Without acoustic forces, the beads 122 flow horizontally with the fluid and no particle deflection is observed with the all of the beads flowing to an exit region 123.

Figure 14C:
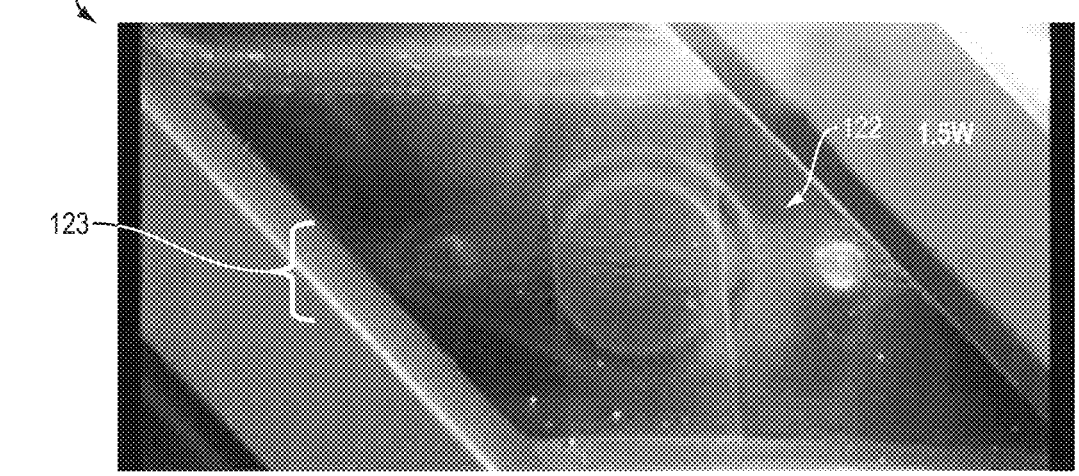
Figure 14D:
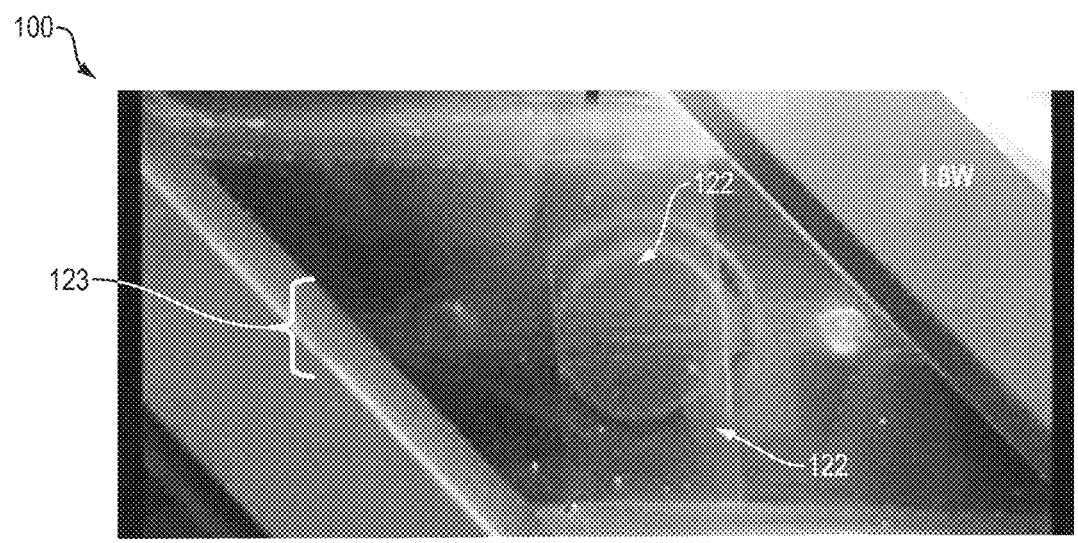
Figure 14E:
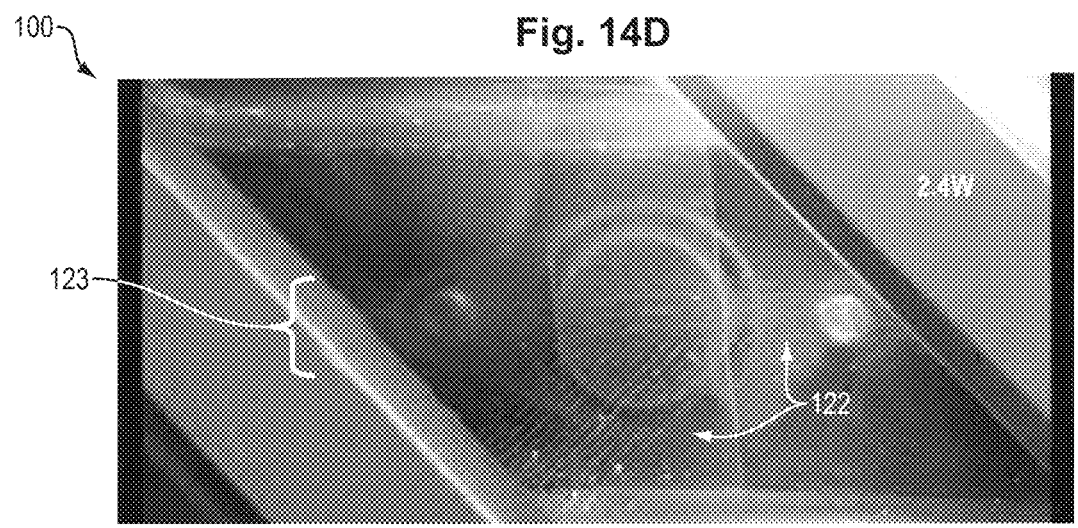
Figure 14F:

The M factor and particle deflection increases directly with electric power supplied to the transducer. The mixture stream was seen to deflect down at an angle less than the wave angle, as it moved through the angled wave from right to left for power up to 1.5 W (see FIG. 14B). At 1.5 W, larger beads started to deflect along the angled wave front while smaller particles traveled straight through the acoustic field, thereby exhibiting fractionation (FIG. 14C). As the power was increased above 1.5 W, medium-sized and smaller-sized beads deflected at the 45° wave angle (FIG. 14D and FIG. 14E), until at 3.2 W, all the visible beads were deflected along the standing wave (FIG. 14F). In addition, the exit region 123 of the smaller beads that were not deflected along the standing wave began to exhibit a gradually increasing deflection as the power increased.

The bead diameter variation was calculated using the M factor based on power variation measured from first noticeable bead deflection to all bead deflection along the wave front. At a power of 1.5 W, the analytical calculations indicated that large particles of 200 μm were deflected along the wave front and a majority of all particles larger than 130 μm were deflected along the wave front at a power of 3.2 W. The analytical prediction is that identical values of the product of the square of particle diameter and acoustic energy, which is proportional to power, yield identical particle deflections. The results agree well with the documented size distribution for the beads and the observed bead behaviour. These test results verify the analytical model, and demonstrate the ability to select and differentiate by size or material property using angled wave technology.

Some AWD systems have a third outlet configured to concentrate material being deflected. For example, these systems can have the second outlet disposed between the first outlet and the third outlet where a cross-sectional area of the third outlet is smaller than a cross-sectional area of the second outlet.

Figure 15A:
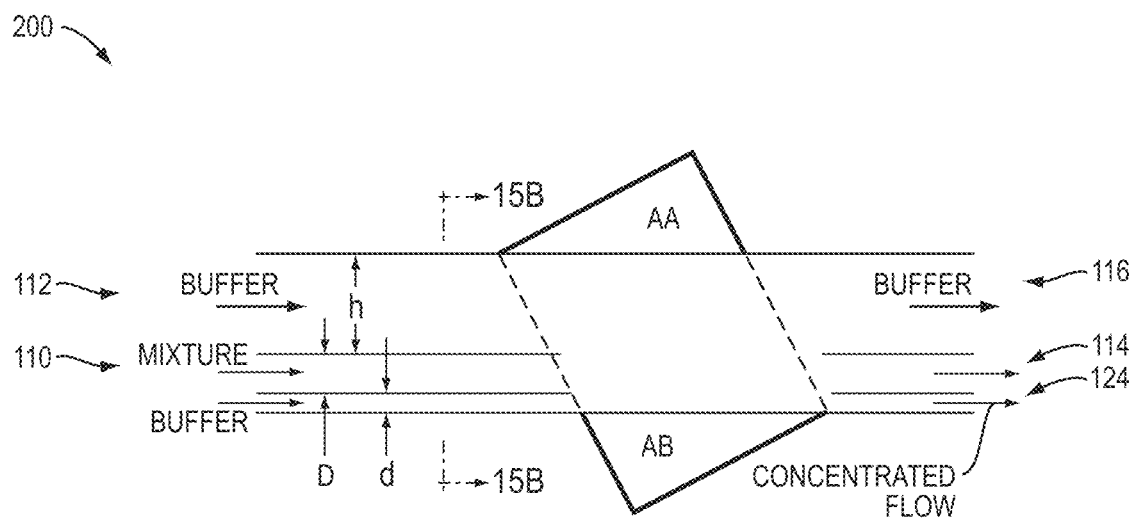
FIGS. 15A and 15B illustrate an AWD system configured for concentrating particles or cells by lowering the mixture duct and constricting the lower buffer stream.
Figure 15B:
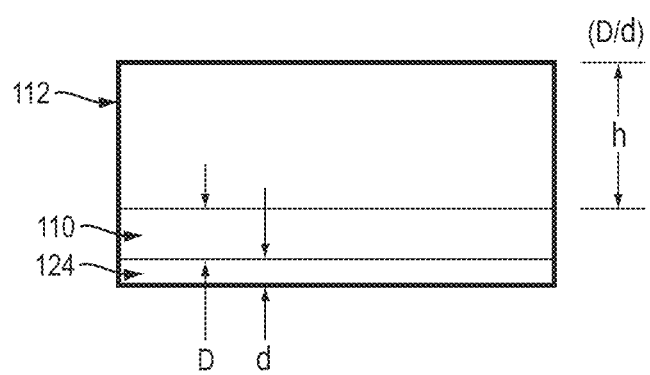

FIGS. 15A and 15B illustrate an AWD system 200 with such duct configuration. The AWD system 200 is configured for concentrating particles or cells by lowering the mixture duct 110 and constricting the lower buffer stream. The outlet mixture duct 114 is attached at the side walls after the flow passes through the acoustic wave to provide particle collection with higher concentrations. This mixture duct attachment is made after the flow passes the acoustic field, allowing buffer flow around the inlet mixture duct 110 before the acoustic wave and thus providing good flow profiles and particle concentration. The duct flow rates can be varied with push/pull mechanisms as described above to help obtain the desired separation and concentration. The mixture duct wall attachment isolates an exit duct 124 from the buffer flow duct (outlet 116). D is the height of the outlet mixture duct 124. h is the height of the buffer flow duct 116 above the mixer duct 114. d is much smaller and is the height of the third outlet duct 124. In the AWD system 200, the width of the ducts is the same. The concentration rate should ideally be D/d if the velocities in both ducts were the same. D/d could be varied accordingly. In AWD systems with this configuration, height D of the outlet mixture duct 114 is generally have between 2 and 100 times the height d of the third outlet wall buffer duct 124 (e.g., 3, 5, 10, 25, 50, 75 times the height d of the third outlet wall buffer duct 124). The mixture to lower buffer flow rate ratio should ideally be D/d if the velocities in both ducts were the same. In the AWD system 200, the height D of the mixture duct 114 is about 3 times the height d of the third outlet 124. The height h of the buffer inlet 112 and buffer outlet 116 can be much smaller than shown in the figure and will be chosen with CFD for specific applications.

Some AWD systems have a plurality of third outlets, each of the plurality of third outlets offset from an axis of the second outlet in a direction of deflection of the angled acoustic wave.

Figure 16:
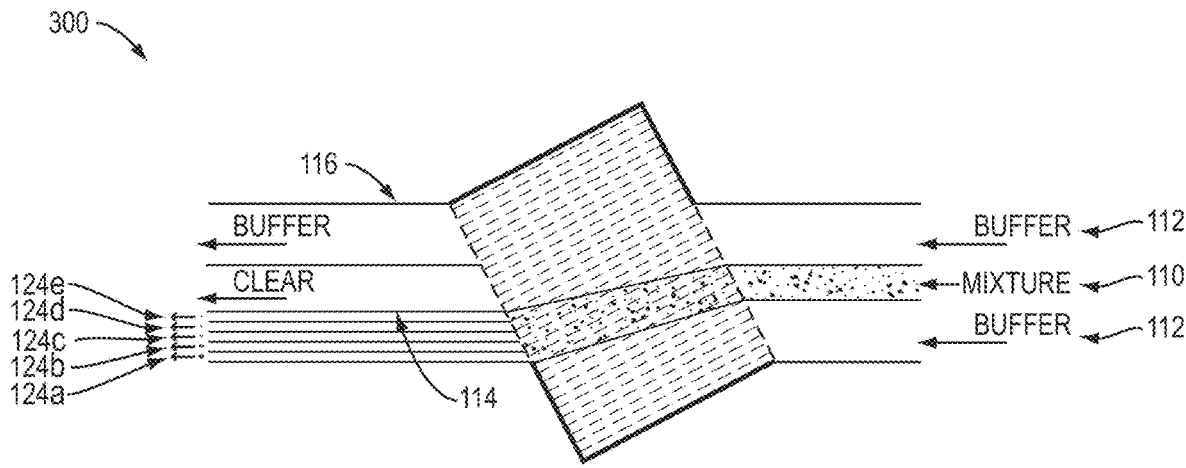
FIG. 16 is a schematic of an AWD system configured for particle fractionation.

FIG. 16 is a schematic of an AWD system 300 configured for particle fractionation. In the orientation of FIG. 16, the direction of deflection of the angled acoustic wave is downward and the multiple collection ducts 124a-124e are provided below the mixing duct (outlet 114) to collect different size particles. The AWD system 300 has five collection ducts 124a-124e but some AWD systems configured for fractionation have more collection ducts (e.g., 10 collection ducts 15, collection ducts, or 20 collection ducts) or fewer collection ducts (e.g., 4 collection ducts 3, collection ducts, or 2 collection ducts). The M factor is set in Region 1 along with push/pull flow rate settings to provide operation where different deflections occur with different particle sizes. One example configuration has a total system height of one inch with the five collection channels spanning a typical distance of 0.4 inches in total. The system is scalable up or down as needed to accommodate smaller or larger flow rates. Fractionation systems can be used, for example, for cell enrichment from a leukopack (e.g., to fractionate the different cells such as red blood cells, monocytes, granulocytes, and lymphocytes); to fractionate a starting population of T cells according to size; to fractionate an affinity bead/cell complex from unbound free cells; or to fractionate a population of free cells, affinity bead/cell complex A, and affinity bead/cell complex B. Use of the M-factor can aid in design and operation of acoustic separation systems In one example, a mixed population of two particles of the same material, one of size 5 micron and one of size 10 micron need to be separated in a 45° angled wave device. Operating parameters such as flowrate, power, and frequency are selected such that the M-factor for the bigger particle is $M_{10}=0.8$. For a 45° angled wave device, this M-factor that results in a particle deflection of 45 degree for the ten-micron particle. Since M scales with the square of the particle radius, the M-factor for the smaller particle is $M_5=0.8/4=0.2$. The deflection angle for this particle is about two degrees. Therefore, a proper angled wave setup with a wave angle of 45° is able to fractionate these two populations.

In a second example, the goal is to fractionate three different cells, lymphocytes, monocytes, and neutrophils, cells found within the white blood cell population. Lymphocytes have a typical size of 6 micron. Monocytes and neutrophils are about ten microns. In addition, the acoustic contrast factor of the lymphocytes is smaller than that of the monocytes. A 45° degree angled wave device can be tuned such that the monocytes have an M-factor of 0.75. The neutrophils being of the same size and slightly smaller acoustic contrast factor have a slightly smaller M-factor of about 0.725. The smaller lymphocytes M-factor scales as $(6/10)^2=0.36$, or 36% that of the monocytes, resulting in an M-factor of 0.27. The deflection curve for a 45° wave angle indicates that the monocytes and neutrophils deflect at 45°, whereas the lymphocytes deflect at about 5°. A system with properly designed outlets will be able to harvest separately the monocytes and neutrophils in one channel, and the lymphocytes in a separate outlet, thereby separating and enriching the lymphocytes.

In a third example, the goal is to fractionate the output of an affinity cell selection process. An 25 micron affinity bead is used for a TCR+ T-cell negative cell selection process. The TCR+ T-cells are bound to the affinity bead and form a complex of affinity bead with multiple TCR+ cells attached to the bead. The TCR− T-cells are not bound, remaining in solution as free unbound cells. An angled wave system is then used to fractionate these two populations, free unbound TCR− cells from the affinity bead/TCR+ cell complexes. The radius of the T-cell is about 6 micron. Therefore, the ratio of the M-factor is $(25/6)^2=17$. Choosing system parameters such that the affinity/cell complex has an M-factor of 1 results in the deflection of the complex at the wave angle. The unbound free cell then has an M-factor of $1/17=0.06$ which means the free cells deflect at an angle of less than 1°, thereby effectuating a fractionation process of the affinity bead/cell complex from the free cells.

In a fourth example, the goal is to fractionate a mixed cell populations consisting of similar sized cells but with a difference in acoustic contrast factor, with cell A having a contrast factor of 0.03 and cell B having a contrast factor of 0.06. An 45° angled wave system is used to separate cells A from cells B. The system is tuned such that the M-factor of cell B is 0.75, resulting in a deflection of cells B at an angle of 45°. Since the M-factor scales with the contrast factor, the M-factor for cell A is 0.75/2=0.375, resulting in a deflection of about 5 degrees for cell A. A properly designed system should allow for the separation of cells A at 5 degrees from cells B at 45 degrees.

Figure 17A:
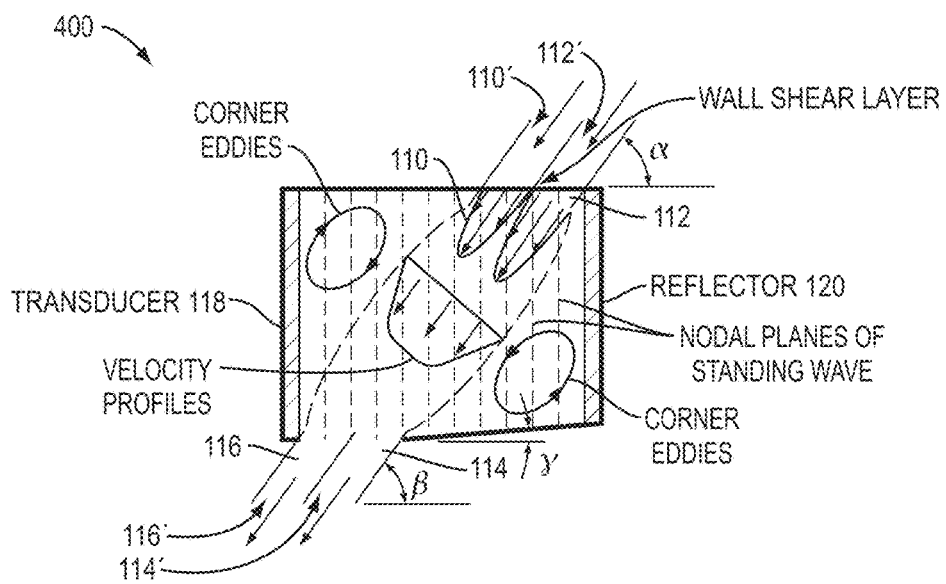
FIGS. 17A, 17B, and 17C are schematics illustrating aspects of an angled fluid device (AFD) system.
Figure 17B:
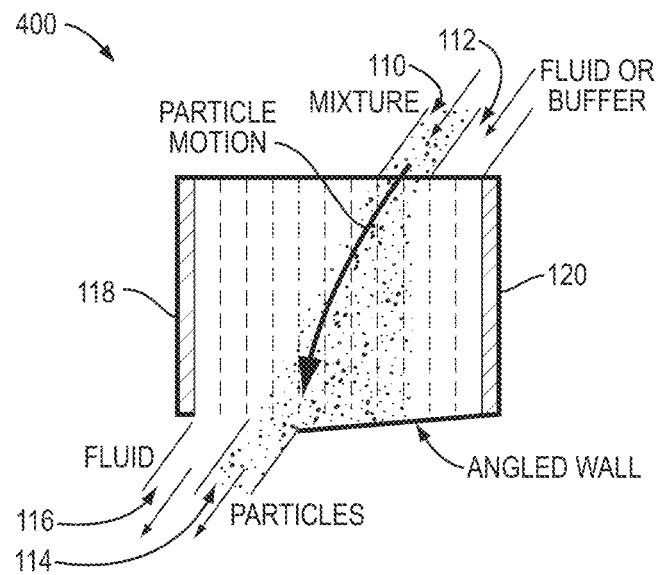
Figure 17C:
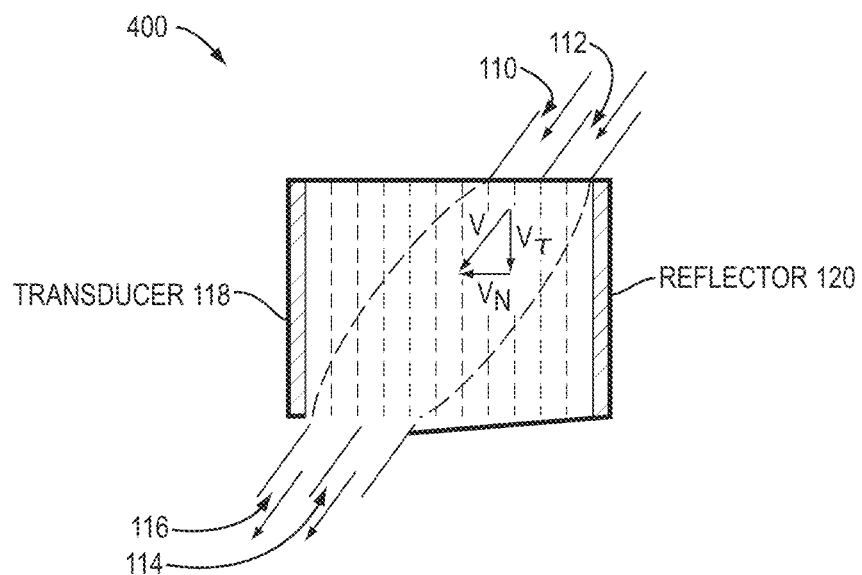

FIGS. 17A, 17B, and 17C are schematics illustrating aspects of an AFD system 400. FIG. 17A shows system geometry and flow characteristics. FIG. 17B shows particle transfer between fluids.

FIG. 17A shows the AFD system 400 with an acoustic chamber which has an ultrasonic transducer 118 on one side, a reflector 120 on the opposite side of the chamber, and multiple flow inlets 110, 112 and outlets 114, 116. The transducer 118 and chamber are designed to generate a bulk, ultrasonic acoustic standing wave traveling horizontally in the chamber as shown n FIG. 17A. The vertical dash lines shown in the figure represent the nodal plane locations of the standing wave. Two inlets 110, 112 are shown in the right top of the chamber, and two outlets 114, 116 are shown at the left bottom of the chamber. A first channel 110' ends at the first inlet 110 and a second channel 112' ends at the first inlet 112. The channels 110', 112' are at an angle alpha (α) with a plane perpendicular to the angled acoustic standing wave (in the case the horizontal direction) of 60°. In AFD system 400, the first channel 110' and the second channel 112' both have a substantially straight section extending at least 0.5 inches from their respective inlet 110, 112.

The two lower exit ducts are at an angle beta (β) with the horizontal of 70°. In some systems, the angles alpha and beta are the same. In some systems, the four ducts all enter the acoustic chamber at different angles. These angles though, will vary between zero and ninety degrees. In some systems, the angle alpha is between 30° and 88° (e.g., more than 35°, more than 40°, more than 45°, more than 50°, more than 55°, more than 60°, less than 80°, less than 75°, less than 70°, less than 65°, less than 60°, less than 55°, less than 50°). In some systems, the angle beta is between 30° and 88° (e.g., more than 35°, more than 40°, more than 45°, more than 50°, more than 55°, more than 60°, less than 80°, less than 75°, less than 70°, less than 65°, less than 60°, less than 55°, less than 50°).

Fluid enters the acoustic chamber through the inlet ducts, and exits the chamber through the exit ducts. Typical duct dimensions are channels depths of 0.5 to 1 inch and channel widths of 0.1 to 0.4 inches. The flow rates are set to generate laminar flow in the chamber and operate below a Reynolds number of 200 based on duct diameter. The low Reynolds number results in shear dominated flow, with no turbulence. The flow rate is set in three of the four ducts attached to the acoustic chamber in FIG. 17A. The flow is both pushed and pulled. The two inlet flow rates are set to push the flow, and the outlet flow carrying the particles is set to pull the flow. This push and pull operation assures the flow streams go where desired. The outlet mixture flow can be set above or below the flowrate entering one of the inlet ducts. Typical flow profiles are shown in the chamber in FIG. 17A. Fully developed laminar flow profiles enter the acoustic chamber as shown. The wall shear layer between at the chamber inlet quickly mix out. A fairly uniform flow develops for a while near the interface of the two injected streams as shown in FIG. 17A. The flow shear forces on the fluid in the corners causes flow rotation, and will generate large scale eddies as shown. This flow rotation will be slow and solid body like rotation because of the low Reynolds number. The flow rates are controlled at both the inlets and the exits. In most of the operations, both inlet duct flow rates will be specified and one of the exit flow ducts will be specified. This type of operation is called push/pull. The acoustic standing wave can be planar, or three dimensional. Planar standing waves are preferred. The wall of the flow chamber adjacent to the first outlet in a direction of deflection of the angled acoustic wave can extend at an acute angle relative to a plane perpendicular to the angled acoustic standing wave. In the AFD system 400, the lower wall of the chamber is tilted down an angle gamma (γ) as shown. This wall slope is designed to help collect particles deflected by acoustic radiation forces. Some AFD systems have wall slopes between 1 and 20 degrees (e.g., more than 2 degrees, more than 3 degrees, more than 5 degrees, more than 10 degrees, less than 15 degrees, less than 10 degrees, less than 7.5 degrees, less than 5 degrees).

FIG. 17B presents the AFD system 400 operating with a fluid mixture with particles in suspension entering through the inlet 110 and clear fluid entering the chamber in the inlet 112. The particles are assumed to have a positive acoustic contrast factor, which means they will deflect towards the nodal plane surfaces as shown. In this manner, all the particles get deflected in the down direction. The angled wall at the bottom of the chamber allows particles to drop out of the acoustic field without getting trapped in the wall shear layer, or held by the acoustic edge effect.

FIG. 17C schematically depicts the fluid flow direction of the AWD system 400. The fluid velocity is decomposed into components normal and tangent to the acoustic standing wave nodal planes. The normal direction represents the axial direction of the standing wave. For a planar wave, this is the direction of the radiation forces on the particles in the mixture. As a result, the radiation forces slow and speed up the normal velocity component of the particles with respect to the fluid normal velocity. The tangential velocity component of the particles remains the same as the fluid. As a result of this effect, the particles are deflected at an angle to the fluid towards the downward direction. If the radiation forces are large enough, the normal velocity of the particle will approach zero, and the particles will move vertically downward while the fluid continues to flow across the chamber towards the exit duct. It is important to realize that these particle deflections use fluid velocity, and more specifically the component of fluid velocity in the downward direction. The fluid carries the particles down. This effect is completely separate from gravity. The process is gravity independent.

Figure 18A:
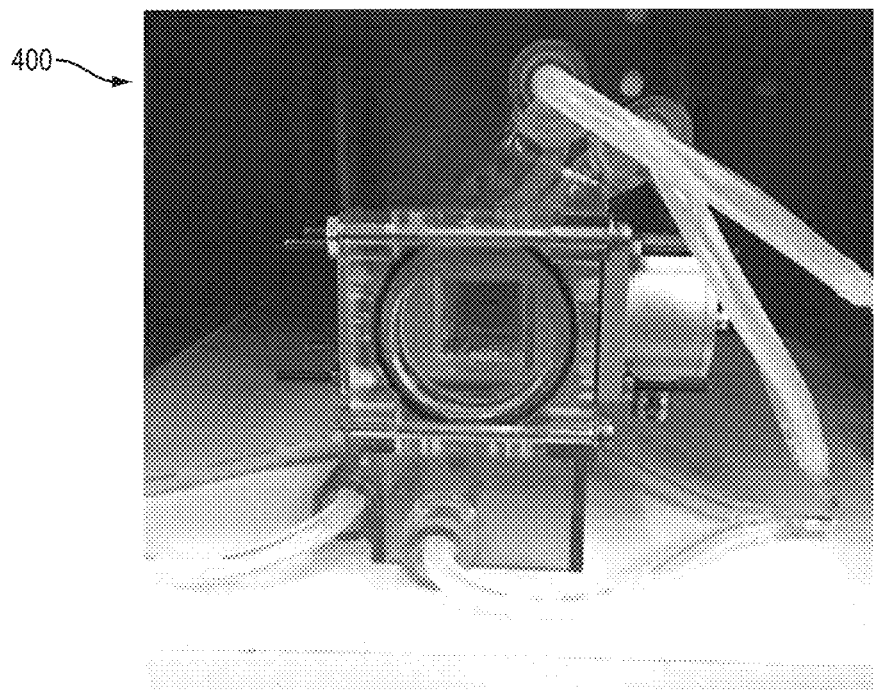
FIG. 18A is a photograph of the AFD and FIG. 18B is a schematic of the setup showing fluid streamlines from a CFD prediction.
Figure 18B:
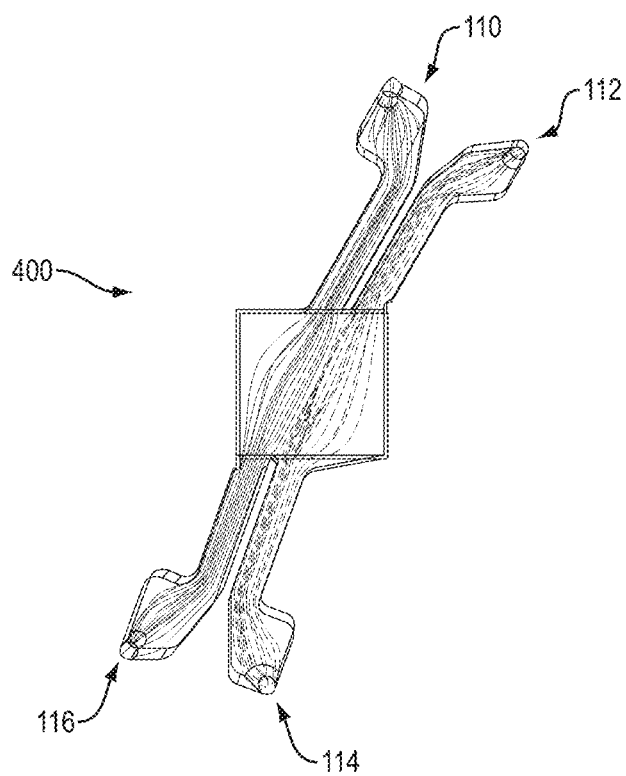

FIG. 18A is a photograph of a prototype of the AFD system 400 tested and FIG. 18B is a schematic of the setup showing fluid streamlines from a CFD prediction. In FIG. 18B, the red represents a mixture stream and blue represent a buffer stream. The CFD results show that the flow is regular and uniform without any mixing between the streams. There are two flow inlets 110, 112 and two flow outlets 114, 116 in the AFD system 400. The top inlets are at an angle of 60° with respect to the horizontal direction. The outlets are at 70°. Pumps are used to control both the amount of flow entering the acoustic chamber through the inlets and the flow exiting the outlets (push-pull control). The AFD device was tested with a 1 MHz acoustic standing wave operating at 1 W. The two flow streams make about a 30° angle with the standing wave in the acoustic chamber.

Figure 19A:
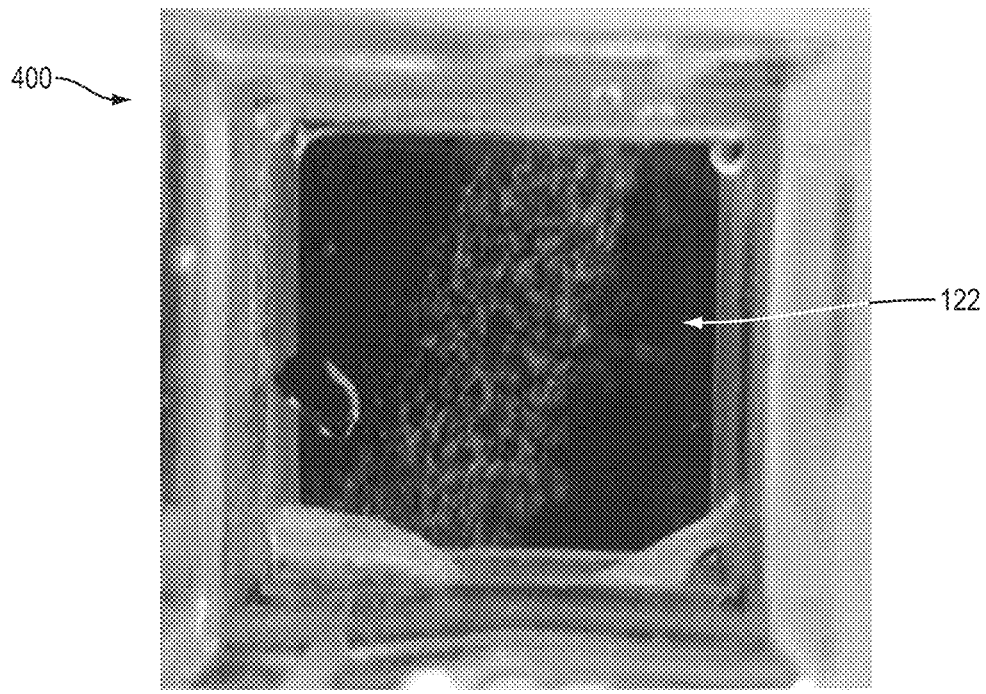
FIGS. 19A and 19B are photographs of the acoustic chamber window of the AFD system showing particle movement through the AFD system without acoustics (FIG. 19A) and with acoustics (FIG. 19B).
Figure 19B:
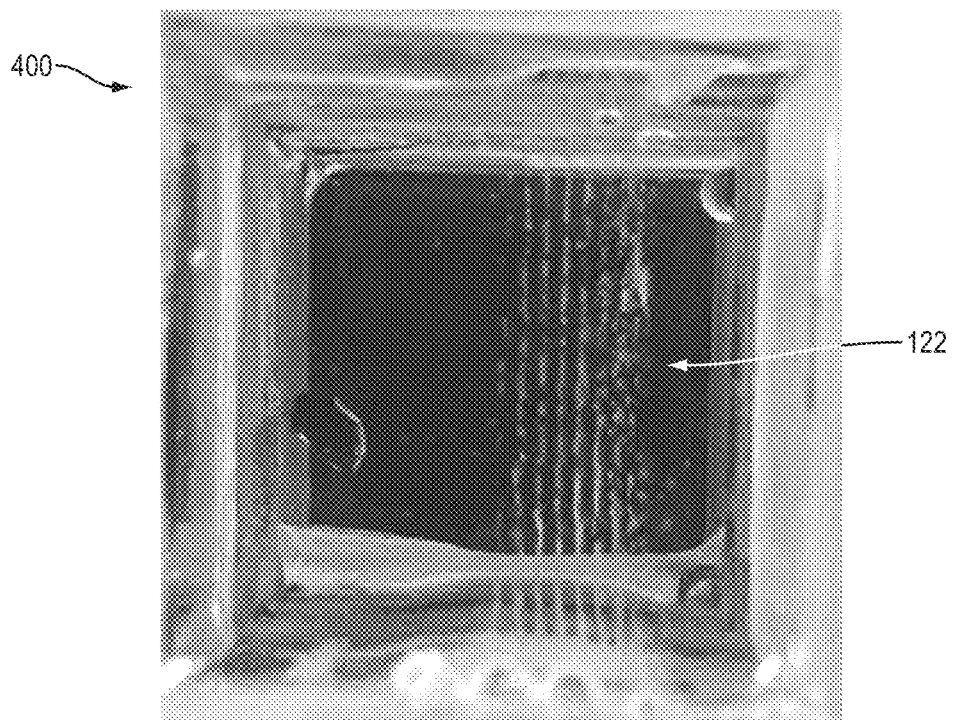

FIGS. 19A and 19B are photographs of the acoustic chamber window of the AFD system showing particle movement through the AFD system without acoustics (FIG. 19A) and with acoustics (FIG. 19B). The test was conducted with 200 ml/min flowing through all inlets and outlets. This results in mixture flow velocities of about 160 cm/min. The mixture stream of polystyrene beads 122 and water is readily visible. The mixture was 2 grams of beads 122 per liter of water. The beads 122 are those described with reference to FIG. 13.

In FIG. 19A (acoustics off), the mixture stream is seen to flow directly from the upper left inlet 110 to the lower left outlet 116 as predicted with CFD. The second stream is water, and it is not visible in the photograph. FIG. 19B (acoustics on) shows the effect of the angled standing waves on the motion of the beads 122. The M/sin(γ) parameter for the test was greater than 1.0. The beads 122 were deflected along the angled wave front almost immediately as they enter the acoustic chamber. This resulted in the vertical motion of all the visible beads 122 from the mixture stream to the buffer stream and down to the bottom of the chamber and into the lower right outlet 114. This result occurs at all buffer flow rates and shows the ability of this system to be used for particle washing, or for particle separation and/or collection at high flow rates when compared to conventional ultrasonic separator systems. The AFD system 400 is not limited to two streams and can be modified to include many different angle variations. The AFD system 400 has the potential to work with a variety of fluid/particle mixtures where the substance in suspension could be beads, cells, exosomes, viruses, oil droplets, or any material that has a different density, compressibility, or contrast factor than the host fluid. The system can work with nanoparticles since the acoustic radiation force effect is amplified by the angle that the flow makes with the acoustic wave.

Some systems are configured to provide fractionation by providing a constriction in the outlet channel positioned to receive deflected material. For example, the fourth channel ending at the second outlet can have a first cross-sectional area. The third channel ending at the first outlet can have a first section with the first cross-sectional area and a second section with a second cross-sectional area that is smaller than the first cross-sectional area with the second section of the third channel located between the first outlet and the first section of the third channel.

FIGS. 20A and 20B illustrates this approach to increasing the concentration of the particle mixture drawn off with AFD systems. In AFD system 500, the lower outlet duct 114 is constricted near the acoustic chamber. This constriction is shown in the particle outlet that is pulled, for example, by a pump to a desired flowrate. Since the flowrate is set by the pull rate, any area constriction results in a velocity increase. The outlet duct constriction d/D increases the flow velocity by D/d for the two dimensional duct shown in FIGS. 20A and 20B. FIG. 20B presents approximate flow profiles for a moderate constriction with a pull flow rate such that the peak velocity in the acoustic chamber occurs in the area near the exit duct constriction region. The higher velocities occurring near the entrance of the exit ducts 114, 116, and near the separation streamline dividing the two flows will provide better separation with fewer particles moving back to the mixture stream. The higher velocities mean higher tangential velocity components to carry the particles (e.g., beads 122) down. As an example, if the flowrates in all four ducts are set the same by the push-pull mode and the constriction is 90% of the duct area, then the velocity near Q4 exit duct entrance will increase ten fold when compared to the second outlet duct flow, Q3, or with respect to the inlet flow of both ducts (Q1 and Q2). This effect is reflected flow profile shown in FIG. 20B. The length of the constriction region shown in the schematic of the velocity profiles provides velocity directions toward the constriction channel. This means less chance of particles re-entering the original mixture stream, and better separation efficiency. In the same configuration, and still assuming a 90% constriction, if the flowrate is set so the Q4 exit duct has one tenth the flow rate of the incoming inlet ducts, the throttled velocity is nearly or exactly the same as the un-throttled exit duct velocity in Q3 and therefore still provides the downward velocity component desired for separating the particles, while flowing much less fluid in exit duct flowrate Q4. This arrangement results in a possible ten times concentration of the mixture with each pass through the AFD separator.

FIG. 21 presents an AFD system 600 designed for particle fractionation. Four inlet ducts 110, 111, 112, 113 and four outlet ducts 114, 115, 116, 118 117 are shown. The different shadings represent CFD predictions showing the ability to maintain the four angled streams through the acoustic chamber. Again, push/pull operation allows such unique definition in the acoustic chamber. Some AWD systems include many more streams. All four flows pass though the chamber at an angle to the acoustic standing wave. If the top, or blue stream was a mixture of fluid mixture with multiple particle sizes in suspension, the particles could be fractionated into the lower three collection ducts shown in FIG. 21 using the angled wave deflection process. The system may be operated at an M factor which allows different particles to be deflected for the collection configuration shown. The same AFD system shown in FIG. 21 could be expanded to have five or more inlet ducts and five or more outlet ducts. The incoming mixture and buffer streams could then pass through many different adjacent duct pairs. Operated with push/pull technology, this would allow particle separation with many different wave angles. In the same manner, the different duct streams could be used to set different velocity profiles for different particle separation requirements.

Figure 22A:
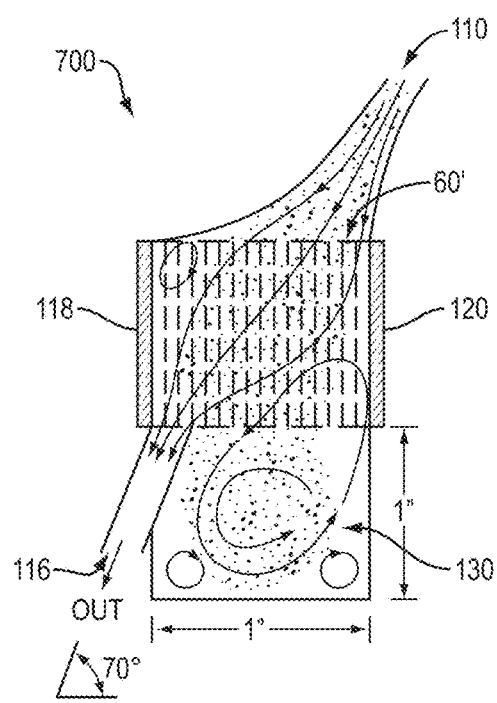
FIGS. 22A, 22B, and 22C are, respectively, a schematic, a plot of modeled flow velocities, and a cross-section of an AFD system designed for particle collection.
Figure 22B:
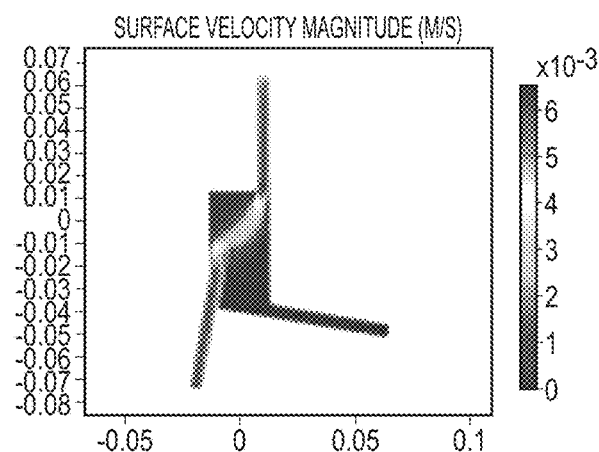
Figure 22C:
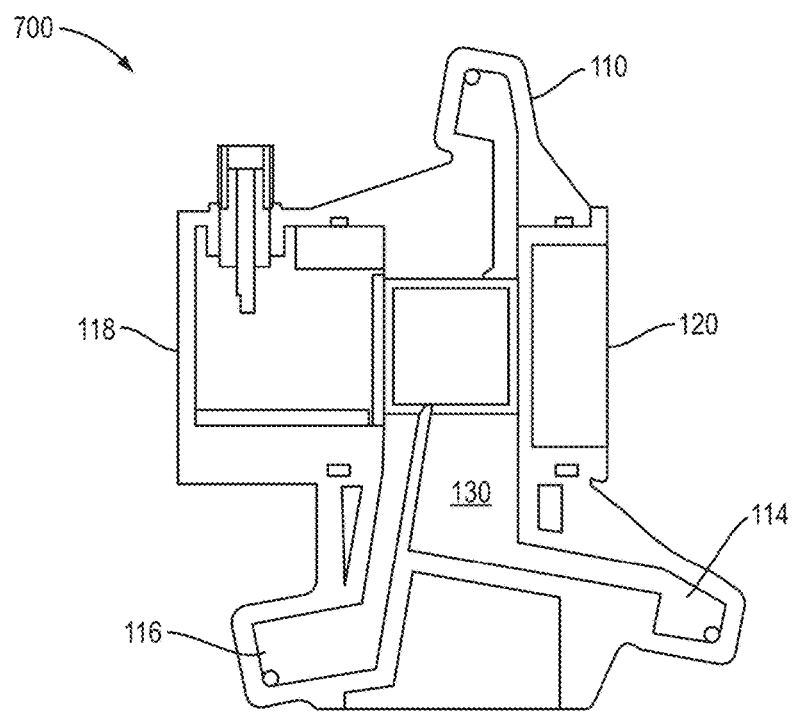

FIGS. 22A, 22B, and 22C are, respectively, a schematic, a plot of modeled flow velocities, and a cross-section of an AFD system 700 designed for particle collection. FIG. 22A shows the flow through the system. The system contains one inlet duct 110 and one outlet duct 116 attached to the acoustic chamber. A collection region 130 is shown below the flow stream passing through the acoustic chamber at an angle to the standing wave as shown. This collection is enhanced by a large scale collection vortex shown in FIG. 22A. This collection vortex is driven by the flow stream passing through the chamber and provides tangential velocity components parallel to the nodal planes which can carry the particles downward out of the mixture stream into the collection regions. The collection vortex can be furthered enhanced by drawing off fluid through the collector outlet 114 at the bottom of system. Turning the acoustics off and on in an appropriate manner to allow particles to fall down to the collection bottom could also enhance performance.

Figure 23A:
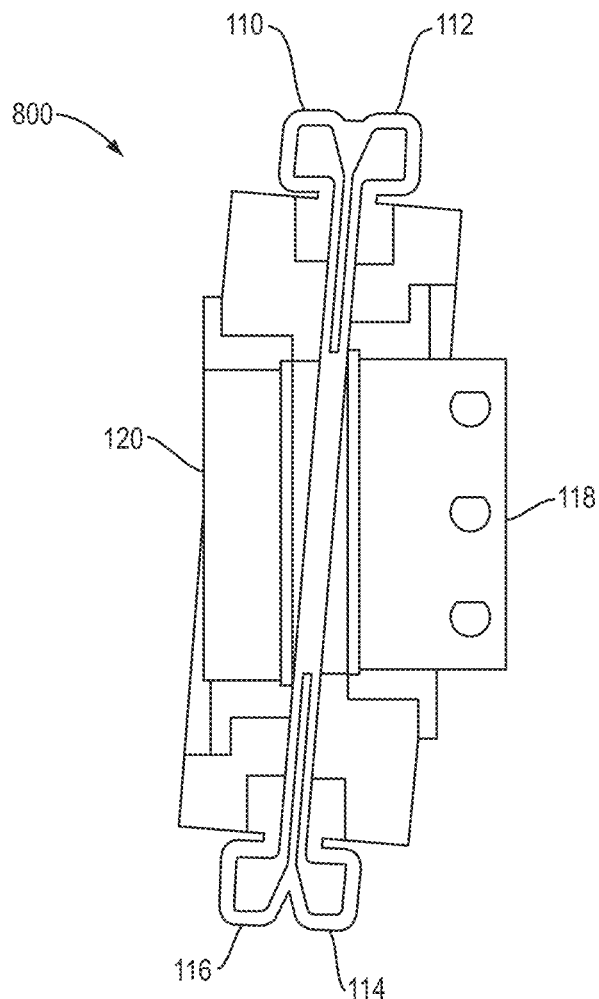
FIGS. 23A and 23B are, respectively, a cross-section and a schematic of a low angle AFD system.
Figure 23B:
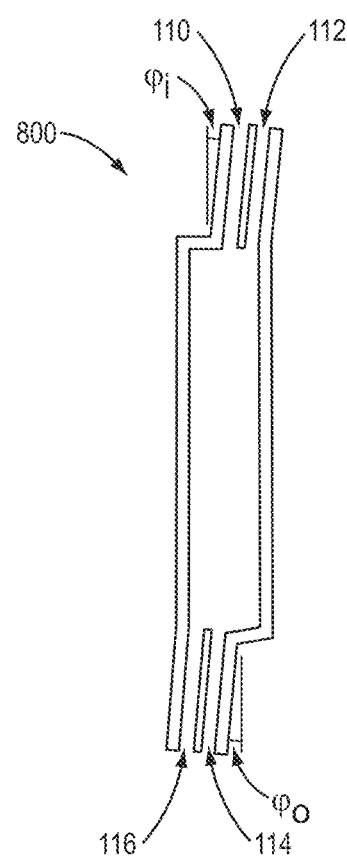

FIGS. 23A and 23B are, respectively, a cross-section and a schematic of a low angle AFD system 700. The M parameter can be used to determine the desired operation characteristics for deflecting extremely small particles (e.g., nanoparticles of the range of 100 nm to 1000 nm or 10 nm to 100 nm, or 1 to 10 nm, bacteria, viruses such as *lenti* or retro viruses, adeno associated viruses, exosomes, microvesicles, and other nano-sized particles) in suspension. The smaller the particle size, the lower the M factor. In a system with flow velocity reduced as low as possible for system feasibility, and power is increased as large as possible, then the M operating curves specify that the system should be operated at as low a wave angle as possible. Typical operating parameters for these systems are angles between nearly-zero and 15 degrees, frequencies between 2 and 50 MHz, acoustic pressure amplitude between 1 and 20 MPa), and linear velocities are on the order of 10 mm/s, 1 mm/s or 0.1 mm/s. For low M values, deflection peaks at lower wave angles. The AFD system 700 is configured for use with nanoparticles. Two inlet flow ducts 110, 112 feed the acoustic chamber and two exit flow ducts 114, 116 are used to exit the flow streams. Both the inlet angle $\varphi_i$ and outlet angle $\varphi_o$ are approximately 5°. In other ASWD system, the inlet angle $\varphi_i$ and outlet angle $\varphi_o$ are different angles (e.g., between 2° and 10°, more than 3°, more than 4°, less than 9°, less than 8°, less than 7°, less than 6°). Again, push/pull techniques can be used to control the flow streams to generate the particle fractionation desired.

The systems and methods described in this disclosure can provide macro-scale, ultrasonic separators that use bulk, acoustic standing waves angled to the direction of a fluid mixture flow field to generate particle deflection that can be used to collect, differentiate, separate, purify, or fractionate one population of particles or cells from a mixture that may contain multiple different types of particles. Particle trajectory equations provide the key physics. The universal prediction curves developed for particle deflection at all wave angles as a function of the non-dimensional parameter M defined by the ratio of acoustic radiation force to viscous drag force on the particle can be used in system design and operation. Particle deflection, measured from the fluid flow direction, varies continuously from zero to a maximum value equal to the wave angle γ, which is the angle that the standing wave makes with the flow direction. The analytical results agreed well with both numerical trajectory computations and model test results. The acoustic pressure amplitude, particle diameter and wave angle were shown to have the largest effect on particle deflection.

Results also showed that for any acoustic pressure amplitude of a standing wave, there is a wave angle of the standing wave where the radiation force stops the particle velocity normal to the wave, and as a result, the particles start to move along the wave front. This point is defined by the non-dimensional parameter M, and angle of the wave γ and operating near this point generates large particle deflection with small changes in controllable parameters such as acoustic power or flow velocity. This operating point is quite useful, since it could allow the separation of particles with minute size, stiffness or density differences.

Some of these systems and methods use standing waves angled to a flow channel or narrow flow streams injected at an angle through a fixed acoustic chamber. Both systems were shown to effectively separate polystyrene beads from a flowing mixture at high speeds when compared to conventional ultrasonic separators. Such macro scale, ultrasonic separators were also shown to effectively operate at much higher flow rates, or at much lower particle concentrations, than conventional acoustic separators. Model test results agreed very well with theory, and verified the prediction system developed. The angled wave system could work with a fluid/substance mixture where the substance in suspension could be micro carrier beads, cells, exosomes, virus, oil, or any material that has a different density, compressibility, or contrast factor than the host fluid. The analytical model predicts that the system can theoretically work even with nanoparticles since the acoustic radiation force effect is amplified by the angle the flow makes with the acoustic wave.

Figure 24A:
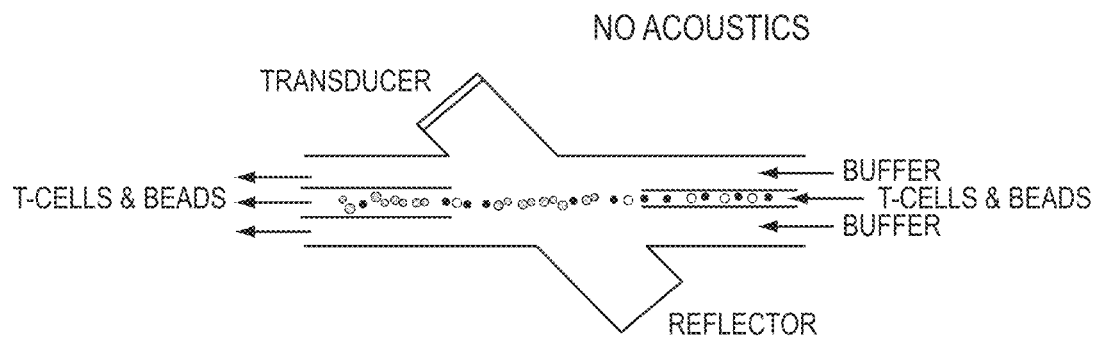
FIGS. 24A-24 C present the results of using an AWD system to fractionate T-cells from 35 um beads.
Figure 24B:
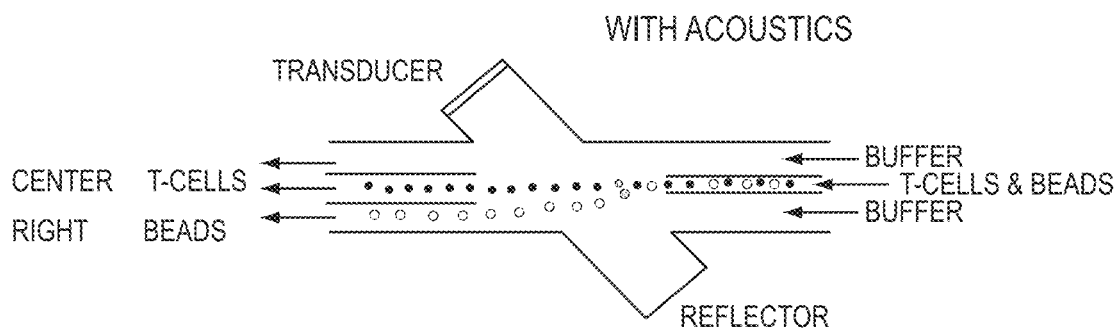
FIG. 24C is a chart of the results.
Figure 24C:
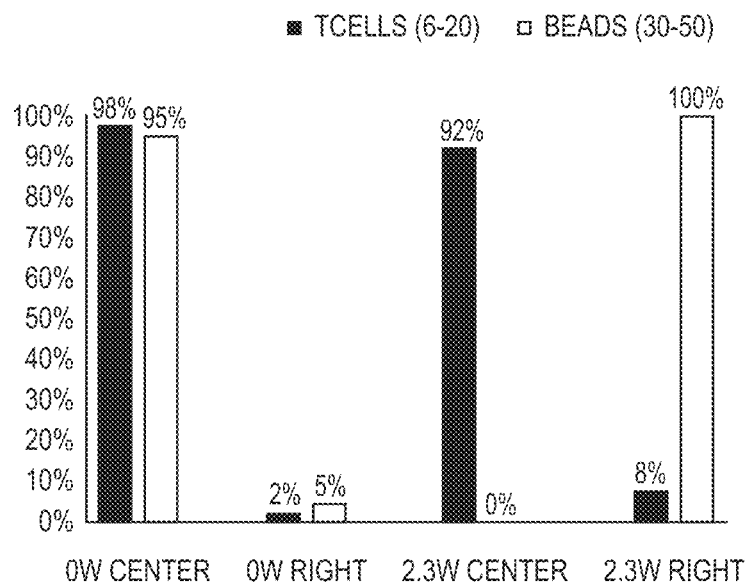

FIGS. 24A-24 C present the results of using an AWD system similar to that shown in FIGS. 12A-12E to fractionate T-cells from 35 um beads. The system had a 30° wave angle and was operated with a frequency of 2.1 MHz and flow rates of 5 ml/min of a T-cell/bead mixture through the center inlet and of 30 ml/min of a buffer through the buffer inlet. FIGS. 24A and 24 B are schematics illustrating the anticipated separation of T-cells from beads. FIG. 24C presents the results. When the system was operated without acoustics, 98% of the T-cells and 95% of the beads flowed through the center outlet. When 2.3 W of power were applied, 92% of the T-cells flowed through the center outlet and 100% of the beads were deflected into the buffer outlet.

Figure 25A:
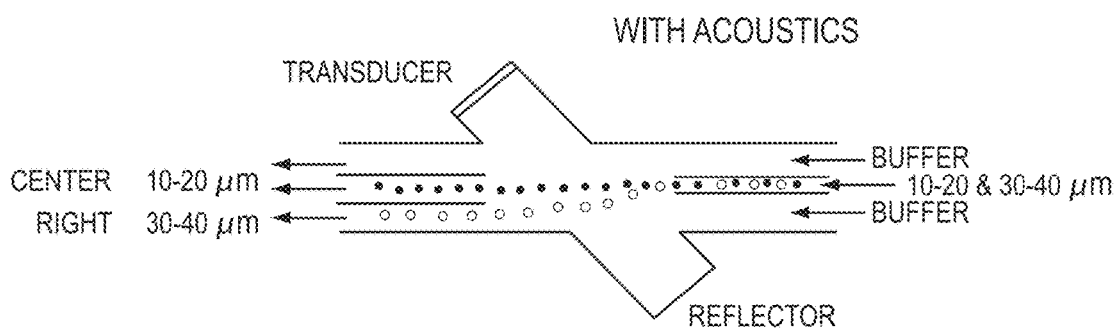
FIGS. 25A-25C present the results of using an AWD system to fractionate a mixed population of beads.
Figure 25B:
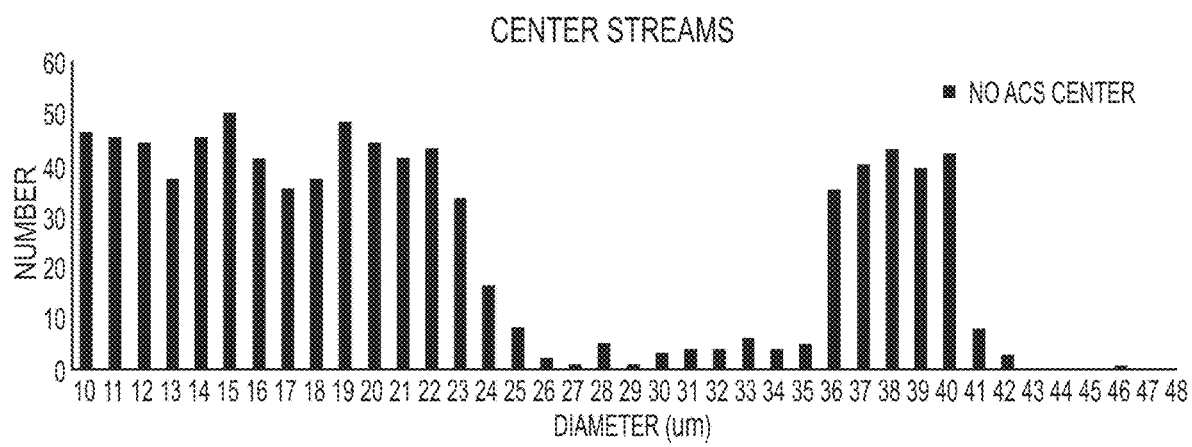
Figure 25C:
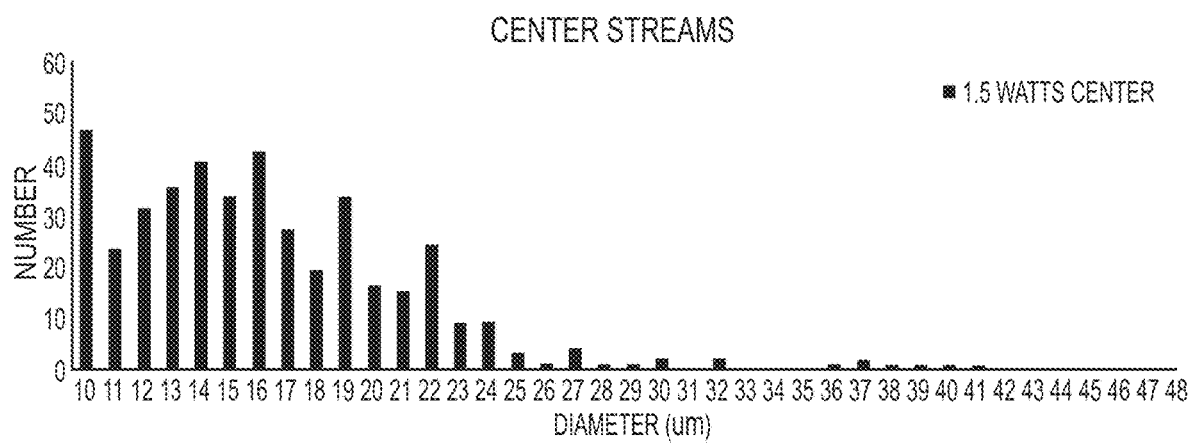

FIGS. 25A-25C present the results of using the same AWD system to fractionate a mixed population of beads with sizes mainly 10 um-29 um and 32 um-42 um. The system had a 30° wave angle and was operated with a frequency of 2.1 MHz and flow rates of 2 ml/min of a bead mixture through the center inlet and of 40 ml/min of a buffer through the buffer inlet. The resulting linear flow velocity was 48 cm/min. FIG. 25A is a schematic illustrating the anticipated separation of larger beads from smaller beads. FIGS. 25B and 25C presents the results. When the system was operated without acoustics, most of the beads of both sizes flowed through the center outlet. When 1.5 W of power were applied, most of the smaller beads still flowed through the center outlet but most of the larger beads were deflected into the buffer outlet.

Figure 26A:
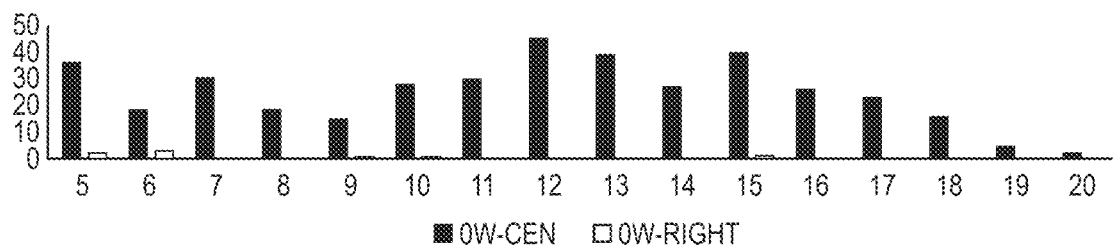
FIGS. 26A-26C present the results of using an AWD system to fractionate a population of PMMA beads.
Figure 26B:
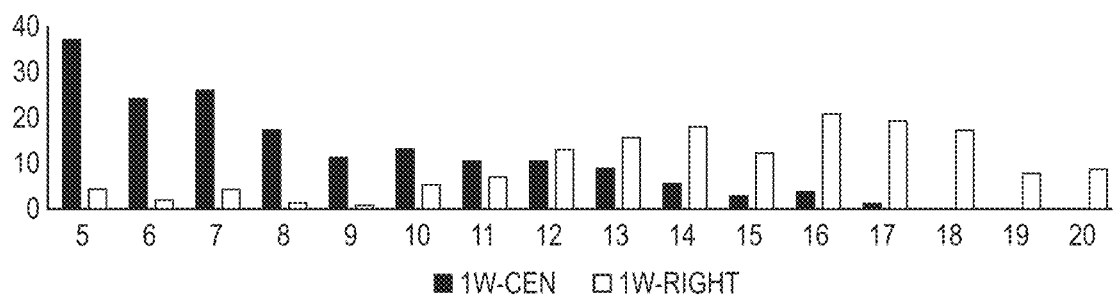
Figure 26C:
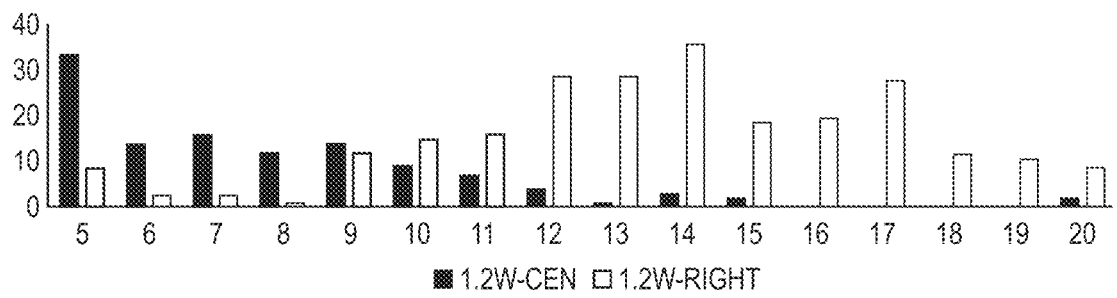

FIGS. 26A-26C present the results of using the same AWD system to fractionate a population of PMMA beads with sizes 5 um-20 um. The system had a 30° wave angle and was operated with a frequency of 2.1 MHz and flow rates of 2 ml/min of a bead mixture through the center inlet and of 40 ml/min of a buffer through the buffer inlet. The resulting linear flow velocity was 48 cm/min. FIG. 26A, 26B, and 26C show the distribution of beads between the center outlet and the buffer outlet without acoustics, with 1W of power applied and with 1.2 W of power applied. When the system was operated without acoustics, most of the beads flowed through the center outlet. When 1 W of power wcro was applied, the larger beads started preferentially being diverted into the buffer outlet. When 1.2 W of power were applied, most of the beads larger than 12 um were deflected into the buffer outlet. These results demonstrate the ability to selectively fractionate material with very small differences.

A number of embodiments of the invention have been described. Nevertheless, it will be understood that various modifications may be made without departing from the spirit and scope of the invention.

Figure 27:
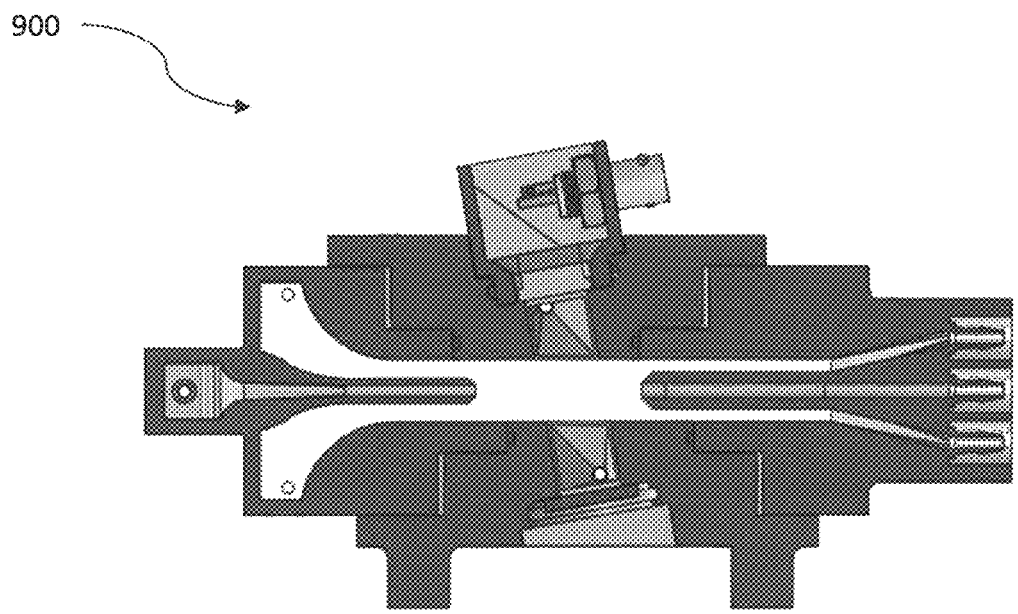
FIG. 27 shows a 10-degree AWD system with a center channel and a buffer channel around it.

For example, FIG. 27 shows a 10-degree AWD system 900 with a center channel and a buffer channel around it. The center channel cross section can be circular or rectangular. A typical cross-section of the system can be from 0.1"×0.1" to a 1"×1" channel with a center channel width ranging from ½ to ¹/₁₀th of the channel cross-section. Applications include cell fractionation, bead-cell fractionation.

Figure 28:
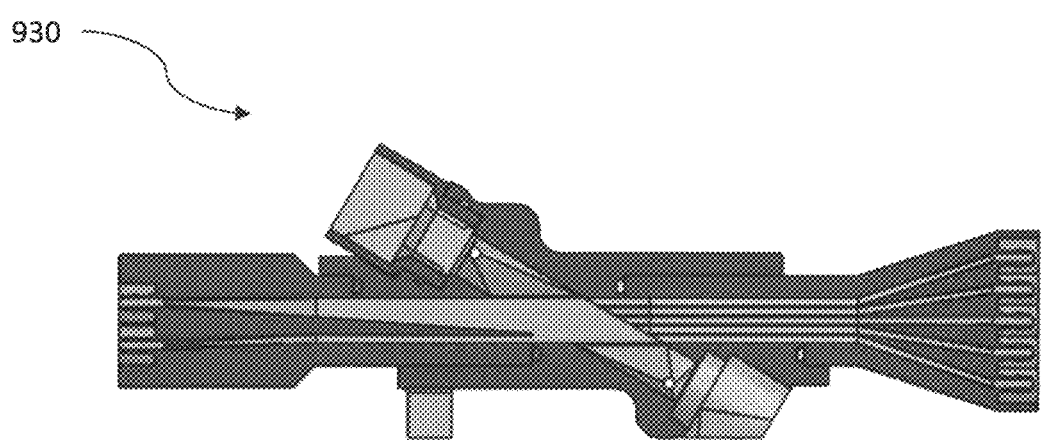
FIG. 28 shows an AWD system that has one small inlet on a side, buffer flow on top of it, and 5 outlets where different fractions from a mixture population will end up.

In another example, FIG. 28 shows an AWD system 930 that has one small inlet on a side and buffer flow on top of it and has 5 outlets where different fractions from a mixture population will end up. A typical size of the channel could be from 0.25"×0.25" to 1"×1" and relative side inlet width could vary from ½ of the channel width to ¹/₁₀th of the channel width. Applications include, for example, leukopack fractionation, T-cell.

Figure 29:
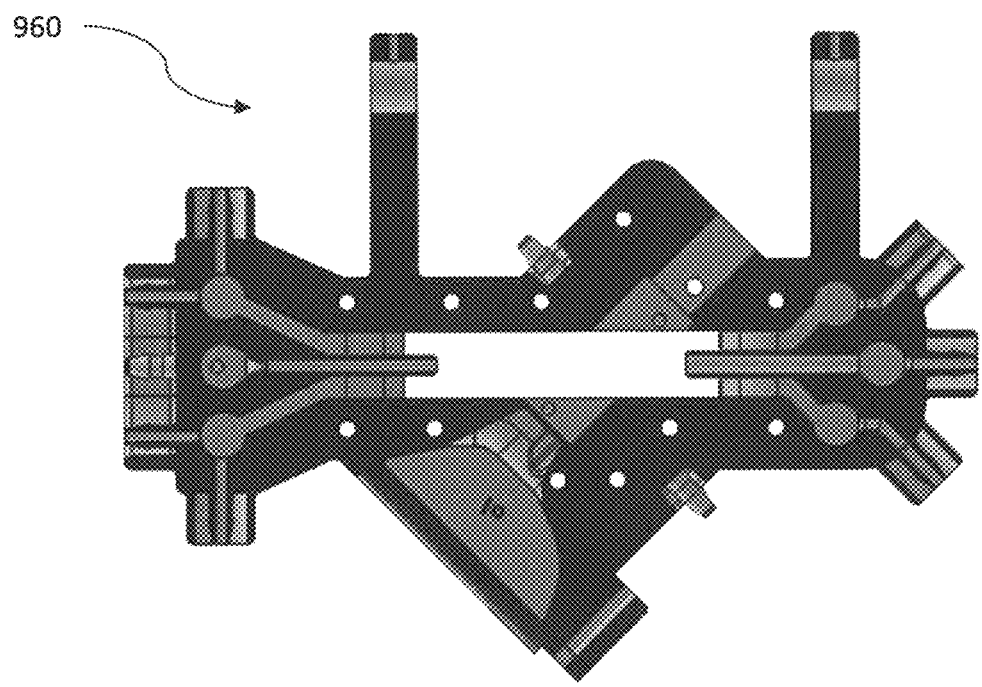
FIG. 29 shows an AWD system in which viewing of the flow is made possible by 2 glass windows.

In another example, FIG. 29 shows an AWD system 960 in which viewing of the flow is made possible by 2 glass windows. Attachments are included so that the system can be suspended vertically with the help of a metal rod. The angled wave system 960 is the same as the 10-degree AWD system 900. This system can be configured with wave angles between 5 to 85 degrees.

Accordingly, other embodiments are within the scope of the following claims.

What is claimed is:

1. A method of separating material from a host fluid, comprising:
flowing an initial mixture of the host fluid and the material via an inlet into an acoustophoretic device at a flow rate, the acoustophoretic device including:
an acoustic chamber communicating with the inlet;
an ultrasonic transducer coupled to the chamber and arranged to be excited to produce a bulk acoustic wave at an angle with a mean direction of flow of the initial mixture;
controlling a ratio of acoustic radiation force produced by the ultrasonic transducer and a viscous drag force of the initial mixture to cause a first subgroup of the material passing through the acoustic wave to deflect at an angle that is different than that of a second subgroup of the material, to thereby permit the first and second subgroups to be separated.

2. The method of claim 1, further comprising controlling the ratio by controlling one or more of the angle, the flow rate, a frequency of excitation of the ultrasonic transducer or power supplied to the ultrasonic transducer.

3. The method of claim 2, further comprising controlling the ratio in a range that is determined by characteristics of subgroups of materials in the mixture to be separated.

4. The method of claim 1, further comprising controlling the ratio based on characteristics of one or more subgroups.

5. The method of claim 4, further comprising controlling the ratio based on one or more of material size, density, compressibility or acoustic contrast factor.

6. The method of claim 1, wherein the material further includes a third subgroup that is different from the first subgroup and the second subgroup, and controlling the ratio further comprises causing the third subgroup to deflect at an angle that is different than that of the first subgroup or the second subgroup.

* * * * *

UNITED STATES PATENT AND TRADEMARK OFFICE
CERTIFICATE OF CORRECTION

PATENT NO. : 11,021,699 B2
APPLICATION NO. : 15/942316
DATED : June 1, 2021
INVENTOR(S) : Bart Lipkens et al.

Page 1 of 1

It is certified that error appears in the above-identified patent and that said Letters Patent is hereby corrected as shown below:

On the Title Page

On page 2, Line 2, in Related U.S. Application Data, item (60) delete "division" and insert
-- continuation --

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*